United States Patent
Rexer et al.

(10) Patent No.: US 12,275,973 B2
(45) Date of Patent: Apr. 15, 2025

(54) ENZYMATIC METHOD FOR PREPARATION OF CMP-NEU5AC

(71) Applicant: Max-Planck-Gesellschaft zur Förderung der Wissenschaften e.V., Munich (DE)

(72) Inventors: Thomas F. T. Rexer, Magdeburg (DE); Reza Mahour, Leipzig (DE)

(73) Assignee: Max-Planck-Gesellschaft zur Förderung der Wissenschaften e. V., Munich (DE)

( * ) Notice: Subject to any disclaimer, the term of this patent is extended or adjusted under 35 U.S.C. 154(b) by 0 days.

(21) Appl. No.: 17/995,816

(22) PCT Filed: Apr. 7, 2021

(86) PCT No.: PCT/EP2021/059101
§ 371 (c)(1),
(2) Date: Oct. 7, 2022

(87) PCT Pub. No.: WO2021/204898
PCT Pub. Date: Oct. 14, 2021

(65) Prior Publication Data
US 2024/0352497 A1     Oct. 24, 2024

(30) Foreign Application Priority Data
Apr. 8, 2020 (EP) .................... 20168848

(51) Int. Cl.
| | |
|---|---|
| C12P 19/46 | (2006.01) |
| C12N 9/12 | (2006.01) |
| C12N 9/14 | (2006.01) |
| C12N 9/88 | (2006.01) |
| C12N 9/90 | (2006.01) |

(52) U.S. Cl.
CPC ............ *C12P 19/46* (2013.01); *C12N 9/1205* (2013.01); *C12N 9/1229* (2013.01); *C12N 9/1241* (2013.01); *C12N 9/14* (2013.01); *C12N 9/88* (2013.01); *C12N 9/90* (2013.01); *C12Y 207/01048* (2013.01); *C12Y 207/04014* (2013.01); *C12Y 207/07043* (2013.01); *C12Y 306/01001* (2013.01); *C12Y 306/01011* (2013.01); *C12Y 401/03003* (2013.01); *C12Y 501/03008* (2013.01)

(58) Field of Classification Search
CPC ...................................................... C12P 19/46
See application file for complete search history.

(56) References Cited

FOREIGN PATENT DOCUMENTS

| | | |
|---|---|---|
| EP | 1541693 A1 | 6/2005 |
| EP | 3009516 A1 | 4/2016 |
| EP | 4103730 B1 | 11/2023 |
| JP | 2002-085087 | 3/2002 |

OTHER PUBLICATIONS

Bhattacharjee et al., "Structural Determination of the Sialic Acid Polysaccharide Antigens of *Neisseria meningitidis* Serogroups B and C with Carbon 13 Nuclear Magnetic Resonance" J. Biol. Chem. (1975) 250(5):1926-1932.
Bioconjugation Protocols: Strategies and Methods, In Methods in Molecular Biology, C.M. Niemeyer ed., Humana Press (2004)—Table of Contents only.
Bravo et al., "Kinetic properties of the acylneuraminate cytidylyltransferase from *Pasteurella haemolytica* A2" Biochem. J. (2001) 258:568-598.
Datta et al. "Enzyme immobilization: an overview on techniques and support materials" Biotech (2013) 3:1-9.
Endo et al., "Large-scale production of CMP-NeuAc and sialylated oligosaccharides through bacterial coupling" Appl. Microbiol. Biotechnol. (2000) 53(1):257-261.
Hermanson, G.T., Bioconjugate Techniques, Second Edition, Academic Press (2008)—Table of Contents only.
Hu et al., "Coupled bioconversion for preparation of N-acetyl-D-neuraminic acid using immobilized N-acetyl-D-glucosamine-2-epimerase and N-acetyl-D-neuraminic acid lyase" Appl. Microbiol. Biotechnol. (2010) 85(5):1383-1391.
Koszelewski et al., "Immobilization of ω-transaminases by encapsulation in a sol-gel/celite matrix" Journal of Molecular Catalysis B: Enzymatic (2010) 63:39-44.
Mahour et al., "Establishment of a five-enzyme cell-free cascade for the synthesis of uridine diphosphate N-acetylglucosamine" Journal of Biotechnology (2018) 283:120-129.
Martin et al., "Characterization of free and immobilized (S)-aminotransferase for acetophenone production" Applied Microbiology and Biotechnology (2007) 76:843-851.
Maru et al., "Simple and large-scale production of N-acetylneuraminic acid from N-acetyl-D-glucosamine and pyruvate using N-acyl-D-glucosamine 2-epimerase and N-acetylneuraminate lyase" Carbohydrate Research (1998) 306(4):575-578.
Mateo et al., "Epoxy Sepabeads: A Novel Epoxy Support for Stabilization of Industrial Enzymes via Very Intense Multipoint Covalent Attachment" Biotechnology Progress (2002) 18:629-634.
Rexer et al., One pot synthesis of GDP-mannose by a multi-enzyme cascade for enzymatic assembly of lipid-linked oligosaccharides. Biotechnology and Bioengineering (2018) 115(1):192-205.

(Continued)

*Primary Examiner* — Suzanne M Noakes
(74) *Attorney, Agent, or Firm* — Knobbe Martens Olson & Bear LLP

(57) ABSTRACT

The present invention relates to a method for producing cytidine 5'-monophospho-N-acetyl-neuraminic acid (CMP-Neu5Ac, 1) from low-cost substrates N-acetyl-D-glucosamine (GlcNAc), pyruvate, cytidine and polyphosphate in a single reaction mixture with a set of optionally immobilized or optionally co-immobilized enzymes comprising N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3). Further, said process may be adapted to produce Neu5Acylated i.e. sialylated biomolecules and biomolecules including a saccharide, a peptide, a protein, a glycopeptide, a glycoprotein, a glycolipid, a glycan, an antibody, and a glycoconjugate, in particular, an antibody drug conjugate, and a carbohydrate conjugate vaccine, or a flavonoid.

18 Claims, 20 Drawing Sheets
Specification includes a Sequence Listing.

(56) References Cited

OTHER PUBLICATIONS

Simon et al., "Synthesis of CMP-NeuAc form N-Acetylglucosamine Generation of CTP from CMP Using Adenylate Kinase" J. Am. Chem. Soc. (1988) 110(21):7159-7163.
Song et al., "Reassembled Biosynthetic Pathway for a Large-scale Synthesis of CMP-Neu5Ac" Drugs (Mar. 2003) 1(1):34-45.
Truppo et al., "Development of an Improved Immobilized CAL-B for the Enzymatic Resolution of a Key Intermediate to Odanacatib" Org. Process Res. Dev., 2011, 15, 1033-1035.
Wu et al., "Concomitant use of immobilized uridine-cytidine kinase and polyphosphate kinase for 5'-cytidine monophosphate production" Chinese Journal of Biotechnology (2020) 36(5):1002-1011.
Yi et al., "Covalent information of ω-transaminase from *Vibrio fluvialis* JS17 on chitosan beads" Process Biochemistry (2007) 42:895-898.
Yu et al., "Chemoenzymatic synthesis of CMP-sialic acid derivatives by a one-pot two-enzyme system: comparison of substrate flexibility of three microbial CMP-sialic acid synthetases" Bioorganic & Medicinal Chemistry (2004) 12(24):6427-6435.
Zdarta et al. "A General Overview of Support Materials for Enzyme Immobilization: Characteristics, Properties, Practical Utility" Catalysts (2018) 8:92.
International Search Report and Written Opinion mailed Jun. 29, 2021 for PCT Application No. PCT/EP2021/059101, filed Apr. 7, 2021.

Figure 1
(A)
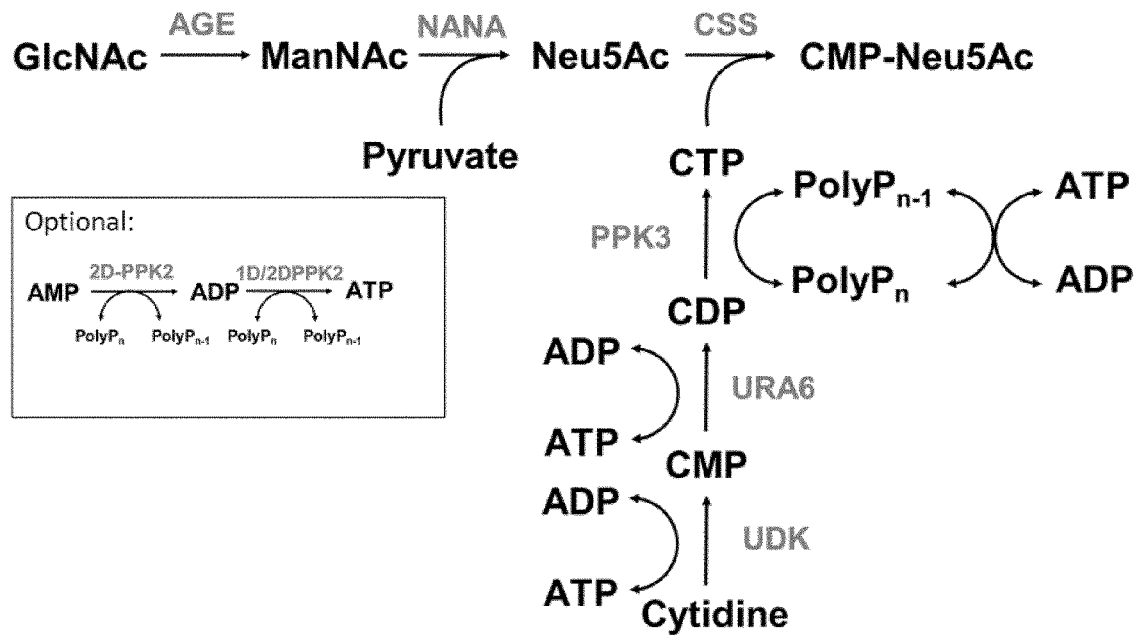
(B)
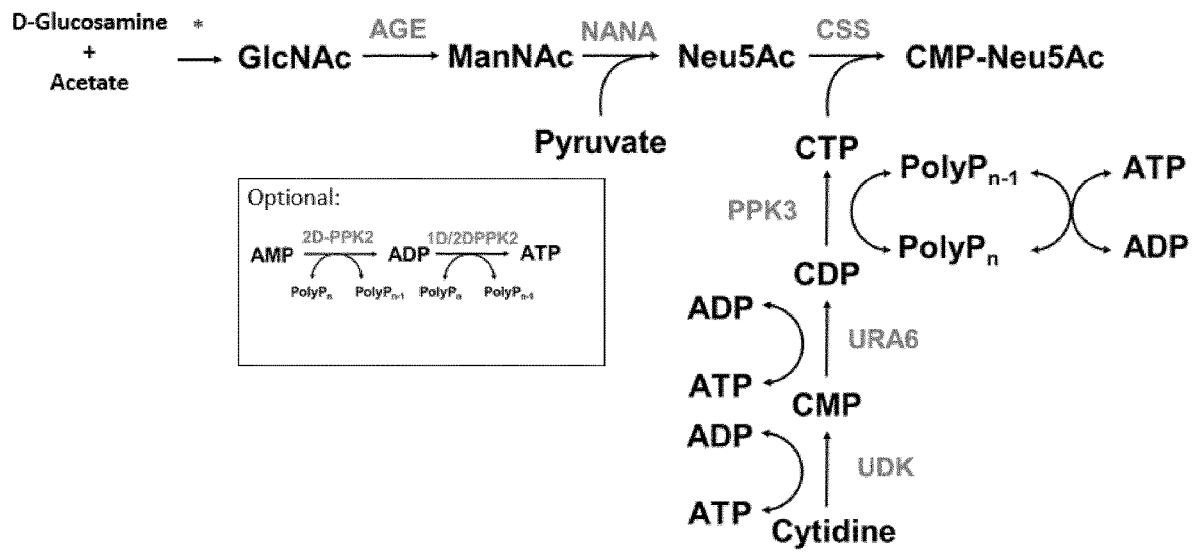
\* *N*-acetylglucosamine deacetylase

Figure 3
(A)
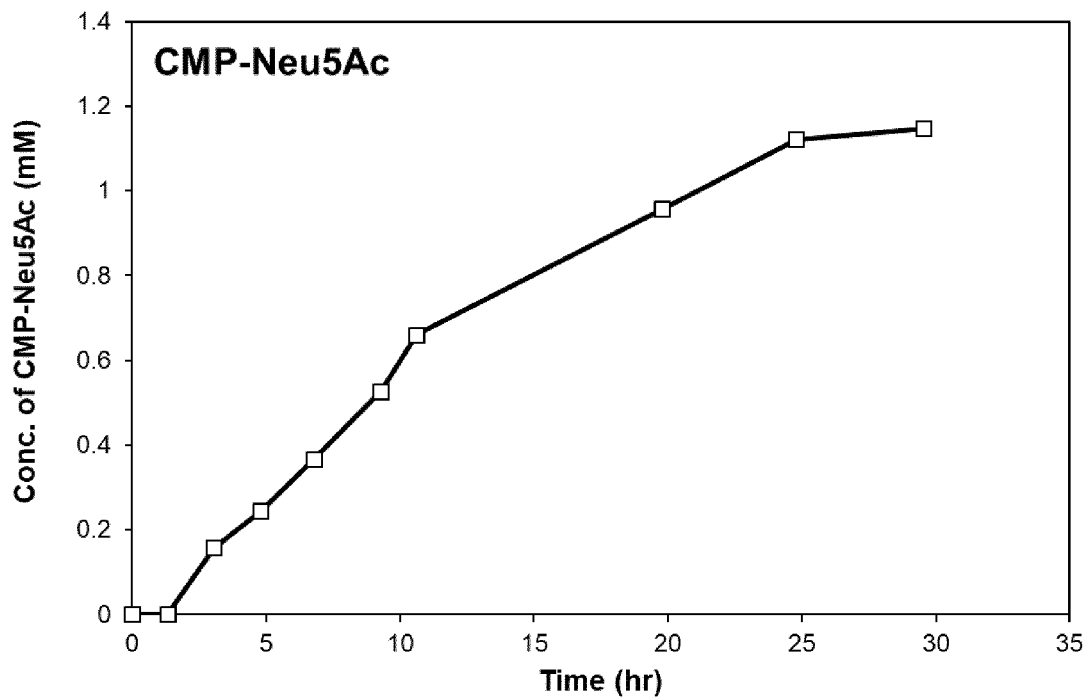
(B)
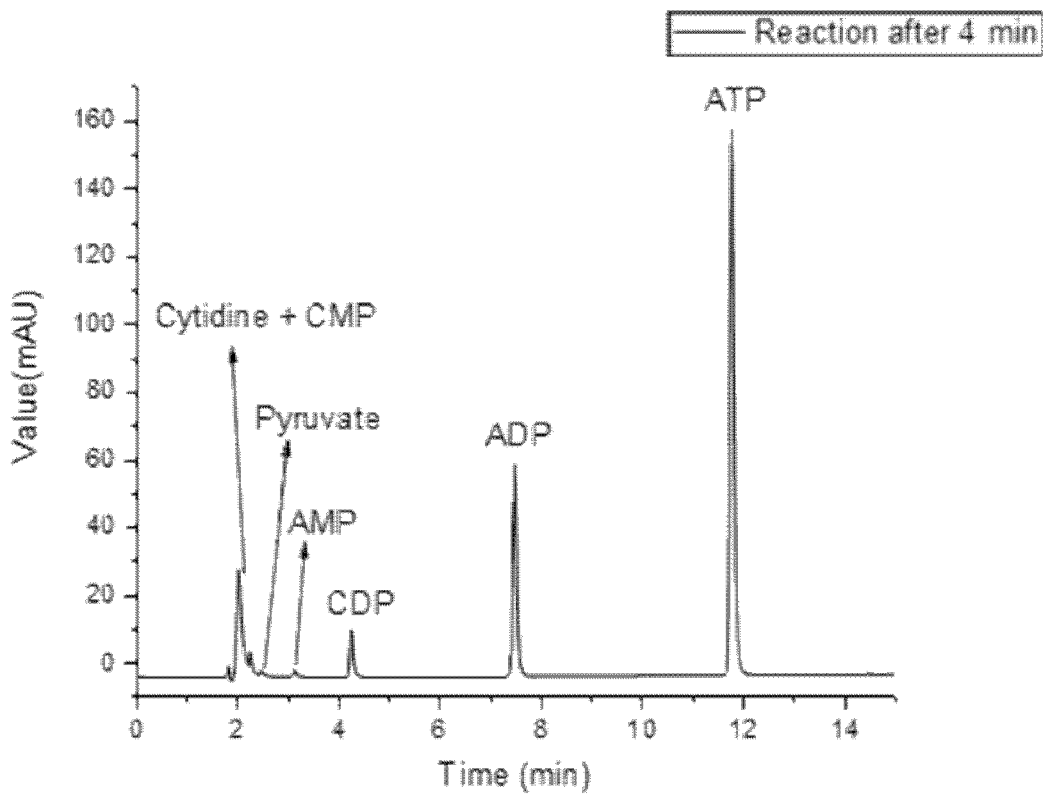

Figure 4

(A) AGE family epimerase/isomerase – SEQ ID NO: 1
*Trichormus variabilis*

MGKNLQALAQLYKNALLNDVLPFWENYSLDSEGGYFTCLDRQGKVYDTDKFIWLQNRQVWT
FSMLCNQLEKRENWLKIARNGAKFLAQHGRDDEGNWYFALTRGGEPLVQPYNIFSDCFAAM
AFSQYALASGEEWSKDVAMQAYNNVLRRKDNPKGKYTKTYPGTRPMKALAVPMILANLTLE
MEWLLPQETLENVLAATVQEVMGDFLDQERGLMYENVAPDGSHIDCFEGRLINPGHGIEAM
WFIMDIARRKNDSKTINQAVDVVLNILNFAWDNEYGGLYYFMDAAGHPPQQLEWDQKLWWV
HLESLVALAMGYRLTGREVCWEWYQKMHDYSWQHFADPEYGEWFGYLNRRGEVLLNLKGGK
WKGCFHVPRALYLCWQQFEALSLQSA

(B) N-acetylneuraminate lyase (NAL) - SEQ ID NO: 2
*Pasteurella multocida (strain Pm70)*

MKNLKGIFSALLVSFNADGSINEKGLRQIVRYNIDKMKVDGLYVGGSTGENFMLSTEEKKE
IFRIAKDEAKDEIALIAQVGSVNLQEAIELGKYATELGYDSLSAVTPFYYKFSFPEIKHYY
DSIIEATGNYMIVYSIPFLTGVNIGVEQFGELYKNPKVLGVKFTAGDFYLLERLKKAYPNH
LIWAGFDEMMLPAASLGVDGAIGSTFNVNGVRARQIFELTQAGKLKEALEIQHVTNDLIEG
ILANGLYLTIKELLKLDGVEAGYCREPMTKELSPEKVAFAKELKAKYLS

(C) N-acylneuraminate cytidylyltransferase (CSS) - SEQ ID NO: 3
*Neisseria meningitidis serogroup B (strain MC58)*

MEKQNIAVILARQNSKGLPLKNLRKMNGISLLGHTINAAISSKCFDRIIVSTDGGLIAEEA
KNFGVEVVLRPAELASDTASSISGVIHALETIGSNSGTVTLLQPTSPLRTGAHIREAFSLF
DEKIKGSVVSACPMEHHPLKTLLQINNGEYAPMRHLSDLEQPRQQLPQAFRPNGAIYINDT
ASLIANNCFFIAPTKLYIMSHQDSIDIDTELDLQQAENILNHKES

(D) Uridine kinase (UDK) - SEQ ID NO: 4
*Escherichia coli (strain K12)*

MTDQSHQCVIIGIAGASASGKSLIASTLYRELREQVGDEHIGVIPEDCYYKDQSHLSMEER
VKTNYDHPSAMDHSLLLEHLQALKRGSAIDLPVYSYVEHTRMKETVTVEPKKVIILEGILL
LTDARLRDELNFSIFVDTPLDICLMRRIKRDVNERGRSMDSVMAQYQKTVRPMFLQFIEPS
KQYADIIVPRGGKNRIAIDILKAKISQFFE

Figure 4 continued

(E) UMP-CMP kinase 3 (URA6) - SEQ ID NO: 5
*Arabidopsis thaliana*

```
MGSVDAANGSGKKPTVIFVLGGPGSGKGTQCAYIVEHYGYTHLSAGDLLRAEIKSGSENGT
MIQNMIKEGKIVPSEVTIKLLQKAIQENGNDKFLIDGFPRNEENRAAFEKVTEIEPKFVLF
FDCPEEEMEKRLLGRNQGREDDNIETIRKRFKVFLESSLPVIHYYEAKGKVRKINAAKPIE
AVFEEVKAIFSPEAEKVEA
```

(F) Polyphosphate:NDP phosphotransferase 3 (PPK3) - SEQ ID NO: 6
*Ruegeria pomeroyi (strain ATCC 700808 / DSM 15171 / DSS-3)*

```
MNRNGSTKDPRRMTGAATGEISRYFNDKAPKDIRRAIEKADKDDILSTTYPYDAEMTAKDY
RAQMEALQIELVKLQAWIKQSGARVALLFEGRDAAGKGGTIKRFRENLNPRGARVVALSKP
TEAERSQWYFQRYIQHLPSAGELVFYDRSWYNRGVVEHVFGWCDEEQRERFFRQVMPFEHD
LVDDGIHLFKFWLNVGRAEQLRRFHDRERDPLKQWKLSPVDIAGLDKWEAYTTAISQTLTR
SHSDRAPWTVIRSDDKKRARLAAIRTVLSGIDYDNKDRAAVGQPDAAICGGPDIWDA
```

(G) Inorganic pyrophosphatase (PPA) - SEQ ID NO: 7
*Pasteurella multocida (strain Pm70)*

```
MGLETVPAGKALPDDIYVVIEIPANSDPIKYEVDKESGALFVDRFMATAMFYPANYGYVNN
TLSLDGDPVDVLVPTPYPLQPGSVIRCRPVGVLKMTDEAGSDAKVVAVPHSKLTKEYDHIK
DVNDLPALLKAQIQHFFESYKALEAGKWVKVDGWEGVDAARQEILDSFERAKK
```

(H) Polyphosphate: AMP phosphotransferase (2D-PPK2) -- SEQ ID NO: 8
*Pseudomonas aeruginosa (strain ATCC 15692 / DSM 22644 / CIP 104116 / JCM 14847 / LMG 12228 / 1C / PRS 101 / PAO1)*
Uniprot-ID: Q9HYF1

```
MVFESAEVGHSIDKDTYEKAVIELREALLEAQFELKQQARFPVIILINGIEGAGKGETVK
LLNEWMDPRLIEVQSFLRPSDEELERPPQWRFWRRLPPKGRTGIFFGNWYSQMLYARVEG
HIKEAKLDQAIDAAERFERMLCDEGALLFKFWFHLSKKQLKERLKALEKDPQHSWKLSPL
DWKQSEVYDRFVHYGERVLRRTSRDYAPWYVVEGADERYRALTVGRILLEGLQAALATKE
RAKRQPHAAPLVSSLDNRGLLDSLDLGQYLDKDAYKEQLAAEQARLAGLIRDKRFRQHSL
VAVFEGNDAAGKGGAIRRVTDALDPRQYHIVPIAAPTEEERAQPYLWRFWRHIPARRQFT
IFDRSWYGRVLVERIEGFCAPADWLRAYGEINDFEEQLSEYGIIVVKFWLAIDKQTQMER
FKEREKTPYKRYKITEEDWRNRDKWDQYVDAVGDMVDRTSTEIAPWTLVEANDKRFARVK
VLRTINDAIEAAYKKDKLEHHHHHH
```

Figure 4 continued

(I) Polyphosphate:ADP phosphotransferase (1D-PPK2) -- SEQ ID NO: 9
*Pseudomonas aeruginosa (strain ATCC 15692 / DSM 22644 / CIP 104116 / JCM 14847 / LMG 12228 / 1C / PRS 101 / PAO1)*
Uniprot-ID: Q9I154

```
MGSSHHHHHHSSGLVPRGSHMDSYGDTSGRIGRDWLDRHDEELEQELLDDELNLDELFGP
EQEDAPGELSRRRYFRELFRLQRELVKLQNWVVHTGHKVVILFEGRDAAGKGGVIKRITQ
RLNPRVCRVAALPAPNDREQTQWYFQRYVSHLPAGGEIVLFDRSWYNRAGVERVMGFCND
EQYEEFFRSVPEFEKMLARSGIQLLKYWFSISDAEQHLRFLSRIHDPLKQWKLSPMDLES
RRRWEAYTKAKETMLERTHIPEAPWWVVQADDKKRARLNCIHHLLQQMPYREVPQPPVHL
PERLRHADYVRHPTPGEIIVPEVY
```

Figure 28
A.
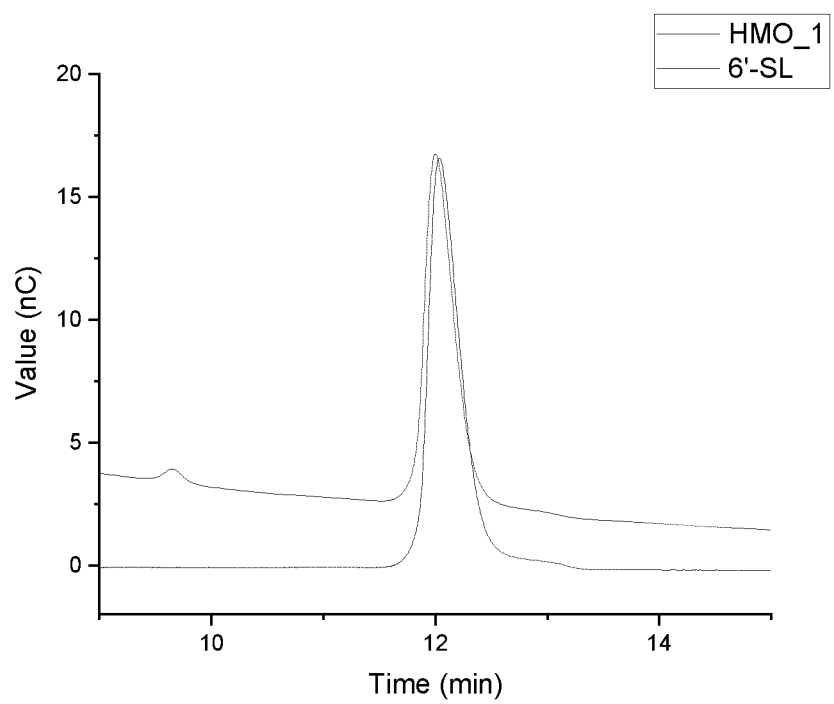
B.
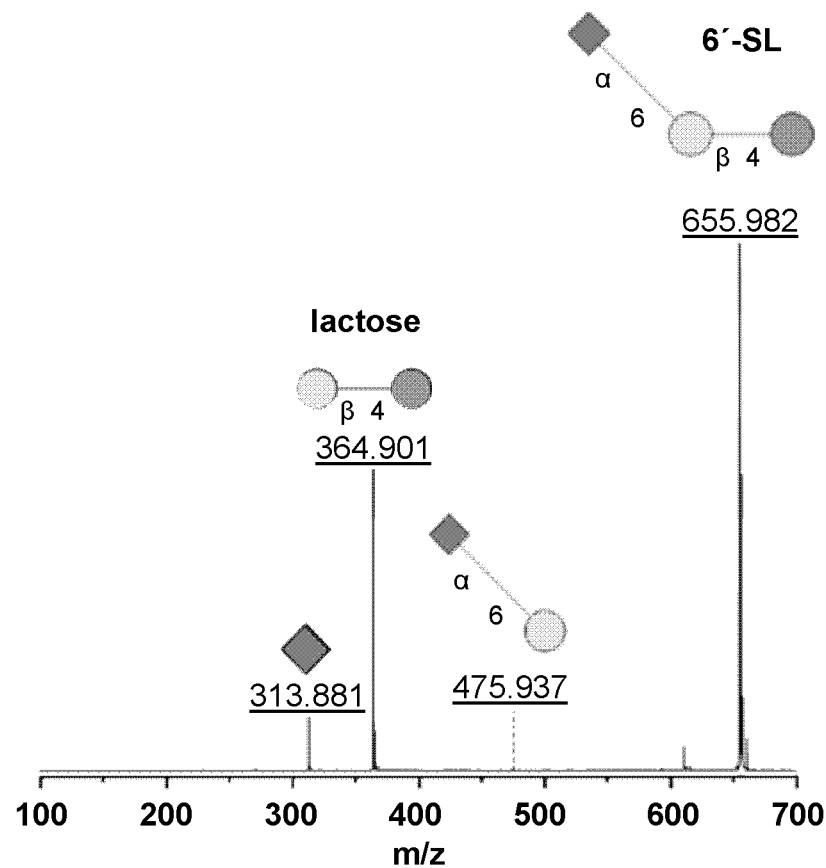

```
                        SEQUENCE LISTING

<160> NUMBER OF SEQ ID NOS: 9

<210> SEQ ID NO 1
<211> LENGTH: 392
<212> TYPE: PRT
<213> ORGANISM: Trichormus variabilis
<220> FEATURE:
<221> NAME/KEY: PEPTIDE
<222> LOCATION: (1)..(392)
<223> OTHER INFORMATION: AGE family epimerase/isomerase

<400> SEQUENCE: 1

Met Gly Lys Asn Leu Gln Ala Leu Ala Gln Leu Tyr Lys Asn Ala Leu
1               5                   10                  15

Leu Asn Asp Val Leu Pro Phe Trp Glu Asn Tyr Ser Leu Asp Ser Glu
            20                  25                  30

Gly Gly Tyr Phe Thr Cys Leu Asp Arg Gln Gly Lys Val Tyr Asp Thr
        35                  40                  45

Asp Lys Phe Ile Trp Leu Gln Asn Arg Gln Val Trp Thr Phe Ser Met
    50                  55                  60

Leu Cys Asn Gln Leu Glu Lys Arg Glu Asn Trp Leu Lys Ile Ala Arg
65                  70                  75                  80

Asn Gly Ala Lys Phe Leu Ala Gln His Gly Arg Asp Asp Glu Gly Asn
                85                  90                  95

Trp Tyr Phe Ala Leu Thr Arg Gly Gly Glu Pro Leu Val Gln Pro Tyr
            100                 105                 110

Asn Ile Phe Ser Asp Cys Phe Ala Ala Met Ala Phe Ser Gln Tyr Ala
        115                 120                 125

Leu Ala Ser Gly Glu Glu Trp Ser Lys Asp Val Ala Met Gln Ala Tyr
    130                 135                 140

Asn Asn Val Leu Arg Arg Lys Asp Asn Pro Lys Gly Lys Tyr Thr Lys
145                 150                 155                 160
```

Thr Tyr Pro Gly Thr Arg Pro Met Lys Ala Leu Ala Val Pro Met Ile
                165                 170                 175

Leu Ala Asn Leu Thr Leu Glu Met Glu Trp Leu Leu Pro Gln Glu Thr
            180                 185                 190

Leu Glu Asn Val Leu Ala Ala Thr Val Gln Glu Val Met Gly Asp Phe
        195                 200                 205

Leu Asp Gln Glu Arg Gly Leu Met Tyr Glu Asn Val Ala Pro Asp Gly
    210                 215                 220

Ser His Ile Asp Cys Phe Gly Arg Leu Ile Asn Pro Gly His Gly
225                 230                 235                 240

Ile Glu Ala Met Trp Phe Ile Met Asp Ile Ala Arg Arg Lys Asn Asp
                245                 250                 255

Ser Lys Thr Ile Asn Gln Ala Val Asp Val Val Leu Asn Ile Leu Asn
            260                 265                 270

Phe Ala Trp Asp Asn Glu Tyr Gly Gly Leu Tyr Tyr Phe Met Asp Ala
        275                 280                 285

Ala Gly His Pro Pro Gln Gln Leu Glu Trp Asp Gln Lys Leu Trp Trp
    290                 295                 300

Val His Leu Glu Ser Leu Val Ala Leu Ala Met Gly Tyr Arg Leu Thr
305                 310                 315                 320

Gly Arg Glu Val Cys Trp Glu Trp Tyr Gln Lys Met His Asp Tyr Ser
                325                 330                 335

Trp Gln His Phe Ala Asp Pro Glu Tyr Gly Glu Trp Phe Gly Tyr Leu
            340                 345                 350

Asn Arg Arg Gly Glu Val Leu Leu Asn Leu Lys Gly Gly Lys Trp Lys
        355                 360                 365

Gly Cys Phe His Val Pro Arg Ala Leu Tyr Leu Cys Trp Gln Gln Phe
    370                 375                 380

Glu Ala Leu Ser Leu Gln Ser Ala
385                 390

<210> SEQ ID NO 2
<211> LENGTH: 293
<212> TYPE: PRT
<213> ORGANISM: Pasteurella multocida
<220> FEATURE:
<221> NAME/KEY: PEPTIDE
<222> LOCATION: (1)..(293)
<223> OTHER INFORMATION: N-acetylneuraminate lyase (NAL)

<400> SEQUENCE: 2

Met Lys Asn Leu Lys Gly Ile Phe Ser Ala Leu Leu Val Ser Phe Asn
1               5                   10                  15

Ala Asp Gly Ser Ile Asn Glu Lys Gly Leu Arg Gln Ile Val Arg Tyr
                20                  25                  30

Asn Ile Asp Lys Met Lys Val Asp Gly Leu Tyr Val Gly Gly Ser Thr
            35                  40                  45

Gly Glu Asn Phe Met Leu Ser Thr Glu Glu Lys Lys Glu Ile Phe Arg
        50                  55                  60

Ile Ala Lys Asp Glu Ala Lys Asp Glu Ile Ala Leu Ile Ala Gln Val
65                  70                  75                  80

Gly Ser Val Asn Leu Gln Glu Ala Ile Glu Leu Gly Lys Tyr Ala Thr
                85                  90                  95

Glu Leu Gly Tyr Asp Ser Leu Ser Ala Val Thr Pro Phe Tyr Tyr Lys
            100                 105                 110

```
Phe Ser Phe Pro Glu Ile Lys His Tyr Tyr Asp Ser Ile Ile Glu Ala
            115                 120                 125

Thr Gly Asn Tyr Met Ile Val Tyr Ser Ile Pro Phe Leu Thr Gly Val
        130                 135                 140

Asn Ile Gly Val Glu Gln Phe Gly Leu Tyr Lys Asn Pro Lys Val
145                 150                 155                 160

Leu Gly Val Lys Phe Thr Ala Gly Asp Phe Tyr Leu Leu Glu Arg Leu
                165                 170                 175

Lys Lys Ala Tyr Pro Asn His Leu Ile Trp Ala Gly Phe Asp Glu Met
            180                 185                 190

Met Leu Pro Ala Ala Ser Leu Gly Val Asp Gly Ala Ile Gly Ser Thr
        195                 200                 205

Phe Asn Val Asn Gly Val Arg Ala Arg Gln Ile Phe Glu Leu Thr Gln
    210                 215                 220

Ala Gly Lys Leu Lys Glu Ala Leu Glu Ile Gln His Val Thr Asn Asp
225                 230                 235                 240

Leu Ile Glu Gly Ile Leu Ala Asn Gly Leu Tyr Leu Thr Ile Lys Glu
                245                 250                 255

Leu Leu Lys Leu Asp Gly Val Glu Ala Gly Tyr Cys Arg Glu Pro Met
            260                 265                 270

Thr Lys Glu Leu Ser Pro Glu Lys Val Ala Phe Ala Lys Glu Leu Lys
        275                 280                 285

Ala Lys Tyr Leu Ser
        290

<210> SEQ ID NO 3
<211> LENGTH: 228
<212> TYPE: PRT
<213> ORGANISM: Neisseria meningitidis (group B)
<220> FEATURE:
<221> NAME/KEY: PEPTIDE
<222> LOCATION: (1)..(228)
<223> OTHER INFORMATION: N-acylneuraminate cytidylyltransferase (CSS)

<400> SEQUENCE: 3

Met Glu Lys Gln Asn Ile Ala Val Ile Leu Ala Arg Gln Asn Ser Lys
1               5                   10                  15

Gly Leu Pro Leu Lys Asn Leu Arg Lys Met Asn Gly Ile Ser Leu Leu
            20                  25                  30

Gly His Thr Ile Asn Ala Ala Ile Ser Ser Lys Cys Phe Asp Arg Ile
        35                  40                  45

Ile Val Ser Thr Asp Gly Gly Leu Ile Ala Glu Glu Ala Lys Asn Phe
    50                  55                  60

Gly Val Glu Val Val Leu Arg Pro Ala Glu Leu Ala Ser Asp Thr Ala
65                  70                  75                  80

Ser Ser Ile Ser Gly Val Ile His Ala Leu Glu Thr Ile Gly Ser Asn
                85                  90                  95

Ser Gly Thr Val Thr Leu Leu Gln Pro Thr Ser Pro Leu Arg Thr Gly
            100                 105                 110

Ala His Ile Arg Glu Ala Phe Ser Leu Phe Asp Glu Lys Ile Lys Gly
        115                 120                 125

Ser Val Val Ser Ala Cys Pro Met Glu His His Pro Leu Lys Thr Leu
    130                 135                 140

Leu Gln Ile Asn Asn Gly Glu Tyr Ala Pro Met Arg His Leu Ser Asp
145                 150                 155                 160
```

```
Leu Glu Gln Pro Arg Gln Leu Pro Gln Ala Phe Arg Pro Asn Gly
            165                 170                 175

Ala Ile Tyr Ile Asn Asp Thr Ala Ser Leu Ile Ala Asn Asn Cys Phe
            180                 185                 190

Phe Ile Ala Pro Thr Lys Leu Tyr Ile Met Ser His Gln Asp Ser Ile
            195                 200                 205

Asp Ile Asp Thr Glu Leu Asp Leu Gln Gln Ala Glu Asn Ile Leu Asn
            210                 215                 220

His Lys Glu Ser
225

<210> SEQ ID NO 4
<211> LENGTH: 213
<212> TYPE: PRT
<213> ORGANISM: Escherichia coli
<220> FEATURE:
<221> NAME/KEY: PEPTIDE
<222> LOCATION: (1)..(213)
<223> OTHER INFORMATION: Uridine kinase (UDK)

<400> SEQUENCE: 4

Met Thr Asp Gln Ser His Gln Cys Val Ile Gly Ile Ala Gly Ala
1               5                   10                  15

Ser Ala Ser Gly Lys Ser Leu Ile Ala Ser Thr Leu Tyr Arg Glu Leu
            20                  25                  30

Arg Glu Gln Val Gly Asp Glu His Ile Gly Val Ile Pro Glu Asp Cys
        35                  40                  45

Tyr Tyr Lys Asp Gln Ser His Leu Ser Met Glu Glu Arg Val Lys Thr
50                  55                  60

Asn Tyr Asp His Pro Ser Ala Met Asp His Ser Leu Leu Leu Glu His
65                  70                  75                  80

Leu Gln Ala Leu Lys Arg Gly Ser Ala Ile Asp Leu Pro Val Tyr Ser
                85                  90                  95

Tyr Val Glu His Thr Arg Met Lys Glu Thr Val Thr Val Glu Pro Lys
            100                 105                 110

Lys Val Ile Ile Leu Glu Gly Ile Leu Leu Leu Thr Asp Ala Arg Leu
        115                 120                 125

Arg Asp Glu Leu Asn Phe Ser Ile Phe Val Asp Thr Pro Leu Asp Ile
130                 135                 140

Cys Leu Met Arg Arg Ile Lys Arg Asp Val Asn Glu Arg Gly Arg Ser
145                 150                 155                 160

Met Asp Ser Val Met Ala Gln Tyr Gln Lys Thr Val Arg Pro Met Phe
                165                 170                 175

Leu Gln Phe Ile Glu Pro Ser Lys Gln Tyr Ala Asp Ile Ile Val Pro
            180                 185                 190

Arg Gly Gly Lys Asn Arg Ile Ala Ile Asp Ile Leu Lys Ala Lys Ile
        195                 200                 205

Ser Gln Phe Phe Glu
    210

<210> SEQ ID NO 5
<211> LENGTH: 202
<212> TYPE: PRT
<213> ORGANISM: Arabidopsis thaliana
<220> FEATURE:
<221> NAME/KEY: PEPTIDE
<222> LOCATION: (1)..(202)
<223> OTHER INFORMATION: UMP-CMP kinase 3
```

-continued

```
<400> SEQUENCE: 5

Met Gly Ser Val Asp Ala Ala Asn Gly Ser Gly Lys Lys Pro Thr Val
1               5                   10                  15

Ile Phe Val Leu Gly Gly Pro Gly Ser Gly Lys Gly Thr Gln Cys Ala
            20                  25                  30

Tyr Ile Val Glu His Tyr Gly Tyr Thr His Leu Ser Ala Gly Asp Leu
        35                  40                  45

Leu Arg Ala Glu Ile Lys Ser Gly Ser Glu Asn Gly Thr Met Ile Gln
50                  55                  60

Asn Met Ile Lys Glu Gly Lys Ile Val Pro Ser Glu Val Thr Ile Lys
65                  70                  75                  80

Leu Leu Gln Lys Ala Ile Gln Glu Asn Gly Asn Asp Lys Phe Leu Ile
                85                  90                  95

Asp Gly Phe Pro Arg Asn Glu Glu Asn Arg Ala Ala Phe Glu Lys Val
            100                 105                 110

Thr Glu Ile Glu Pro Lys Phe Val Leu Phe Phe Asp Cys Pro Glu Glu
        115                 120                 125

Glu Met Glu Lys Arg Leu Leu Gly Arg Asn Gln Gly Arg Glu Asp Asp
130                 135                 140

Asn Ile Glu Thr Ile Arg Lys Arg Phe Lys Val Phe Leu Glu Ser Ser
145                 150                 155                 160

Leu Pro Val Ile His Tyr Tyr Glu Ala Lys Gly Lys Val Arg Lys Ile
                165                 170                 175

Asn Ala Ala Lys Pro Ile Glu Ala Val Phe Glu Glu Val Lys Ala Ile
            180                 185                 190

Phe Ser Pro Glu Ala Glu Lys Val Glu Ala
        195                 200

<210> SEQ ID NO 6
<211> LENGTH: 301
<212> TYPE: PRT
<213> ORGANISM: Ruegeria pomeroyi
<220> FEATURE:
<221> NAME/KEY: PEPTIDE
<222> LOCATION: (1)..(301)
<223> OTHER INFORMATION: Polyphosphate:NDP phosphotransferase 3 (PPK3)

<400> SEQUENCE: 6

Met Asn Arg Asn Gly Ser Thr Lys Asp Pro Arg Met Thr Gly Ala
1               5                   10                  15

Ala Thr Gly Glu Ile Ser Arg Tyr Phe Asn Asp Lys Ala Pro Lys Asp
            20                  25                  30

Ile Arg Arg Ala Ile Glu Lys Ala Asp Lys Asp Ile Leu Ser Thr
        35                  40                  45

Thr Tyr Pro Tyr Asp Ala Glu Met Thr Ala Lys Asp Tyr Arg Ala Gln
50                  55                  60

Met Glu Ala Leu Gln Ile Glu Leu Val Lys Leu Gln Ala Trp Ile Lys
65                  70                  75                  80

Gln Ser Gly Ala Arg Val Ala Leu Leu Phe Glu Gly Arg Asp Ala Ala
                85                  90                  95

Gly Lys Gly Gly Thr Ile Lys Arg Phe Arg Glu Asn Leu Asn Pro Arg
            100                 105                 110

Gly Ala Arg Val Val Ala Leu Ser Lys Pro Thr Glu Ala Glu Arg Ser
        115                 120                 125
```

```
Gln Trp Tyr Phe Gln Arg Tyr Ile Gln His Leu Pro Ser Ala Gly Glu
            130                 135                 140

Leu Val Phe Tyr Asp Arg Ser Trp Tyr Asn Arg Gly Val Val Glu His
145                 150                 155                 160

Val Phe Gly Trp Cys Asp Glu Glu Gln Arg Glu Arg Phe Phe Arg Gln
                165                 170                 175

Val Met Pro Phe Glu His Asp Leu Val Asp Asp Gly Ile His Leu Phe
            180                 185                 190

Lys Phe Trp Leu Asn Val Gly Arg Ala Glu Gln Leu Arg Arg Phe His
            195                 200                 205

Asp Arg Glu Arg Asp Pro Leu Lys Gln Trp Lys Leu Ser Pro Val Asp
210                 215                 220

Ile Ala Gly Leu Asp Lys Trp Glu Ala Tyr Thr Thr Ala Ile Ser Gln
225                 230                 235                 240

Thr Leu Thr Arg Ser His Ser Asp Arg Ala Pro Trp Thr Val Ile Arg
                245                 250                 255

Ser Asp Asp Lys Lys Arg Ala Arg Leu Ala Ala Ile Arg Thr Val Leu
                260                 265                 270

Ser Gly Ile Asp Tyr Asp Asn Lys Asp Arg Ala Ala Val Gly Gln Pro
            275                 280                 285

Asp Ala Ala Ile Cys Gly Gly Pro Asp Ile Trp Asp Ala
290                 295                 300

<210> SEQ ID NO 7
<211> LENGTH: 175
<212> TYPE: PRT
<213> ORGANISM: Pasteurella multocida
<220> FEATURE:
<221> NAME/KEY: PEPTIDE
<222> LOCATION: (1)..(175)
<223> OTHER INFORMATION: Inorganic pyrophosphatase (PPA)

<400> SEQUENCE: 7

Met Gly Leu Glu Thr Val Pro Ala Gly Lys Ala Leu Pro Asp Asp Ile
1               5                   10                  15

Tyr Val Val Ile Glu Ile Pro Ala Asn Ser Asp Pro Ile Lys Tyr Glu
                20                  25                  30

Val Asp Lys Glu Ser Gly Ala Leu Phe Val Asp Arg Phe Met Ala Thr
            35                  40                  45

Ala Met Phe Tyr Pro Ala Asn Tyr Gly Tyr Val Asn Asn Thr Leu Ser
        50                  55                  60

Leu Asp Gly Asp Pro Val Asp Val Leu Val Pro Thr Pro Tyr Pro Leu
65                  70                  75                  80

Gln Pro Gly Ser Val Ile Arg Cys Arg Pro Val Gly Val Leu Lys Met
                85                  90                  95

Thr Asp Glu Ala Gly Ser Asp Ala Lys Val Val Ala Val Pro His Ser
            100                 105                 110

Lys Leu Thr Lys Glu Tyr Asp His Ile Lys Asp Val Asn Asp Leu Pro
        115                 120                 125

Ala Leu Leu Lys Ala Gln Ile Gln His Phe Phe Glu Ser Tyr Lys Ala
    130                 135                 140

Leu Glu Ala Gly Lys Trp Val Lys Val Asp Gly Trp Glu Gly Val Asp
145                 150                 155                 160

Ala Ala Arg Gln Glu Ile Leu Asp Ser Phe Glu Arg Ala Lys Lys
                165                 170                 175
```

```
<210> SEQ ID NO 8
<211> LENGTH: 505
<212> TYPE: PRT
<213> ORGANISM: Pseudomonas aeruginosa
<220> FEATURE:
<221> NAME/KEY: PEPTIDE
<222> LOCATION: (1)..(505)
<223> OTHER INFORMATION: Polyphosphate: AMP phosphotransferase (2D-PPK2)

<400> SEQUENCE: 8
```

Met Val Phe Glu Ser Ala Glu Val Gly His Ser Ile Asp Lys Asp Thr
1               5                   10                  15

Tyr Glu Lys Ala Val Ile Glu Leu Arg Glu Ala Leu Leu Glu Ala Gln
            20                  25                  30

Phe Glu Leu Lys Gln Gln Ala Arg Phe Pro Val Ile Ile Leu Ile Asn
        35                  40                  45

Gly Ile Glu Gly Ala Gly Lys Gly Glu Thr Val Lys Leu Leu Asn Glu
    50                  55                  60

Trp Met Asp Pro Arg Leu Ile Glu Val Gln Ser Phe Leu Arg Pro Ser
65                  70                  75                  80

Asp Glu Glu Leu Glu Arg Pro Pro Gln Trp Arg Phe Trp Arg Arg Leu
                85                  90                  95

Pro Pro Lys Gly Arg Thr Gly Ile Phe Phe Gly Asn Trp Tyr Ser Gln
            100                 105                 110

Met Leu Tyr Ala Arg Val Glu Gly His Ile Lys Glu Ala Lys Leu Asp
        115                 120                 125

Gln Ala Ile Asp Ala Ala Glu Arg Phe Glu Arg Met Leu Cys Asp Glu
    130                 135                 140

Gly Ala Leu Leu Phe Lys Phe Trp Phe His Leu Ser Lys Lys Gln Leu
145                 150                 155                 160

Lys Glu Arg Leu Lys Ala Leu Glu Lys Asp Pro Gln His Ser Trp Lys
                165                 170                 175

Leu Ser Pro Leu Asp Trp Lys Gln Ser Glu Val Tyr Asp Arg Phe Val
            180                 185                 190

His Tyr Gly Glu Arg Val Leu Arg Arg Thr Ser Arg Asp Tyr Ala Pro
        195                 200                 205

Trp Tyr Val Val Glu Gly Ala Asp Glu Arg Tyr Arg Ala Leu Thr Val
    210                 215                 220

Gly Arg Ile Leu Leu Glu Gly Leu Gln Ala Ala Leu Ala Thr Lys Glu
225                 230                 235                 240

Arg Ala Lys Arg Gln Pro His Ala Ala Pro Leu Val Ser Ser Leu Asp
                245                 250                 255

Asn Arg Gly Leu Leu Asp Ser Leu Asp Leu Gly Gln Tyr Leu Asp Lys
            260                 265                 270

Asp Ala Tyr Lys Glu Gln Leu Ala Ala Glu Gln Ala Arg Leu Ala Gly
        275                 280                 285

Leu Ile Arg Asp Lys Arg Phe Arg Gln His Ser Leu Val Ala Val Phe
    290                 295                 300

Glu Gly Asn Asp Ala Ala Gly Lys Gly Gly Ala Ile Arg Arg Val Thr
305                 310                 315                 320

Asp Ala Leu Asp Pro Arg Gln Tyr His Ile Val Pro Ile Ala Ala Pro
                325                 330                 335

Thr Glu Glu Glu Arg Ala Gln Pro Tyr Leu Trp Arg Phe Trp Arg His
            340                 345                 350

Ile Pro Ala Arg Arg Gln Phe Thr Ile Phe Asp Arg Ser Trp Tyr Gly
    355                 360                 365

Arg Val Leu Val Glu Arg Ile Glu Gly Phe Cys Ala Pro Ala Asp Trp
370                 375                 380

Leu Arg Ala Tyr Gly Glu Ile Asn Asp Phe Glu Glu Gln Leu Ser Glu
385                 390                 395                 400

Tyr Gly Ile Ile Val Val Lys Phe Trp Leu Ala Ile Asp Lys Gln Thr
                405                 410                 415

Gln Met Glu Arg Phe Lys Glu Arg Glu Lys Thr Pro Tyr Lys Arg Tyr
            420                 425                 430

Lys Ile Thr Glu Glu Asp Trp Arg Asn Arg Asp Lys Trp Asp Gln Tyr
        435                 440                 445

Val Asp Ala Val Gly Asp Met Val Asp Arg Thr Ser Thr Glu Ile Ala
    450                 455                 460

Pro Trp Thr Leu Val Glu Ala Asn Asp Lys Arg Phe Ala Arg Val Lys
465                 470                 475                 480

Val Leu Arg Thr Ile Asn Asp Ala Ile Glu Ala Ala Tyr Lys Lys Asp
                485                 490                 495

Lys Leu Glu His His His His His His
            500                 505

<210> SEQ ID NO 9
<211> LENGTH: 324
<212> TYPE: PRT
<213> ORGANISM: Pseudomonas aeruginosa
<220> FEATURE:
<221> NAME/KEY: PEPTIDE
<222> LOCATION: (1)..(324)
<223> OTHER INFORMATION: Polyphosphate:ADP phosphotransferase (1D-PPK2)

<400> SEQUENCE: 9

Met Gly Ser Ser His His His His His His Ser Ser Gly Leu Val Pro
1               5                   10                  15

Arg Gly Ser His Met Asp Ser Tyr Gly Asp Thr Ser Gly Arg Ile Gly
            20                  25                  30

Arg Asp Trp Leu Asp Arg His Asp Glu Leu Glu Gln Glu Leu Leu
        35                  40                  45

Asp Asp Glu Leu Asn Leu Asp Glu Leu Phe Gly Pro Glu Gln Glu Asp
    50                  55                  60

Ala Pro Gly Glu Leu Ser Arg Arg Tyr Phe Arg Glu Leu Phe Arg
65                  70                  75                  80

Leu Gln Arg Glu Leu Val Lys Leu Gln Asn Trp Val Val His Thr Gly
                85                  90                  95

His Lys Val Val Ile Leu Phe Glu Gly Arg Asp Ala Ala Gly Lys Gly
            100                 105                 110

Gly Val Ile Lys Arg Ile Thr Gln Arg Leu Asn Pro Arg Val Cys Arg
        115                 120                 125

Val Ala Ala Leu Pro Ala Pro Asn Asp Arg Glu Gln Thr Gln Trp Tyr
    130                 135                 140

Phe Gln Arg Tyr Val Ser His Leu Pro Ala Gly Gly Glu Ile Val Leu
145                 150                 155                 160

Phe Asp Arg Ser Trp Tyr Asn Arg Ala Gly Val Glu Arg Val Met Gly
                165                 170                 175

Phe Cys Asn Asp Glu Gln Tyr Glu Glu Phe Phe Arg Ser Val Pro Glu
            180                 185                 190

```
Phe Glu Lys Met Leu Ala Arg Ser Gly Ile Gln Leu Leu Lys Tyr Trp
        195                 200                 205

Phe Ser Ile Ser Asp Ala Glu Gln His Leu Arg Phe Leu Ser Arg Ile
        210                 215                 220

His Asp Pro Leu Lys Gln Trp Lys Leu Ser Pro Met Asp Leu Glu Ser
225                 230                 235                 240

Arg Arg Arg Trp Glu Ala Tyr Thr Lys Ala Lys Glu Thr Met Leu Glu
                245                 250                 255

Arg Thr His Ile Pro Glu Ala Pro Trp Trp Val Val Gln Ala Asp Asp
            260                 265                 270

Lys Lys Arg Ala Arg Leu Asn Cys Ile His His Leu Leu Gln Gln Met
        275                 280                 285

Pro Tyr Arg Glu Val Pro Gln Pro Pro Val His Leu Pro Glu Arg Leu
        290                 295                 300

Arg His Ala Asp Tyr Val Arg His Pro Thr Pro Gly Glu Ile Ile Val
305                 310                 315                 320

Pro Glu Val Tyr
```

ENZYMATIC METHOD FOR PREPARATION OF CMP-NEU5AC

The present application is the national phase entry of PCT Application No. PCT/EP2021/059101, filed Apr. 7, 2021, which claims priority to EP Application Serial No. 20168848.8, filed Apr. 8, 2020, both of which are incorporated by reference in their entireties.

REFERENCE TO SEQUENCE LISTING

The present application is filed with a Sequence Listing in Electronic format. The Sequence Listing is provided as a file entitled ABK001026APC.txt, created Oct. 7, 2022, which is approximately 24 kb in size. The information in the electronic format of the sequence listing is incorporated herein by reference in its entirety.

FIELD OF THE INVENTION

The present invention relates to a method for producing cytidine 5'-monophospho-N-acetyl-neuraminic acid (CMP-Neu5Ac, 1) from low-cost substrates N-acetyl-D-glucosamine (GlcNAc), pyruvate, cytidine and polyphosphate in a single reaction mixture with a set of enzymes comprising N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3). Further, said process may be adapted to produce Neu5Acylated, i.e. sialylated biomolecules and biomolecules including a saccharide, a peptide, a protein, a glycopeptide, a glycoprotein, a glycolipid, a glycan, an antibody, a glycoconjugate, in particular, an antibody drug conjugate, and a carbohydrate conjugate vaccine, or a flavonoid.

BACKGROUND OF THE INVENTION

N-acetylneuraminic acid (Neu5Ac) is a sialic acid and a nine-carbon (C-9) acidic monosaccharide that occurs naturally at the end of sugar chains attached to the surfaces of cells and soluble proteins. In the human body, the highest concentration of N-acetylneuraminic acid occurs in the brain where it participates as an integral part of ganglioside structure in synaptogenesis and neural transmission. Human milk also contains a high concentration of sialic acid attached to the terminal end of free oligosaccharides, in particular, galactosylceramide. In certain pathologies, e.g. in aggressive tumors of neuro-ectodemic origin, Neu5Ac is over-expressed on cell surface.

Certain strains of bacteria contain large amounts of N-acetylneuraminic acid in their capsular polysaccharide. For example, *Neisseria meningitidis* serogroup B capsular polysaccharide is a linear homopolymer of sialic acid consisting of approximately 200 repeated units of α(2-8)-linked N-acetyl neuraminic acid (Bhattacharjee A. K. et al., *J. Biol. Chem.* 1975, 250, pp. 1926-1932.) This homopolymer is not restricted to *N. meningitidis* serogroup B since it is also present in the capsule of *Escherichia coli* K1, a pathogen that causes meningitis in newborn children, in *Pasteurella haemolytica* A2, an important veterinary pathogen and also in *Moraxella non-liquefaciens*, a non-pathogenic microorganism common in nasal graves.

N-acetylneuraminic acid rarely occurs free in nature. They are more commonly present as components of oligosaccharide chains of mucins, glycoproteins, and glycolipids. They usually occupy terminal, non-reducing positions of oligosaccharide chains of complex carbohydrates on outer and inner membrane surfaces in various linkages, mainly to galactose, N-acetylgalactosamine, and other sialic acid moieties, where they are highly exposed and functionally important.

Cells from higher animals and various microorganisms produce sialic acid in a long pathway starting from glucose. Cytidine 5'-monophospho-N-acetyl-D-neurosaminic acid (CMP-Neu5Ac) is a key substrate for a large number of biotechnological applications.

CMP-Neu5Ac is a donor substrate for sialyltransferases which attach sialic acid to acceptor hydroxyl groups in various biopolymers including polysialic acids, glycolipids and glycoproteins (Tsuji, 1996).

Sialylated oligosaccharides, present on mammalian outer-cell surfaces, play vital roles in cellular interactions and some bacteria are able to mimic these structures to evade their host's immune system. It would be of great benefit to the study of infectious and autoimmune diseases and cancers, to understand the pathway of sialylation in detail to enable the design and production of inhibitors and mimetics. Sialylation occurs in two stages, the first is to activate sialic acid and the second is to transfer it to the target molecule. The activation step is catalyzed by the enzyme CMP-Neu5Ac synthetase (CSS, or CNS).

Since CMP-Neu5Ac is unstable and relatively expensive, the CMP-Neu5Ac synthetase is valuable for the preparative enzymatic synthesis of sialylated oligosaccharides. It can also be used to charge sialic acid analogs in order to synthesize the corresponding sialo-oligosaccharide analogs. Sialic acid activation has been reviewed by Kean (1991) and CMP-Neu5Ac synthetases have been isolated from various eukaryotic and prokaryotic sources. Several bacterial pathogens have been shown to possess sialylated capsular and lipo-polysaccharides as important virulence factors and this has motivated the study of sialic acid biosynthesis and incorporation in these organisms. *Neisseria meningitides* was shown to be a good source of CMP-Neu5Ac synthetase by Warren and Blacklow (1962) but a non-pathogenic recombinant strain would be preferable for the scale-up of the production of this enzyme and its application in preparative syntheses of sialylated oligosaccharides. Bacterial genes encoding CMP-Neu5Ac synthetase have been cloned from *Escherichia coli* (Vann et al., 1987), *Neisseria meningitides* (Edwards and Frosch, 1992, Ganguli et al., 1994), *Streptococcus agalactiae* (Haft et al., 1996) and *Haemophilus ducreyi* (Tullius et al., 1996).

CMP-Neu5Ac is needed for the production of carbohydrate vaccines and in the growing field of personalized medicine, i.e. preparation of glyconanomaterials for drug delivery. Moreover, in order to build the core structure of monoclonal antibodies and other recombinant proteins in vitro CMP-Neu5Ac is extensively needed.

Thus, there is a high demand to include Neu5Acylated i.e. sialylated biomolecules. However, in spite of the high demand for CMP-Neu5Ac (in the order of tons per year), the availability of CMP-Neu5Ac is very limited, even for researchers.

It is known that adenosine 5'-monophosphate (AMP) and adenosine 5'-triphosphate (ATP) in 10 mM concentration inhibit more than 60% of activity of certain N-acetylneuraminate cytidylyltransferases (CSSs). In the known methods, cytidyl nucleotides such as CMP, CDP, or CTP with a high concentration are directly provided into the enzymatic synthesis of CMP-Neu5Ac. However, such phosphorylated cytidines such as CMP, CDP, and CTP are known as inhibitor of N-acylneuraminate cytidylyltransferase (CSS)

as CSS is inhibited by cytidine nucleotides through binding to a second cytidyl binding site thereof (Ignacio G. BRAVO et. al., *Biochem. J,* 2001, 258, pp 568-598.)

It is reported that a very low concentration of cytidine 5'-monophosphate (CMP), and cytidine 5'-diphosphate (CDP) strongly inhibits activity of certain N-acetyl-neuraminate cytidylyltransferases (CSSs). For example, the activity of CSS from *Oncorhynchus mykiss* is inhibited 57% by 0.3 mM of CMP as well as 45% by CDP. The activity of CSS from *Pelophyls eschulenuts* is inhibited 43% by 1.0 mM of CMP as well as 49% by 1 mM of CDP. Also a high concentration (above 5 mM) of CTP inhibits the activity of CCS from *Cricetulus griseus,* and *Rattus norvegicus*. Thus, it is apparent that direct provision of a high concentration of CMP, CDP, and/or CTP is technically disadvantage for enzymatic production of the CMP-Neu5Ac.

In contrary, cytidine does not inhibit the activity of CSS with a high concentration (above 60 mM). Furthermore, ATP can be used as an activator of CCS (Ignacio G. BRAVO et. al., *Biochem. J.* 2001, 258, pp 568-598.)

Notwithstanding the aforementioned drawbacks of the CMP-Neu5Ac syntheses described in the literature, a further disadvantage of the general reaction of CMP-Neu5Ac is based on the fact that the starting materials, in particular the respective cytidine-5'-monophosphate (CMP) and cytidine-5'-triphosphate (CTP) are very expensive and thus the synthesis pathway results in a cost-intensive synthesis of CMP-Neu5Ac. As already described above, there is a need in the art to provide a cost effective and efficient method for preparation of CMP-Neu5Ac from low cost and readily available starting materials.

In order to provide a cost-effective and efficient method for the preparation of CMP-Neu5Ac, low-cost substrates such as N-acetyl-D-glucosamine (GlcNAc), pyruvate, cytidine and polyphosphate are identified as suitable starting materials for the production of CMP-Neu5Ac in a multi-enzymatic cascade reaction as depicted in FIG. 1A.

The reaction cascade of the present invention comprises (a) the formation of N-acetyl-D-mannosamine (ManNAc) from N-acetyl-D-glucosamine (GlcNAc), (b) the formation of N-acetyl-D-neuraminic acid (Neu5Ac) from ManNAc and pyruvate, (c) the formation of cytidine 5'-monophosphate (CMP) from cytidine and adenosine 5'-triphosphate (ATP), (d) the formation of cytidine 5'-diphosphate (CDP) from CMP and ATP, (e) the formation of cytidine 5'-triphosphate (CTP) from CDP and polyphosphate (PolyP$_n$), and (f) the reaction of Neu5Ac with CTP to CMP-Neu5Ac. Optionally, the cascade can be extended by adding a 1D-PPK2 to assist the conversion of ADP to ATP. Also, the cascade can be extended by adding a 2D-PPK2 in order to activate phosphorylation of AMP to ADP. Moreover, the cascade can be extended by adding a 1D-PPK2 and a 2DPPK2 in order to inhibit frequent hydrolysis of adenosine phosphates.

It was envisioned that CMP-Neu5Ac can be produced directly from N-acetyl-D-glucosamine (GlcNAc), pyruvate, cytidine and polyphosphate in the presence of N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3).

Most of all, to control the concentrations of CMP and CDP which inhibit strongly the catalytic activity of N-acylneuraminate cytidylyltransferase (CSS), CMP is in situ produced from cytidine in the presence of uridine kinase (UDK) and CDP is also continuously produced in situ from CMP by a uridine monophosphate (UMP) kinase.

Surprisingly, the inventors have found that in situ conversion of cytidine to a cytidine 5'-monophosphate (CMP) catalyzed by a uridine kinase (UDK) controls concentrations of phosphorylated cytidine nucleotides, in particular CMP, and CDP which inhibit a catalytic activity of N-acylneuraminate cytidylyltransferase (CSS). Furthermore, when a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3) is co-immobilized on a solid support, the efficacy of multi-enzymatic cascade reaction is enhanced.

There is a long-felt need for an efficient multi-enzymatic method of producing CMP-Neu5Ac in a cost-effective manner starting from low cost and readily available substrates.

Thus, it is the objective of the present invention to provide a cost-effective and efficient multi-enzymatic method for the preparation of CMP-Neu5Ac.

The objective of the present invention is solved by the teaching of the independent claims. Further advantageous features, aspects and details of the invention are evident from the dependent claims, the description, the figures, and the examples of the present application.

DESCRIPTION OF THE INVENTION

Thus, the present invention is directed to a method for producing cytidine 5'-monophospho-N-acetyl-neuraminic acid (CMP-Neu5Ac, 1)

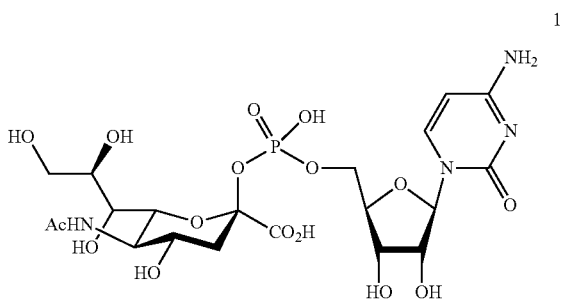

comprising:
A) providing a solution comprising N-acetyl-D-glucosamine, pyruvate, polyphosphate, cytidine, and adenosine 5'-triphosphate (ATP), and
  a set of enzymes comprising an N-acylglucosamine 2-epimerase (AGE), an N-acetylneuraminate lyase (NAL), an N-acetylneuraminate cytidylyltransferase (CSS), a uridine kinase (UDK), a uridine monophosphate kinase and a polyphosphate kinase 3 (PPK3);
B) mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine 5'-monophosphate (CMP).

A preferred embodiment of the present invention is directed to a method for producing cytidine 5'-monophospho-N-acetyl-neuraminic acid (CMP-Neu5Ac, 1)

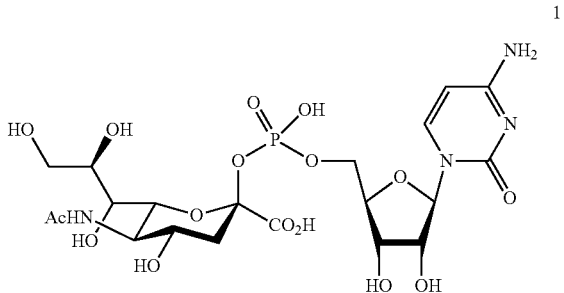

comprising:
A) providing a solution comprising N-acetyl-D-glucosamine, pyruvate, polyphosphate, cytidine, and adenosine 5'-triphosphate (ATP), and a set of enzymes comprising an N-acylglucosamine 2-epimerase (AGE), an N-acetylneuraminate lyase (NAL), an N-acetylneuraminate cytidylyltransferase (CSS), a uridine kinase (UDK), a uridine monophosphate kinase and a polyphosphate kinase 3 (PPK3);
B) mixing said solution and said set of enzymes and reacting a resulting solution to produce cytidine 5'-monophospho-N-acetyl-neuraminic acid (CMP-Neu5Ac),
wherein the set of enzymes or at least three enzymes of the set is/are co-immobilized on a solid support and the uridine kinase (UDK) transfers in situ the cytidine to a cytidine 5'-monophosphate (CMP).

Alternatively, N-acetyl-D-glucosamine (GlcNAc) is separately or in situ produced from D-glucosamine (GlcN) and acetate in the presence of N-acetyl-glucosamine deacetylase. Thus, in some cases, an additional step A1) may be performed separately before step A) as follows:
A1) producing N-acetyl-D-glucosamine from D-glucosamine (GlcN) and acetate in the presence of N-acetyl-glucosamine deacetylase.

In another cases, N-acetyl-D-glucosamine (GlcNAc) is in situ produced from D-glucosamine (GlcN) and acetate in the presence of N-acetyl-glucosamine deacetylase.

Thus, the present invention is directed to a method for producing cytidine 5'-monophospho-N-acetyl-neuraminic acid (CMP-Neu5Ac, 1)

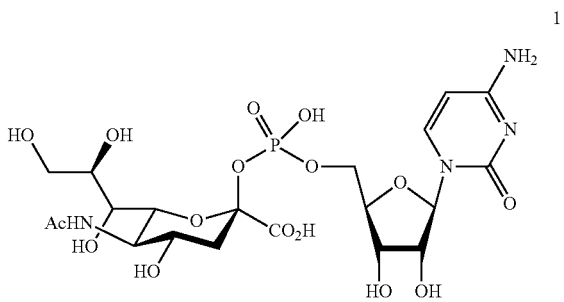

comprising:
A') providing a solution comprising D-glucosamine, acetate, pyruvate, polyphosphate, cytidine, and adenosine 5'-triphosphate (ATP), and a set of enzymes comprising an N-acylglucosamine deacetylase, an N-acyl-glucosamine 2-epimerase (AGE), an N-acetylneuraminate lyase (NAL), an N-acetylneuraminate cytidylyltransferase (CSS), a uridine kinase (UDK), a uridine monophosphate kinase and a polyphosphate kinase 3 (PPK3);
B') mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine 5'-monophosphate (CMP).

Preferably, the set of enzymes is co-immobilized on a solid support and more preferably the set of enzymes is co-immobilized on a reusable, mechanically stable solid support thereby increasing or retaining a large fraction of the activity of each enzyme.

Optionally, the set of enzymes further comprises an inorganic diphosphatase (PPA). Additionally, the set of enzymes further comprises a one-domain polyphosphate kinase 2 (1 D-PPK2) and/or a two-domain polyphosphate kinase 2 (2D-PPK2). The inorganic diphosphatase (PPA), the one-domain polyphosphate kinase 2 (1 DPPK2) and/or the two-domain polyphosphate kinase 2 (2DPPK2) are preferably also co-immobilized with the above-mentioned enzymes on the same solid support.

Preferably, in the method of the present invention, the resulting solution in the step B) has a pH value in a range of 5.0-10.0, preferred 5.5-9.5, more preferred 6.0-9.0, still more preferred 6.5-9.0, most preferred 7.0-9.0.

Preferably, in the method of the present invention, the concentration of N-acetyl-D-glucosamine (GlcNAc) is in the range of 10 mM to 3500 mM, preferred 20 mM to 3000 mM, more preferred 15 mM to 2500 mM, still more preferred 20 mM to 2000 mM, most preferred is in the range of 20 mM to 1000 mM;
and/or the concentration of the pyruvate is in the range of 10 mM to 3500 mM, preferred 20 mM to 3000 mM, more preferred 15 mM to 2500 mM, still more preferred 20 mM to 2000 mM, most preferred is in the range of 20 mM to 1000 mM;
and/or the concentration of the cytidine is in the range of 1 mM to 50 mM, preferred 1 mM to 40 mM, more preferred 1 mM to 30 mM, still more preferred 10 mM to 20 mM, most preferred is in the range of 1 mM to 15 mM;
and/or the concentration of adenosine 5'-triphosphate (ATP) is in the range of 0.001 mM to 10 mM, preferred 0.005 mM to 10 mM, more preferred 0.01 mM to 10 mM, still more preferred 0.05 mM to 10 mM, most preferred is in the range of 0.1 mM to 10 mM;
and/or the concentration of polyphosphate is in the range of 1 mM to 30 mM, preferred 1 mM to 25 mM, more preferred 1 mM to 20 mM, still more preferred 1 mM to 15 mM, most preferred is in the range of 1 mM to 10 mM.

Preferably, in the method of the present invention, the ratio of the N-acetyl-D-glucosamine and the cytidine is in the range of 1:1 to 100 to 1.

Preferably, in the method of the present invention, the resulting solution further comprises $Mg^{2+}$ with a concentration in the range of 0.1 mM to 500 mM, preferred 0.1 mM to 200 mM, more preferred 1 mM to 100 mM, still more preferred 10 mM to 100 mM, most preferred 20 mM to 50 mM.

Preferably, in the method of the present invention, each of the enzymes has the following amino acid sequence:
the N-acylglucosamine 2-epimerase (AGE) comprises an amino acid sequence as set forth in SEQ ID NO: 1;

the N-acetylneuraminate lyase (NAL) comprises an amino acid sequence as set forth in SEQ ID NO: 2;

the N-acylneuraminate cytidylyltransferase (CSS) comprises an amino acid sequence as set forth in SEQ ID NO: 3;

the uridine kinase (UDK) comprises an amino acid sequence as set forth in SEQ ID NO: 4;

the uridine monophosphate kinase (URA6) comprises an amino acid sequence as set forth in SEQ ID NO: 5;

the polyphosphate kinase 3 (PPK3) comprises an amino acid sequence as set forth in SEQ ID NO: 6; and the inorganic diphosphatase (PPA) comprises an amino acid sequence as set forth in SEQ ID NO: 7.

In particular, the solid support is composed of beads or resins comprising a polymer with epoxide functional groups, with amino epoxide functional groups, with ethylenediamine functional groups, with amino C2 functional groups, with amino C6 functional groups, with anionic/amino C6 spacer functional groups. The solid support is a porous or a non-porous particle including nanoparticle or a porous bead having a pore size of 0.1 Å to 100000 Å.

Preferably, the set of enzymes is directly co-immobilized on a solid support from cell lysate or cell homogenate.

The present invention also refers to a method for producing a Neu5Acylated i.e. sialylated biomolecule comprising i) performing the method as mentioned above to obtain CMP-Neu5Ac, ii) reacting the CMP-Neu5Ac obtained after step i) with a biomolecule, wherein the biomolecule is a saccharide, a glycopeptide, a glycoprotein, a glycolipid, a glycan, a peptide, a protein, an antibody, an antibody drug conjugate, a carbohydrate conjugate vaccine, or a flavonoid by forming an O-glycosidic bond with an hydroxyl group of the biomolecule with removal of CMP group in the presence of a sialyltransferase.

Preferably, the sialyltransferase is selected from beta-galactosamide alpha-2,6-sialyltransferase (EC 2.4.99.1), alpha-N-acetylgalactosaminide alpha-2,6-sialyltransferase (EC 2.4.99.3), beta-galactoside alpha-2,3-sialyltransferase (EC 2.4.99.4), N-acetyllactosaminide alpha-2,3-sialyltransferase (EC 2.4.99.6), alpha-N-acetyl-neuraminide alpha-2,8-sialyltransferase (EC 2.4.99.8); and lactosylceramide alpha-2,3-sialyltransferase (EC 2.4.99.9). These enzymes use CMP-Neu5Ac as a glycosyl donor.

Sialyltransferase may be responsible for the synthesis of the sequence Neu5Ac-α-2,3-Gal-β-1,3-GalNAc-, found on sugar chains O-linked to Thr or Ser and also as a terminal sequence on certain gangliosides. These enzymes catalyze sialyltransfer reactions during glycosylation, and are type II membrane proteins.

Therefore, preferably, the biomolecule contains any one of the moieties as terminal end group selected from galactoside (Gal), galactosamininde (GalN), N-acetylgalactosaminide (GalNAc), neuraminide (Neu), N-acetyl neuraminide (Neu5Ac), N-glycolylneuraminide, 3-Deoxy-D-glycero-D-galacto-2-nonulosonic Acid (KDN), and N-acetyllacosaminide (Gal-β-1-3-GlcNAc).

More preferred, the biomolecule is glycopeptide, glycoprotein, or antitumor vaccine which comprises T-antigen (Gal-β-1-3-GalNAc-α-1-O—) or Tn-antigen (GalNAc-α-1-O—); or a glycolipid comprising Gal-β-1-4-GlcNAc-β-1-O—.

The present invention is also directed to a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate (UMP) kinase and a polyphosphate kinase 3 (PPK3), wherein the set of enzymes is immobilized or co-immobilized on a polymer through covalent bonds.

Preferably the set of enzymes comprises an N-acylglucosamine 2-epimerase (AGE), an N-acetyl-neuraminate lyase (NAL), an N-acylneuraminate cytidylyltransferase (CSS), a uridine kinase (UDK), a uridine monophosphate (UMP) kinase and a polyphosphate kinase 3 (PPK3), wherein the set of enzymes is preferably co-immobilized on a polymer functionalized with epoxy groups.

Preferably, the set of enzymes of the present invention further comprises an inorganic diphosphatase (PPA), a one-domain polyphosphate kinase 2 (1D-PPK2) and/or a two-domain polyphosphate kinase 2 (2D-PPK2).

DETAILED DESCRIPTION OF THE INVENTION

Definitions

As used herein, the term "N-acylglucosamine 2-epimerase (GlcNAc 2-epimerase, ACE)" refers to an enzyme having an active domain that catalyzes the epimerization of N-acyl-D-glucosamine to N-acyl-D-mannosamine as follows:

N-acyl-D-glucosamine N-acyl-D-mannosamine

Hence, this enzyme has one substrate, N-acyl-D-glucosamine, and one product, N-acyl-D-mannosamine. This enzyme belongs to the family of isomerases, specifically to those racemases and epimerases acting on carbohydrates and derivatives.

The N-acylglucosamine 2-epimerase belongs to the EC class 5.1.3.8. The N-acyl-glucosamine 2-epimerase has also the following synonyms: N-acyl-D-glucosamine 2-epimerase, acylglucosamine 2-epimerase, and N-acetylglucosamine 2-epimerase. This enzyme participates in amino-sugar metabolism. It employs one cofactor, ATP.

As used herein, the term "N-acetylglucosamine deacetylase" refers to an enzyme having an active domain catalyzing the following reaction:

N-acetyl-D-glucosamine+H₂O D-glucosamine+acetate

This enzymatic reaction is reversible and thus in this invention, the N-acetylglucosamine deacetylase is used for producing N-acetyl-D-glucosamine (GlcNAc) by pushing the equilibrium to production of GlcNAc. Therefore, in the present invention this enzyme uses two substrates D-glucosamine and acetate for producing N-acetyl-D-glucosamine.

This enzyme belongs to the family of hydrolases, those acting on carbon-nitrogen bonds other than peptide bonds, specifically in linear amides. The N-acetylglucosamine deacetylase belongs to the EC class EC 3.5.1.33. The N-acetylglucosamine deacetylase has also the following synonyms: N-acetyl-D-glucosamine amidohydrolase, acetylaminodeoxyglucose acetylhydrolase, and N-acetyl-D-glucosaminyl N-deacetylase.

As used herein, the term "N-acetylneuraminate lyase (NAL)" refers to a polypeptide having active domain catalyzing the following reaction:

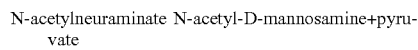
N-acetylneuraminate N-acetyl-D-mannosamine+pyruvate

This enzymatic reaction is reversible and thus in this invention, the N-acetylneuraminase lyase is used for producing CMP-Neu5Ac by pushing the equilibrium to production of Neu5Ac. Therefore, in the present invention this enzyme uses two substrates N-acetyl-D-mannosamine and pyruvate for producing N-acetylneuraminate.

This enzyme belongs to the family of lyases, specifically the oxo-acid-lyases, which cleave carbon-carbon bonds. The N-acetylneuraminate lyase belongs to the EC class EC 4.1.3.3. The N-acetylneuraminate lyase has also the following synonyms: N-acetylneuraminate pyruvate-lyase (N-acetyl-D-mannosamine-forming). Other names in common use include N-acetylneuraminic acid aldolase, acetylneuraminate lyase, sialic aldolase, sialic acid aldolase, sialate lyase, N-acetylneuraminic aldolase, neuraminic aldolase, N-acetylneuraminate aldolase, neuraminic acid aldolase, N-acetylneuraminic acid aldolase, neuraminate aldolase, N-acetylneuraminic lyase, N-acetylneuraminic acid lyase, NPL, NALase, NANA lyase, acetylneuraminate pyruvate-lyase, and N-acetylneuraminate pyruvate-lyase. This enzyme participates in aminosugar metabolism.

As used herein, the term "N-acylneuraminate cytidylyltransferase (CSS)" refers to a polypeptide having an active domain catalyzing the reaction of cytidine 5'-triphosphate (CTP) with N-acetyl-D-neuraminic acid and producing CMP-N-acetyl-D-neuraminic acid (CMP-Neu5Ac).

The N-acylneuraminate cytidylyltransferase has also the following synonyms: CMP-sialate pyrophosphorylase, CMP-sialate synthase, cytidine 5'-monophosphosialic acid synthetase, CMP-Neu5Ac synthetase (CNS), CMP-NeuAc synthetase, acylneuraminate cytidyltransferase, CMP-N-acetylneuraminate synthetase, CMP-N-acetylneuraminate synthase, CMP-N-acetylneuraminic acid synthase, CMP-NANA synthetase, CMP-sialate synthetase, CMP-sialic synthetase, cytidine 5'-monophospho-N-acetylneuraminic acid synthetase, cytidine 5'-monophosphate N-acetylneuraminic acid synthetase, cytidine monophosphosialic acid synthetase, cytidine monophosphoacetylneuraminic synthetase, cytidine monophosphosialate pyrophosphorylase, cytidine monophosphosialate synthetase, and acetylneuraminate cytidylyltransferase.

The N-acylneuraminate cytidylyltransferase belongs to the EC class 2.7.7.43. The N-acylneuraminate cytidylyltransferase catalyzes the following reaction:

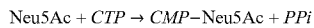

N-acylneuraminate cytidylyltransferase is obtained from microorganisms including *Cricetulus griseus, Escherichia coli, Haemophilus ducreyi, Haemophilus influenza, Hungateiclostridium thermocellum, Mannheimia haemolytica, Neisseria meningitidis, Oncorhynchus mykiss, Pasteurella haemolytica A2, Pelophylax esculentus, Photobacterium leiognathi, Rattus norvegicus, Streptococcus agalactiae,* and *Sus scrofa*; mouse, rat, calf and rainbow trout.

Mutants of *Neisseria meningitidis* CSS have at least one of the following mutations: Q104A, R165A, Q166A, N175A, Y179A, F192A, F193A.

Kinases are enzymes which form a part of the family of the phosphotransferases. Kinases are enzymes that catalyze the transfer of phosphate groups from high-energy, phosphate-donating molecules to specific substrates. This process is known as phosphorylation, where the substrate gains a phosphate group and the high-energy nucleotide, e.g. adenosine triphosphate (ATP), molecule donates a phosphate group. This transesterification produces a phosphorylated substrate and ADP.

As used herein, the term "uridine kinase" refers to a polypeptide having an active domain catalyzing the reaction of uridine to uridine 5'-monophosphate in the presence of adenosine triphosphate (ATP) as follows:

$$\text{ATP+uridine} \leftrightarrow \text{ADP+UMP}$$

Thus, the two substrates of this enzyme are ATP and uridine, whereas its two products are ADP and UMP.

In addition, it was found that the uridine kinase is able to catalyze the reaction of cytidine to cytidine 5'-monophosphate in the presence of adenosine triphosphate as follows:

$$\text{Cytidine+ATP} \rightleftharpoons \text{CMP+ADP}$$

This enzyme belongs to the family of transferases, specifically those transferring phosphorus-containing groups (phosphotransferases) with an alcohol group as acceptor. The uridine kinase belongs to the EC class 2.7.1.48. Other names in common use include pyrimidine ribonucleoside kinase, uridine-cytidine kinase, uridine kinase (phosphorylating), and uridine phosphokinase. This enzyme participates in pyrimidine metabolism.

As used herein, the term "uridine monophosphate (UMP) kinase" or refers to a polypeptide having an active domain catalyzing the reaction of uridine 5'-monophosphate to uridine 5'-diphosphate in the presence of adenosine triphosphate. The uridine monophosphate kinase belongs to the EC class 2.7.4.22. The uridine monophosphate kinase catalyzes the following reaction:

$$\text{UMP+ATP} \rightleftharpoons \text{UDP+ADP}$$

In addition, it was found that the uridine monophosphate (UMP) kinase is able to catalyze the reaction of cytidine monophosphate to cytidine 5'-diphosphate in the presence of adenosine triphosphate as follows:

$$\text{CMP+ATP} \rightleftharpoons \text{CDP+ADP}$$

This enzyme belongs to the family of transferases, specifically those transferring phosphorus-containing groups (phosphotransferases) with a phosphate group as acceptor. Other names in common use include uridylate kinase, UMPK, uridine monophosphate kinase, PyrH, UMP-kinase, and SmbA. This enzyme participates in pyrimidine metabolism.

As used herein, the term "polyphosphate" refers to any salts containing several P—O—P bonds generated by corner sharing of six or more phosphate ($PO_4$) tetrahedral, leading to the formation of long chains. The term "$PolyP_n$" is synonymously used, wherein n represents average chain length of the number of phosphate residues, e.g. $PolyP_{25}$ refers to a polyphosphate having about 25 phosphate residues and $PolyP_{14}$ refers to a polyphosphate having about 14 phosphate residues.

As used herein, the term "polyphosphate kinase" refers to a polypeptide having polyphosphate kinase activity, i.e. a polyphosphate kinase catalyzes the following reactions:

$$\text{NMP+polyphosphate }(n+1) \rightleftharpoons \text{NDP+polyphosphate }(n)$$

$$\text{NDP+polyphosphate }(n+1) \rightleftharpoons \text{NTP+polyphosphate}(n)$$

with N being a nucleotide such as guanosine, adenosine, uridine etc. and NMP being nucleoside monophosphate, NDP being nucleoside diphosphate and NTP being nucleoside triphosphate.

In case of uridine the polyphosphate kinase catalyzes the following reaction:

$$\text{ADP+polyphosphate }(n+1) \rightleftharpoons \text{ATP+polyphosphate}(n)$$

$$\text{AMP+polyphosphate }(n+1) \rightleftharpoons \text{ADP+polyphosphate }(n)$$

$$\text{UDP+polyphosphate }(n+1) \rightleftharpoons \text{UTP+polyphosphate}(n)$$

The polyphosphate kinase belongs to the EC class 2.7.4.1. Representatives of the polyphosphate kinase enzyme used in the inventive methods described herein include but are not limited to polyphosphate kinase 1 (PPK1), polyphosphate kinase 2 (PPK2), 2-domain polyphosphate kinase 2 (2D-PPK2) and 1-domain polyphosphate kinase 2 (1D-PPK2) and polyphosphate kinase 3 (PPK3).

As used herein, the term "pyrophosphatase" refers to a polypeptide having pyrophosphatase activity, i.e. a polypeptide that catalyzes the following reaction:

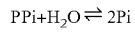

wherein PPi refers to pyrophosphate and Pi to phosphate.

The pyrophosphatase belongs to EC classes 3.6.1.1. In this context, the term "diphosphatase" refers to a pyrophosphatase polypeptide which catalyzes the hydrolysis of diphosphate to phosphate.

As used herein, the term "sialyltransferase" is an enzyme of the GT family that play an integral role in the biosynthesis of Neu5Ac containing oligosaccharides and glycoconjugates. Generally in glycosylation reactions catalyzed by STs, the sugar nucleotide donor is cytidine 5'-monophosphate Neu5Ac (CMP-Neu5Ac), and the acceptor is an oligosaccharide or glycoconjugate terminated by a galactose (Gal), N-acetylgalactosamine (GalNAc), or other Neu5Ac residue. STs are classified based on the position of the glycosyl acceptor that Neu5Ac is transferred to. In humans, these are ST3, ST6, and ST8, which form an α-glycosidic bond between the C2 atom of Neu5Ac and the 3'-, 6'-, or 8'-hydroxyl group of the acceptor, respectively. Preferably, "sialyltransferase" is selected from beta-galactosamide alpha-2,6-sialyltransferase (EC 2.4.99.1), alpha-N-acetylgalactosaminide alpha-2,6-sialyltransferase (EC 2.4.99.3), beta-galactoside alpha-2,3-sialyltransferase (EC 2.4.99.4), N-acetyllactosaminide alpha-2,3-sialyltransferase (EC 2.4.99.6), alpha-N-acetyl-neuraminide alpha-2,8-sialyltransferase (EC 2.4.99.8); and lactosylceramide alpha-2,3-sialyltransferase (EC 2.4.99.9). These enzymes use the CMP-Neu5Ac as a glycosyl donor.

As used herein, "saccharide" refers to but not restricted to monosaccharide, disaccharide, trisaccharide, tetrasaccharide, pentasaccharide, hexasaccharide, heptasaccharide, octasaccharide, oligosaccharide, glycan and polysaccharide.

The saccharide comprises preferably at least one of monosaccharide units selected from:

D-Arabinose, D-Lyxose, D-Ribose, D-Xylose, L-Arabinose, L-Lyxose, L-Ribose, L-Xylose, D-Ribulose, D-Xylulose, L-Ribulose, L-Xylulose, D-Deoxyribose, L-Deoxyribose, D-Erythrose, D-Threose, L-glycero-D-manno-Heptose, D-glycero-D-manno-Heptose, D-Allose, D-Altrose, D-Glucose, D-Mannose, D-Gulose, D-Idose, D-Galactose, D-Talose, D-psicose, D-fructose, D-sorbose, D-tagatose, 6-Deoxy-L-altrose, 6-Deoxy-D-talose, D-Fucose, L-Fucose, D-Rhamnose, L-Rhamnose, D-Quinovose, Olivose, Tyvelose, Ascarylose, Abequose, Paratose, Digitoxose, Colitose, D-Glucosamine, D-Galactosamine, D-Mannosamine, D-Allosamine, I-Altrosamine, D-Gulosamine, L-Idosamine, D-Talosamine, N-Acetyl-d-glucosamine, N-Acetyl-D-galactosamine, N-Acetyl-D-mannosamine, N-Acetyl-D-allosamine, N-Acetyl-L-altrosamine, N-Acetyl-D-gulosamine, N-Acetyl-L-idosamine, N-Acetyl-D-talosamine, N-Acetyl-D-fucosamine, N-Acetyl-L-fucosamine, N-Acetyl-L-rhamnosamine, N-Acetyl-D-quinovosamine, D-Glucuronic acid, D-Galacturonic acid, D-Mannuronic acid, D-Alluronic acid, L-Altruronic acid, D-Guluronic acid, L-Guluronic acid, L-Iduronic acid, D-Taluronic acid, Neuraminic acid, N-Acetylneuraminic acid, N-Glycolylneuraminic acid, 3-Deoxy-D-manno-octulosonic Acid (KDO), 3-Deoxy-D-glycero-D-galacto-2-nonulosonic Acid (KDN), Apiose, Bacillosamine, Thevetose, Acofriose, Cymarose, Muramic acid, N-Acetylmuramic acid, N-Glycolylmuramic acid, 3-Deoxy-lyxo-heptulosaric acid, Ketodeoxyoctonic acid, and Ketodeoxynononic acid. Preferably the monosaccharide or monosaccharide unit belongs to the following group of α- and β-D/L-carbohydrates comprising or consisting of:

α-D-ribopyranose, α-D-arabinopyranose, α-D-xylopyranose, α-D-lyxopyranose, α-D-allopyranose, α-D-altropyranose, α-D-glucopyranose, α-D-mannopyranose, α-D-glucopyranose, α-D-idopyranose, α-D-galactopyranose, α-D-talopyranose, α-D-psicopyranose, α-D-fructopyranose, α-D-sorbopyranose, α-D-tagatopyranose, α-D-ribofuranose, α-D-arabinofuranose, α-D-xylofuranose, α-D-lyxofuranose, α-D-Allofuranose, α-D-Altrofuranose, α-D-Glucofuranose, α-D-Mannofuranose, α-D-gulofuranose, α-D-idofuranose, α-D-galactofuranose, α-D-talofuranose, α-D-psicofuranose, α-D-fructofuranose, α-D-sorbofuranose, α-D-tagatofuranose, α-D-xylulofuranose, α-D-ribulofuranose, α-D-threofuranose, α-D-rhamnopyranose, α-D-erythrofuranose, α-D-glucosamine, α-D-N-acetyl-glucosamine, α-D-glucopyranuronic acid, α-D-galactosamine, α-D-N-acetyl-galactosamine, α-D-mannosamine, α-D-N-acetyl-mannosamine, α-D-neuraminic acid, α-D-N-acetylneuraminic acid, α-D-N-Glycolylneuraminic acid, α-3-Deoxy-D-manno-octulosonic acid (KDO), α-3-Deoxy-D-glycero-D-galacto-2-nonulosonic Acid (KDN), β-D-ribopyranose, β-D-arabinopyranose, β-D-xylopyranose, β-D-lyxopyranose, β-D-allopyranose, β-D-altropyranose, β-D-glucopyranose, β-D-mannopyranose, β-D-glucopyranose, β-D-idopyranose, β-D-galactopyranose, β-D-talopyranose, β-D-psicopyranose, β-D-fructopyranose, β-D-sorbopyranose, β-D-tagatopyranose, β-D-ribofuranose, β-D-arabinofuranose, β-D-xylofuranose, β-D-lyxofuranose, β-D-rhamnopyranose, β-D-allofuranose, β-D-altrofuranose, β-D-glucofuranose, β-D-mannofuranose, β-D-gulofuranose, β-D-idofuranose, β-D-galactofuranose, β-D-talofuranose, β-D-psicofuranose, β-D-fructofuranose, β-D-sorbofuranose, β-D-tagatofuranose, β-D-xylulofuranose, β-D-ribulofuranose, β-D-threofuranose, β-D-erythrofuranose, β-D-glucosamine, β-D-N-acetyl-glucosamine, β-D-glucopyranuronic acid, β-D-galactosamine, β-D-N-acetyl-galactosamine, β-D-mannosamine, β-D-N-acetyl-mannosamine, β-D-neuraminic acid, β-D-N-acetylneuraminic acid, β-D-N-glycolylneuraminic acid, β-3-Deoxy-D-manno-octulosonic acid (KDO), β-3-Deoxy-D-glycero-D-galacto-2-nonulosonic Acid (KDN), α-L-ribopyranose, α-L-arabinopyranose, α-L-xylopyranose, α-L-lyxopyranose, α-L-allopyranose, α-L-altropyranose, α-L-glucopyranose, α-L-mannpyranose, α-L-glucopyranose, α-L-idopyranose, α-L-galactopyranose, α-L-talopyranose, α-L-psicopyranose, α-L-fructopyranose, α-L-sorbopyranose, α-L-tagatopyranose, α-L-rhamnopyranose, α-L-ribofuranose, α-L-arabinofuranose, α-L-xylofuranose, α-L-lyxofuranose, α-L-Allofuranose, α-L-Altrofuranose, α-L-Glucofuranose, α-L-Mannofuranose, α-L-gulofuranose, α-L-idofuranose, α-L-galactofuranose, α-L-talofuranose, α-L-psicofuranose, α-L-fructofuranose, α-L-sorbofuranose, α-L-tagatofuranose, α-L-xylulofuranose, α-L-ribulofuranose, α-L-threofuranose, α-L-erythrofuranose, α-L-glucosamine, α-L-glucopyranuronic acid, β-L-ribopyranose, β-L-arabinopyranose, β-L-xylopyranose, β-L-lyxopyranose, β-L-allopyranose, β-L-altropyranose, β-L-glucopyranose, β-L-mannpyranose, β-L-glucopyranose, β-L-idopyranose, β-L-galactopyranose, β-L-taloopyranose, β-L-psicopyranose, β-L-fructopyranose, β-L-sorbopyranose, β-L-tagatopyranose, β-L-ribofuranose, β-L-arabinofuranose, β-L-xylofuranose, β-L-lyxofuranose, β-L-allofuranose, β-L-altrofuranose, β-L-glucofuranose, β-L-mannofuranose, β-L-gulofuranose, β-L-idofuranose, β-L-galactofuranose, β-L-talofuranose, β-L-psicofuranose, β-L-fructofuranose, β-L-sorbofuranose, β-L-tagatofuranose, β-L-xylulofuranose, β-L-ribulofuranose, β-L-threofuranose, β-L-erythrofuranose, β-L-glucosamine, β-L-glucopyranuronic acid, and β-L-rhamnopyranose.

The saccharides are further optionally modified to carry amide, carbonate, carbamate, carbonyl, thiocarbonyl, carboxy, thiocarboxy, ester, thioester, ether, epoxy, hydroxyalkyl, alkylenyl, phenylene, alkenyl, imino, imide, isourea, thiocarbamate, thiourea and/or urea moieties.

Preferably, "saccharide" is a human milk oligosaccharide including lactose, N-acetyl-lactosamine, lacto-N-biose, 2'-fucosyllactose, 3-fucosyllactose (3-FL), lacto-N-tetraose (LNT), lacto-N-neotetraose (LNnT), difucosyllactose (DiFL), lacto-N-triose II (LNT-II), lacto-N-fucopentaose I (LNFP I), lacto-N-fucopentaose III (LNFP III), lacto-N-fucopentaose V (LNFPV).

As used herein, the term "glycopeptide" refers to a peptide that contains carbohydrate moieties covalently attached to the side chains of the amino acid residues that constitute the peptide. The carbohydrate moieties form side chains and are either O-glycosidic connected to the hydroxy group of a serine or threonine residue or N-glycosidic connected to the amido nitrogen of an asparagine residue.

As used herein, the term "glycoprotein" refers to a polypeptide that contains carbohydrate moieties covalently attached to the side chains of the amino acid residues that constitute the polypeptide. The carbohydrate moieties form side chains and are either O-glycosidic connected to the hydroxy group of a serine or threonine residue or N-glycosidic connected to the amido nitrogen of an asparagine residue.

As used herein, the term "glycolipid" refers to a compound containing one or more monosaccharide moieties bound by a glycosidic linkage to a hydrophobic moiety. Glycolipids consist of monoglycosyldiacylglycerol (MGDG), diglycosyldiacylglycerol (DGDG), trimethyl-beta-alaninediacylglycerol, and sulphaquinovosyldiacylglycerol. Different glycolipid classes exist having various possible backbone molecular structures such as acylglycerols, sphingoids, ceramides (N-acylsphingoids), and sterols.

In particular, a ganglioside is a molecule composed of a glycosphingolipid (ceramide and oligosaccharide) with one or more N-acetylneuraminic acid, Neu5Ac) linked on the sugar chain. Types of ganglioside includes LM1, GM1, GM1b, and GM2 which comprise one N-acetylneuraminic acid; GD1a, GalNAc-GD1a, GD1b, GD2, and GD3 which comprise two N-acetylneuraminic acids; GT1a, and GT3 which comprise three N-acetylneuraminic acids; and GQ1b which comprises four N-acetylneuraminic acids.

As used herein, the term "protein" refers to a polypeptide that contains or lacks of carbohydrate moieties covalently attached to the side chains of the amino acid residues that constitute the polypeptide including aglycosylated proteins and glycosylated proteins.

As used herein, the term "peptide" refers to a peptide that contains or lacks of carbohydrate moieties covalently attached to the side chains of the amino acid residues that constitute the peptide, including aglycosylated peptides and glycosylated peptides.

As used herein, the term "bioconjugate" refers to a molecular construct consisting of at least two molecules which are covalently bound to each other and wherein at least one of which is a biomolecule, i.e. a molecule present in organisms that are essential to one or more typically biological processes. Exemplarily bioconjugates are carbohydrate conjugate vaccines consisting of a carbohydrate antigen covalently coupled to a carrier protein, and antibody drug conjugates.

As used herein, the term "carbohydrate conjugate vaccine" refers to a conjugate containing a carbohydrate antigen covalently bound to an immunogenic carrier. The carbohydrate antigen can be, but is not limited to, a bacterial capsular saccharide, a saccharide of a viral glycoprotein, a saccharide antigen of sporozoa or parasites, a saccharide antigen of pathogenic fungi, or a saccharide antigen which is specific to cancer cells. The immunogenic carrier can be, but is not limited to, a carrier protein selected from toxoids, including tetanus toxoid (TT), diphtheria toxoid (DT), cross-reaction material 197 ($CRM_{197}$), protein D of non-typeable *H. influenzae*, outer membrane protein complexes of *Neisseria meningitidis* capsular group B (OMPCs), exotoxin A of *P. aeruginosa* (EPA), *C. difficile* toxin A (CDTA), pneumococcal proteins, such as pneumococcal surface protein A (PspA), pneumococcal histidine triad D (PhtD), detoxified pneumolysin (dPly), and spr96/2021, *S. aureus* α toxin and Shiga toxin 1 b.

The term "solid support" as used herein refers to an insoluble, functionalized, material to which enzymes or other reagents may be attached or immobilized, directly or via a linker bearing an anchoring group, allowing enzymes to be readily separated (by washing, filtration, centrifugation, etc.) from excess reagents, soluble reaction products, by-products, or solvents. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. A solid support can also consist of magnetic particles. For an overview of suitable support materials for enzyme immobilization see Zdarta et al. *Catalysts* 2018, 8, 92, and Datta et al. Biotech 2013 3:1-9.

The configuration of a solid support can be in the form of beads, monoliths, spheres, particles, a particle bed, a fiber mat, granules, a gel, a membrane, a hollow-fiber membrane, a mixed-matrix membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location.

Thus, the present invention is directed to a method for producing cytidine 5'-monophospho-N-acetyl-neuraminic acid (CMP-Neu5Ac, 1)

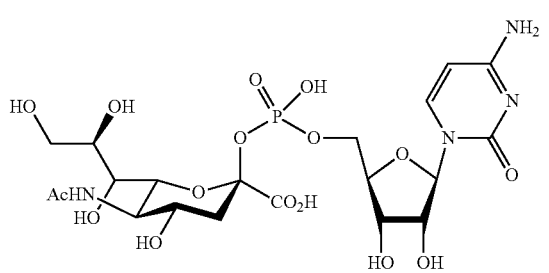

comprising:
A) providing a solution comprising N-acetyl-D-glucosamine, pyruvate, polyphosphate, cytidine, and adenosine 5'-triphosphate (ATP), and a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);
B) mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine monophosphate (CMP).

In a preferred embodiment the set of enzymes is co-immobilized on a solid support as disclosed herein.

Reworded, the present invention is directed to a method for producing cytidine 5'-monophospho-N-acetyl-neuraminic acid (CMP-Neu5Ac, 1)

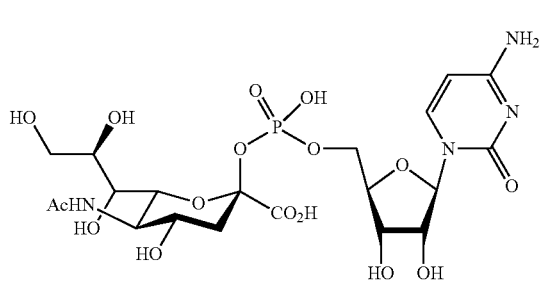

comprising:
A) providing a solution comprising N-acetyl-D-glucosamine, pyruvate, polyphosphate, cytidine, and adenosine 5'-triphosphate (ATP), and a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);
B) mixing said solution and said set of enzymes and reacting a resulting mixture to produce cytidine 5'-monophospho-N-acetyl-neuraminic acid (CMP-Neu5Ac),
wherein the uridine kinase (UDK) transfers in situ the cytidine to a cytidine monophosphate (CMP).

In the inventive method, CMP, CDP as well was CTP are formed in situ from cytidine (see below). Preferably, the set of enzymes is co-immobilized on a solid support.

In alternative words, the present invention is directed to a method for producing cytidine 5'-monophospho-N-acetyl-neuraminic acid (CMP-Neu5Ac, 1)

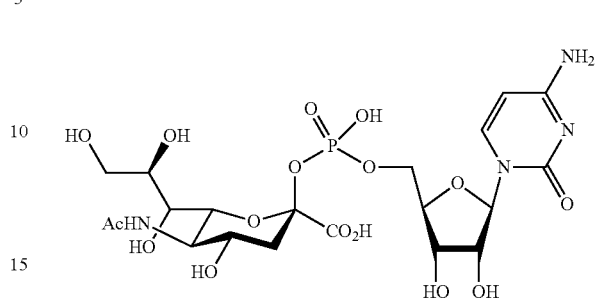

comprising:
A) providing a solution comprising N-acetyl-D-glucosamine, pyruvate, polyphosphate, cytidine, and adenosine 5'-triphosphate (ATP), and a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);
B) mixing said solution and said set of enzymes and reacting a resulting mixture to produce cytidine 5'-monophospho-N-acetyl-neuraminic acid (CMP-Neu5Ac),
wherein in step B) CMP, CDP as well was CTP are formed in situ and the uridine kinase (UDK) transfers in situ the cytidine to a cytidine monophosphate (CMP).

Preferably, the set of enzymes is co-immobilized on a solid support. Surprisingly, the co-immobilization of the set of enzymes strongly enhances the efficiency of the enzymatic cascade reaction compared to the process with non-immobilized enzymes and to the process with separately immobilized enzymes on different solid supports.

Preferably, the set of enzymes is co-immobilized on a reusable, mechanically stable solid support thereby increasing or retaining a large fraction of the activity of each enzyme.

In the step B), during the reaction of a resulting solution to produce cytidine 5'-monophospho-N-acetyl-neuraminic acid (CMP-Neu5Ac) in the presence of the set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3), the following cascade reactions are performed:
(a) formation of N-acetyl-D-mannosamine (ManNAc) from N-acetyl-D-glucosamine (GlcNAc) being catalyzed by the N-acylglucosamine 2-epimerase (AGE),
(b) formation of N-acetyl-D-neuraminic acid (Neu5Ac) from ManNAc and pyruvate being catalyzed by the N-acetylneuraminate lyase (NAL),
(c) formation of cytidine 5'-monophosphate (CMP) from cytidine and adenosine 5'-triphosphate (ATP) being catalyzed by the uridine kinase (UDK),
(d) formation of cytidine 5'-diphosphate (CDP) from cytidine 5'-monophosphate (CMP) and adenosine 5'-triphosphate (ATP) being catalyzed by the uridine monophosphate kinase,
(e) formation of cytidine 5'-triphosphate (CTP) from cytidine 5'-diphosphate (CDP) and polyphosphate being catalyzed by polyphosphate kinase 3 (PPK3);

(e') regeneration of adenosine 5'-triphosphate (ATP) from adenosine 5'-diphosphate (ADP) produced in the steps (c) and (d) and polyphosphate being catalyzed by polyphosphate kinase 3 (PPK3); and
(f) formation of cytidine 5'-monophospho-N-acetyl-neuraminic acid (CMP-Neu5Ac) by the reaction of N-acetyl-D-neuraminic acid (Neu5Ac) with cytidine 5'-triphosphate (CTP) being catalyzed by the N-acyl-neuraminate cytidylyltransferase (CSS).

Therefore, the present invention refers to a method for producing cytidine 5'-monophospho-N-acetyl-neuraminic acid (CMP-Neu5Ac, 1)

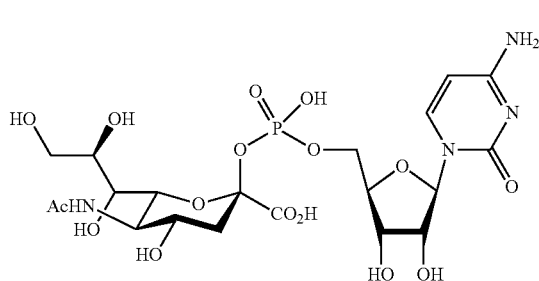

comprising:
A) providing a solution comprising N-acetyl-D-glucosamine, pyruvate, polyphosphate, cytidine, and adenosine 5'-triphosphate (ATP), and
a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);
B) mixing said solution and said set of enzymes and reacting a resulting solution to produce cytidine 5'-monophospho-N-acetyl-neuraminic acid (CMP-Neu5Ac) by
(a) formation of N-acetyl-D-mannosamine (ManNAc) from N-acetyl-D-glucosamine (GlcNAc) being catalyzed by the N-acylglucosamine 2-epimerase (AGE),
(b) formation of N-acetyl-D-neuraminic acid (Neu5Ac) from ManNAc and pyruvate being catalyzed by the N-acetylneuraminate lyase (NAL),
(c) formation of cytidine 5'-monophosphate (CMP) from cytidine and adenosine 5'-triphosphate (ATP) being catalyzed by the uridine kinase (UDK),
(d) formation of cytidine 5'-diphosphate (CDP) from cytidine 5'-monophosphate (CMP) and adenosine 5'-triphosphate (ATP) being catalyzed by the uridine monophosphate kinase,
(e) formation of cytidine 5'-triphosphate (CTP) from cytidine 5'-diphosphate (CDP) and polyphosphate being catalyzed by polyphosphate kinase 3 (PPK3);
(e') regeneration of adenosine 5'-triphosphate (ATP) from adenosine 5'-diphosphate (ADP) produced in the steps (c) and (d) and polyphosphate being catalyzed by polyphosphate kinase 3 (PPK3); and
(f) formation of cytidine 5'-monophospho-N-acetyl-neuraminic acid (CMP-Neu5Ac) by the reaction of N-acetyl-D-neuraminic acid (Neu5Ac) with cytidine 5'-triphosphate (CTP) being catalyzed by the N-acyl-neuraminate cytidylyltransferase (CSS),
wherein the set of enzymes is co-immobilized on a solid support; and the uridine kinase (UDK) transfers in situ the cytidine to a cytidine monophosphate (CMP) in the step (c).

In the reaction of N-acetyl-D-neuraminic acid (Neu5Ac) with cytidine 5'-triphosphate (CTP) being catalyzed by the N-acylneuraminate cytidylyltransferase (CSS), pyrophosphate (PPi) is formed as a side product. Although pyrophosphate is unstable in aqueous solution, it only slowly hydrolyzes into inorganic phosphate (Pi). It is known that a high concentration of pyrophosphate inhibit the activity of the N-acylneuraminate cytidylyltransferase (CSS) involved in production of cytidine 5'-monophospho-N-acetyl-neuraminic acid (CMP-Neu5Ac).

Thus, in one embodiment of the present invention, the set of enzymes further comprises an inorganic diphosphatase (PPA) and the present invention is directed to a method for producing cytidine 5'-monophospho-N-acetyl-neuraminic acid (CMP-Neu5Ac, 1)

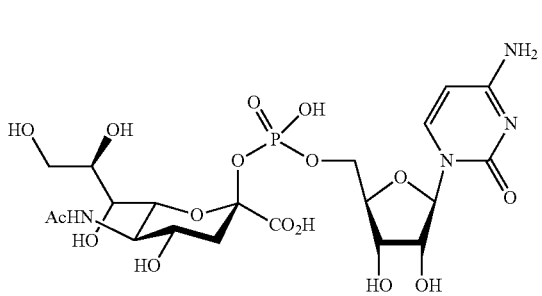

comprising:
A) providing a solution comprising N-acetyl-D-glucosamine, pyruvate, polyphosphate, cytidine, and adenosine 5'-triphosphate (ATP), and
a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase, a polyphosphate kinase 3 (PPK3), and an inorganic diphosphatase (PPA);
B) mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine monophosphate (CMP). Preferably, the set of enzymes is co-immobilized on a solid support.

In the step B), during the reaction of a resulting solution to produce cytidine 5'-monophospho-N-acetyl-neuraminic acid (CMP-Neu5Ac) in the presence of the set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase, a polyphosphate kinase 3 (PPK3) and an inorganic diphosphatase (PPA), the following cascade reactions are performed:
(a) formation of N-acetyl-D-mannosamine (ManNAc) from N-acetyl-D-glucosamine (GlcNAc) being catalyzed by the N-acylglucosamine 2-epimerase (AGE),
(b) formation of N-acetyl-D-neuraminic acid (Neu5Ac) from ManNAc and pyruvate being catalyzed by the N-acetylneuraminate lyase (NAL), (c) formation of cytidine 5'-monophosphate (CMP) from cytidine and adenosine 5'-triphosphate (ATP) being catalyzed by the uridine kinase (UDK),
(d) formation of cytidine 5'-diphosphate (CDP) from cytidine 5'-monophosphate (CMP) and adenosine 5'-triphosphate (ATP) being catalyzed by the uridine monophosphate kinase,
(e) formation of cytidine 5'-triphosphate (CTP) from cytidine 5'-diphosphate (CDP) and polyphosphate being catalyzed by polyphosphate kinase 3 (PPK3);
(e') regeneration of adenosine 5'-triphosphate (ATP) from adenosine 5'-diphosphate (ADP) produced in the steps (c) and (d) and polyphosphate being catalyzed by polyphosphate kinase 3 (PPK3);
(f) formation of cytidine 5'-monophospho-N-acetyl-neuraminic acid (CMP-Neu5Ac) by the reaction of N-acetyl-D-neuraminic acid (Neu5Ac) with cytidine 5'-triphosphate (CTP) being catalyzed by the N-acyl-neuraminate cytidylyltransferase (CSS); and
(g) conversion of pyrophosphate produced in the step (f) to phosphate being catalyzed by the inorganic diphosphatase (PPA).

Therefore, the present invention is directed to a method for producing cytidine 5'-monophospho-N-acetyl-neuraminic acid (CMP-Neu5Ac, 1)

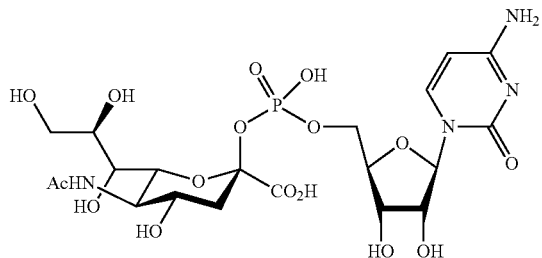

comprising:
A) providing a solution comprising N-acetyl-D-glucosamine, pyruvate, polyphosphate, cytidine, and adenosine 5'-triphosphate (ATP), and
a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase, a polyphosphate kinase 3 (PPK3), and an inorganic diphosphatase (PPA);
B) mixing said solution and said set of enzymes and reacting a resulting solution to produce cytidine 5'-monophospho-N-acetyl-neuraminic acid (CMP-Neu5Ac) by
(a) formation of N-acetyl-D-mannosamine (ManNAc) from N-acetyl-D-glucosamine (GlcNAc) being catalyzed by the N-acylglucosamine 2-epimerase (AGE),
(b) formation of N-acetyl-D-neuraminic acid (Neu5Ac) from ManNAc and pyruvate being catalyzed by the N-acetylneuraminate lyase (NAL), (c) formation of cytidine 5'-monophosphate (CMP) from cytidine and adenosine 5'-triphosphate (ATP) being catalyzed by the uridine kinase (UDK),
(d) formation of cytidine 5'-diphosphate (CDP) from cytidine 5'-monophosphate (CMP) and adenosine 5'-triphosphate (ATP) being catalyzed by the uridine monophosphate (UMP) kinase,
(e) formation of cytidine 5'-triphosphate (CTP) from cytidine 5'-diphosphate (CDP) and polyphosphate being catalyzed by polyphosphate kinase 3 (PPK3);
(e') regeneration of adenosine 5'-triphosphate (ATP) from adenosine 5'-diphosphate (ADP) produced in the steps (c) and (d) and polyphosphate being catalyzed by polyphosphate kinase 3 (PPK3);
(f) formation of cytidine 5'-monophospho-N-acetyl-neuraminic acid (CMP-Neu5Ac) by the reaction of N-acetyl-D-neuraminic acid (Neu5Ac) with cytidine 5'-triphosphate (CTP) being catalyzed by the N-acyl-neuraminate cytidylyltransferase (CSS); and
(g) conversion of pyrophosphate produced in the step (f) to phosphate being catalyzed by the inorganic diphosphatase (PPA),
wherein the uridine kinase (UDK) transfers in situ the cytidine to a cytidine monophosphate (CMP) in the step (c). Preferably, the set of enzymes is co-immobilized on a solid support.

It is known that ATP can be used as an activator of N-acylneuraminate cytidylyltransferase (CSS) (Ignacio G. BRAVO et. al, Biochem. J, 2001, 258, pp 568-598) and in contrary, AMP and ADP inhibit the activity of N-acylneuraminate cytidylyltransferase (CSS).

In the method of the present invention, adenosine 5'-triphosphate (ATP) is regenerated from adenosine 5'-diphosphate (ADP) produced in the steps (c) and (d) and polyphosphate being catalyzed by polyphosphate kinase 3 (PPK3).

Therefore, additionally, the set of enzymes further comprises a one-domain polyphosphate kinase 2 (1 DPPK2) and/or a two-domain polyphosphate kinase 2 (2DPPK2).

In addition, the cascade can be extended by adding a 1D-PPK2 and/or 2D-PPK2 in order to activate phosphorylation of AMP to ADP, and ADP to ATP. Moreover, the cascade can be extended by adding a 1D-PPK2 and/or a 2D-PPK2 in order to inhibit frequent hydrolysis of adenosine phosphates.

The one-domain polyphosphate kinase 2 (1D-PPK2) and/or the two-domain polyphosphate kinase 2 (2D-PPK2) are preferably also co-immobilized with the above-mentioned enzymes on the same solid support.

As ATP is continuously regenerated from ADP and polyphosphate in the inventive methods described herein, the production of CMP-Neu5NAc can be performed with catalytic amount of ATP.

Thus, in one embodiment of the present invention, the set of enzymes further comprises an inorganic diphosphatase (PPA) and the present invention is directed to a method for producing cytidine 5'-monophospho-N-acetyl-neuraminic acid (CMP-Neu5Ac, 1)

Thus, the present invention is directed to a method for producing cytidine 5'-monophospho-N-acetyl-neuraminic acid (CMP-Neu5Ac, 1)

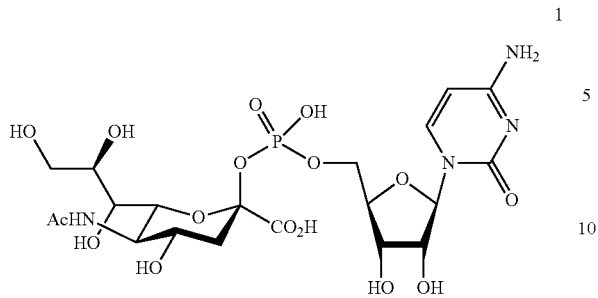

comprising:
A) providing a solution comprising N-acetyl-D-glucosamine, pyruvate, polyphosphate, cytidine, and adenosine 5'-triphosphate (ATP), and
a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase, a polyphosphate kinase 3 (PPK3), an inorganic diphosphatase (PPA), a one-domain polyphosphate kinase 2 (1 DPPK2) and/or a two-domain polyphosphate kinase 2 (2DPPK2);
B) mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine monophosphate (CMP). Preferably, the set of enzymes is co-immobilized on a solid support.

Reworded, the present invention is directed to a method for producing cytidine 5'-monophospho-N-acetyl-neuraminic acid (CMP-Neu5Ac, 1)

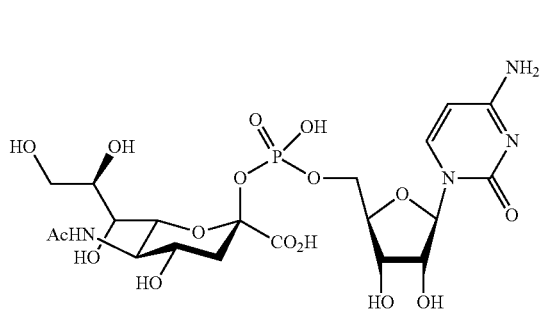

comprising:
A) providing a solution comprising N-acetyl-D-glucosamine, pyruvate, polyphosphate, cytidine, and adenosine 5'-triphosphate (ATP), and
a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase, a polyphosphate kinase 3 (PPK3), an inorganic diphosphatase (PPA), an one-domain polyphosphate kinase 2 (1 DPPK2) and/or a two-domain polyphosphate kinase 2 (2DPPK2);
B) mixing said solution and said set of enzymes and reacting a resulting solution to produce cytidine 5'-monophospho-N-acetyl-neuraminic acid (CMP-Neu5Ac) by (a) formation of N-acetyl-D-mannosamine (ManNAc) from N-acetyl-D-glucosamine (GlcNAc) being catalyzed by the N-acylglucosamine 2-epimerase (AGE),
(b) formation of N-acetyl-D-neuraminic acid (Neu5Ac) from ManNAc and pyruvate being catalyzed by the N-acetylneuraminate lyase (NAL),
(c) formation of cytidine 5'-monophosphate (CMP) from cytidine and adenosine 5'-triphosphate (ATP) being catalyzed by the uridine kinase (UDK),
(d) formation of cytidine 5'-diphosphate (CDP) from cytidine 5'-monophosphate (CMP) and adenosine 5'-triphosphate (ATP) being catalyzed by the uridine monophosphate (UMP) kinase,
(e) formation of cytidine 5'-triphosphate (CTP) from cytidine 5'-diphosphate (CDP) and polyphosphate being catalyzed by polyphosphate kinase 3 (PPK3);
(e') regeneration of adenosine 5'-triphosphate (ATP) from adenosine 5'-diphosphate (ADP) produced in the steps (c) and (d) and polyphosphate being catalyzed by polyphosphate kinase 3 (PPK3);
(f) formation of cytidine 5'-monophospho-N-acetyl-neuraminic acid (CMP-Neu5Ac) by the reaction of N-acetyl-D-neuraminic acid (Neu5Ac) with cytidine 5'-triphosphate (CTP) being catalyzed by the N-acylneuraminate cytidylyltransferase (CSS); and
(g) conversion of pyrophosphate produced in the step (f) to phosphate being catalyzed by the inorganic diphosphatase (PPA),
(h) phosphorylation of AMP to ADP, and ADP to ATP being catalyzed by the one-domain polyphosphate kinase 2 (1 DPPK2) and/or the two-domain polyphosphate kinase 2 (2DPPK2);
wherein the uridine kinase (UDK) transfers in situ the cytidine to a cytidine monophosphate (CMP) in the step (c). Preferably, the set of enzymes is co-immobilized on a solid support.

Polyphosphate serves as the only energy carrier in the inventive methods described herein and is used as a phosphate source in the regeneration of ATP from ADP using a polyphosphate kinase 3 (PPK3). The regeneration of ATP can be enhanced by adding a 1-domain polyphosphate kinase (1D-PPK), which also catalyzes the phosphorylation of ADP to ATP, preferably a 1-domain polyphosphate kinase 2 (1D-PPK2) to the enzyme cascade of the inventive methods. Moreover, nucleoside phosphates, such as ADP are instable in aqueous media and tend to hydrolyze rapidly. To avoid the loss of ADP by hydrolysis to AMP, a 2-domain polyphosphate kinase (2D-PPK) which catalyzes the phosphorylation of AMP to ADP, preferably a 2-domain polyphosphate kinase 2 (2D-PPK2) can be added along with a 1D-PPK or alone to the inventive enzyme cascade.

Polyphosphate is able to form stable, water-soluble complexes with metal ions (e.g. $Ca^{2+}$, $Mg^{2+}$, $Mn^{2+}$, $Fe^{2+/3+}$) which were initially dissolved in aqueous media. As the ability of a particular polyphosphate to sequester a particular metal ion decreases with increasing chain length of the polyphosphate, long-chain polyphosphates are preferred in the present invention. More preferred are polyphosphates having at least 14 phosphate residues. Most preferred are polyphosphates having at least 25 phosphate residues.

As mentioned above, the cascade of the inventive method can be extended by adding an N-acetyl-glucosamine deacetylase in order to produce the N-acetyl-D-glucosamine (GlcNAc) separately or in situ from D-glucosamine (GlcN) and acetate.

In some embodiments, in the Step A), the N-acetyl-D-glucosamine (GlcNAc) is separately or in situ produced from D-glucosamine (GlcN) and acetate in the presence of N-acetyl-glucosamine deacetylase.

In the Step A), the N-acetyl-D-glucosamine (GlcNAc) is separately or in situ produced from D-glucosamine (GlcN) and acetate in the presence of N-acetyl-glucosamine deacetylase.

Thus, in some cases, an additional step A1) may be performed separately before step A) as follows:
A1) producing N-acetyl-D-glucosamine from D-glucosamine (GlcN) and acetate in the presence of N-acetyl-glucosamine deacetylase.

Thus, any of the above-mentioned inventive methods for producing CMP-Neu5Ac comprises the additional step A1) before the step A) and the steps A) and B) are performed subsequently.

In another cases, N-acetyl-D-glucosamine (GlcNAc) is in situ produced from D-glucosamine (GlcN) and acetate in the presence of N-acetyl-glucosamine deacetylase.

Thus, any of the above-mentioned inventive methods for producing CMP-Neu5Ac comprises alternative steps A') and B'). Most of all, in the Step B') N-acetyl-D-glucosamine (GlcNAc) will be in situ formed as follows:
(a') formation of N-acetyl-D-glucosamine (GlcNAc) from D-glucosamine (GlcN) and acetate being catalyzed by the N-acetyl-glucosamine deacetylase.

Thus, the present invention is directed to a method for producing cytidine 5'-monophospho-N-acetyl-neuraminic acid (CMP-Neu5Ac, 1)

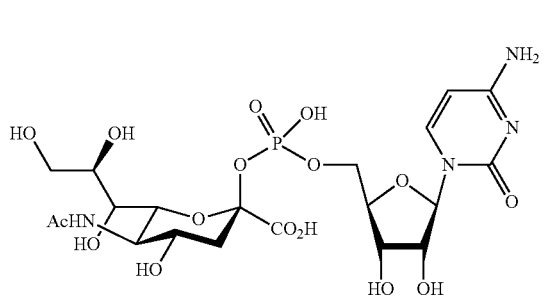

comprising:
A') providing a solution comprising D-glucosamine, acetate, pyruvate, polyphosphate, cytidine, and adenosine 5'-triphosphate (ATP), and
a set of enzymes comprising an N-acetylglucosamine deacetylase, an N-acyl-glucosamine 2-epimerase (AGE), an N-acetylneuraminate lyase (NAL), an N-acetylneuraminate cytidylyltransferase (CSS), a uridine kinase (UDK), a uridine monophosphate kinase and a polyphosphate kinase 3 (PPK3);
B') mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine 5'-monophosphate (CMP).

Preferably, the set of enzymes is co-immobilized on a solid support and more preferably the set of enzymes is co-immobilized on a reusable, mechanically stable solid support thereby increasing or retaining a large fraction of the activity of each enzyme.

In the step B'), during the reaction of a resulting solution to produce cytidine 5'-monophospho-N-acetyl-neuraminic acid (CMP-Neu5Ac) in the presence of the set of enzymes comprising an N-acetylglucosamine deacetylase, an N-acyl-glucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3), the following cascade reactions are performed:
(a') formation of N-acetyl-D-glucosamine (GlcNAc) from D-glucosamine (GlcN) and acetate being catalyzed by the N-acetyl-glucosamine deacetylase,
(a) formation of N-acetyl-D-mannosamine (ManNAc) from N-acetyl-D-glucosamine (GlcNAc) being catalyzed by the N-acylglucosamine 2-epimerase (AGE),
(b) formation of N-acetyl-D-neuraminic acid (Neu5Ac) from ManNAc and pyruvate being catalyzed by the N-acetylneuraminate lyase (NAL),
(c) formation of cytidine 5'-monophosphate (CMP) from cytidine and adenosine 5'-triphosphate (ATP) being catalyzed by the uridine kinase (UDK),
(d) formation of cytidine 5'-diphosphate (CDP) from cytidine 5'-monophosphate (CMP) and adenosine 5'-triphosphate (ATP) being catalyzed by the uridine monophosphate kinase,
(e) formation of cytidine 5'-triphosphate (CTP) from cytidine 5'-diphosphate (CDP) and polyphosphate being catalyzed by polyphosphate kinase 3 (PPK3);
(e') regeneration of adenosine 5'-triphosphate (ATP) from adenosine 5'-diphosphate (ADP) produced in the steps (c) and (d) and polyphosphate being catalyzed by polyphosphate kinase 3 (PPK3); and
(f) formation of cytidine 5'-monophospho-N-acetyl-neuraminic acid (CMP-Neu5Ac) by the reaction of N-acetyl-D-neuraminic acid (Neu5Ac) with cytidine 5'-triphosphate (CTP) being catalyzed by the N-acyl-neuraminate cytidylyltransferase (CSS).

Therefore, the present invention refers to a method for producing cytidine 5'-monophospho-N-acetyl-neuraminic acid (CMP-Neu5Ac, 1) comprising:
A') providing a solution comprising D-glucosamine, acetate, pyruvate, polyphosphate, cytidine, and adenosine 5'-triphosphate (ATP), and
a set of enzymes comprising an N-acetyl-glucosamine deacetylase, an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);
B') mixing said solution and said set of enzymes and reacting a resulting solution to produce cytidine 5'-monophospho-N-acetyl-neuraminic acid (CMP-Neu5Ac) by
(a') formation of N-acetyl-D-glucosamine (GlcNAc) from D-glucosamine (GlcN) and acetate being catalyzed by the N-acetyl-glucosamine deacetylase,
(a) formation of N-acetyl-D-mannosamine (ManNAc) from N-acetyl-D-glucosamine (GlcNAc) being catalyzed by the N-acylglucosamine 2-epimerase (AGE),
(b) formation of N-acetyl-D-neuraminic acid (Neu5Ac) from ManNAc and pyruvate being catalyzed by the N-acetylneuraminate lyase (NAL),
(c) formation of cytidine 5'-monophosphate (CMP) from cytidine and adenosine 5'-triphosphate (ATP) being catalyzed by the uridine kinase (UDK), (d) formation of cytidine 5'-diphosphate (CDP) from cytidine 5'-monophosphate (CMP) and adenosine 5'-triphosphate (ATP) being catalyzed by the uridine monophosphate kinase, (e) formation of cytidine 5'-triphosphate (CTP) from cytidine 5'-diphosphate (CDP) and polyphosphate being catalyzed by polyphosphate kinase 3 (PPK3);

(e') regeneration of adenosine 5'-triphosphate (ATP) from adenosine 5'-diphosphate (ADP) produced in the steps (c) and (d) and polyphosphate being catalyzed by polyphosphate kinase 3 (PPK3); and (f) formation of cytidine 5'-monophospho-N-acetyl-neuraminic acid (CMP-Neu5Ac) by the reaction of N-acetyl-D-neuraminic acid (Neu5Ac) with cytidine 5'-triphosphate (CTP) being catalyzed by the N-acyl-neuraminate cytidylyltransferase (CSS), wherein the uridine kinase (UDK) transfers in situ the cytidine to a cytidine monophosphate (CMP) in the step (c). Preferably, the set of enzymes is co-immobilized on a solid support.

Preferably, the set of enzymes further comprises an inorganic diphosphatase (PPA) and the present invention is directed to a method for producing cytidine 5'-monophospho-N-acetyl-neuraminic acid (CMP-Neu5Ac, 1) comprising:

A') providing a solution comprising D-glucosamine, acetate, pyruvate, polyphosphate, cytidine, and adenosine 5'-triphosphate (ATP), and a set of enzymes comprising an N-acetyl-glucosamine deacetylase, an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3) and an inorganic diphosphatase (PPA);

B') mixing said solution and said set of enzymes and reacting a resulting solution to produce cytidine 5'-monophospho-N-acetyl-neuraminic acid (CMP-Neu5Ac), wherein the uridine kinase (UDK) transfers in situ the cytidine to a cytidine 5'-monophosphate (CMP). Preferably, the set of enzymes is co-immobilized on a solid support.

Reworded, a method for producing cytidine 5'-monophospho-N-acetyl-neuraminic acid (CMP-Neu5Ac, 1) comprising:

A') providing a solution comprising D-glucosamine, acetate, pyruvate, polyphosphate, cytidine, and adenosine 5'-triphosphate (ATP), and a set of enzymes comprising an N-acetyl-glucosamine deacetylase, an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3) and an inorganic diphosphatase (PPA);

B') mixing said solution and said set of enzymes and reacting a resulting solution to produce cytidine 5'-monophospho-N-acetyl-neuraminic acid (CMP-Neu5Ac) by (a') formation of N-acetyl-D-glucosamine (GlcNAc) from D-glucosamine (GlcN) and acetate being catalyzed by the N-acetyl-glucosamine deacetylase, (a) formation of N-acetyl-D-mannosamine (ManNAc) from N-acetyl-D-glucosamine (GlcNAc) being catalyzed by the N-acylglucosamine 2-epimerase (AGE), (b) formation of N-acetyl-D-neuraminic acid (Neu5Ac) from ManNAc and pyruvate being catalyzed by the N-acetylneuraminate lyase (NAL), (c) formation of cytidine 5'-monophosphate (CMP) from cytidine and adenosine 5'-triphosphate (ATP) being catalyzed by the uridine kinase (UDK), (d) formation of cytidine 5'-diphosphate (CDP) from cytidine 5'-monophosphate (CMP) and adenosine 5'-triphosphate (ATP) being catalyzed by the uridine monophosphate kinase, (e) formation of cytidine 5'-triphosphate (CTP) from cytidine 5'-diphosphate (CDP) and polyphosphate being catalyzed by polyphosphate kinase 3 (PPK3);

(e') regeneration of adenosine 5'-triphosphate (ATP) from adenosine 5'-diphosphate (ADP) produced in the steps (c) and (d) and polyphosphate being catalyzed by polyphosphate kinase 3 (PPK3); and (f) formation of cytidine 5'-monophospho-N-acetyl-neuraminic acid (CMP-Neu5Ac) by the reaction of N-acetyl-D-neuraminic acid (Neu5Ac) with cytidine 5'-triphosphate (CTP) being catalyzed by the N-acyl-neuraminate cytidylyltransferase (CSS), (g) conversion of pyrophosphate produced in the step (f) to phosphate being catalyzed by the inorganic diphosphatase (PPA).

Furthermore, the present invention is directed to a method for producing cytidine 5'-monophospho-N-acetyl-neuraminic acid (CMP-Neu5Ac, 1) comprising:

A') providing a solution comprising D-glucosamine, acetate, pyruvate, polyphosphate, cytidine, and adenosine 5'-triphosphate (ATP), and a set of enzymes comprising an N-acetyl-glucosamine deacetylase, an N-acylglucosamine 2-epimerase (AGE), an N-acetylneuraminate lyase (NAL), an N-acylneuraminate cytidylyltransferase (CSS), a uridine kinase (UDK), a uridine monophosphate kinase, a polyphosphate kinase 3 (PPK3), an inorganic diphosphatase (PPA), an one-domain polyphosphate kinase 2 (1 DPPK2) and/or a two-domain polyphosphate kinase 2 (2DPPK2);

B') mixing said solution and said set of enzymes and reacting a resulting solution to produce cytidine 5'-monophospho-N-acetyl-neuraminic acid (CMP-Neu5Ac), wherein the uridine kinase (UDK) transfers in situ the cytidine to a cytidine monophosphate (CMP). Preferably, the set of enzymes is co-immobilized on a solid support.

Reworded, a method for producing cytidine 5'-monophospho-N-acetyl-neuraminic acid (CMP-Neu5Ac, 1) comprising:

A') providing a solution comprising D-glucosamine, acetate, pyruvate, polyphosphate, cytidine, and adenosine 5'-triphosphate (ATP), and a set of enzymes comprising an N-acetyl-glucosamine deacetylase, an N-acylglucosamine 2-epimerase (AGE), an N-acetylneuraminate lyase (NAL), an N-acylneuraminate cytidylyltransferase (CSS), a uridine kinase (UDK), a uridine monophosphate kinase, a polyphosphate kinase 3 (PPK3), an inorganic diphosphatase (PPA), an one-domain polyphosphate kinase 2 (1 DPPK2) and/or a two-domain polyphosphate kinase 2 (2DPPK2);

B) mixing said solution and said set of enzymes and reacting a resulting solution to produce cytidine 5'-monophospho-N-acetyl-neuraminic acid (CMP-Neu5Ac) by (a') formation of N-acetyl-D-glucosamine (GlcNAc) from D-glucosamine (GlcN) and acetate being catalyzed by the N-acetyl-glucosamine deacetylase,
(a) formation of N-acetyl-D-mannosamine (ManNAc) from N-acetyl-D-glucosamine (GlcNAc) being catalyzed by the N-acylglucosamine 2-epimerase (AGE),
(b) formation of N-acetyl-D-neuraminic acid (Neu5Ac) from ManNAc and pyruvate being catalyzed by the N-acetylneuraminate lyase (NAL),
(c) formation of cytidine 5'-monophosphate (CMP) from cytidine and adenosine 5'-triphosphate (ATP) being catalyzed by the uridine kinase (UDK),
(d) formation of cytidine 5'-diphosphate (CDP) from cytidine 5'-monophosphate (CMP) and adenosine 5'-triphosphate (ATP) being catalyzed by the uridine monophosphate (UMP) kinase,
(e) formation of cytidine 5'-triphosphate (CTP) from cytidine 5'-diphosphate (CDP) and polyphosphate being catalyzed by polyphosphate kinase 3 (PPK3);
(e') regeneration of adenosine 5'-triphosphate (ATP) from adenosine 5'-diphosphate (ADP) produced in the steps (c) and (d) and polyphosphate being catalyzed by polyphosphate kinase 3 (PPK3);
(f) formation of cytidine 5'-monophospho-N-acetyl-neuraminic acid (CMP-Neu5Ac) by the reaction of N-acetyl-D-neuraminic acid (Neu5Ac) with cytidine 5'-triphosphate (CTP) being catalyzed by the N-acyl-neuraminate cytidylyltransferase (CSS); and
(g) conversion of pyrophosphate produced in the step (f) to phosphate being catalyzed by the inorganic diphosphatase (PPA),
(h) phosphorylation of AMP to ADP, and ADP to ATP being catalyzed by the one-domain polyphosphate kinase 2 (1 DPPK2) and/or the two-domain polyphosphate kinase 2 (2DPPK2);
wherein the uridine kinase (UDK) transfers in situ the cytidine to a cytidine monophosphate (CMP) in the step (c). Preferably, the set of enzymes is co-immobilized on a solid support.

In some embodiments, the resulting solution in the step B) has a pH value in a range of 5.0-10.0, preferred 5.5-9.5, more preferred 6.0-9.0, still more preferred 6.5-9.0, most preferred 7.0-9.0.

Preferably, the resulting solution is a buffer solution having a pH value in a range of 5.0-10.0, preferred 5.5-9.5, more preferred 6.0-9.0, still more preferred 6.5-9.0, most preferred 7.0-9.0.

The buffer solution comprises at least one of acids and at least one of bases. Preferred the at least one of sulfonic acids is selected from the group consisting of citric acid, [tris(hydroxymethyl)methylamino]propanesulfonic acid (TAPS), 2-(bis(2-hydroxyethyl)amino)acetic acid (Bicine), tris(hydroxymethyl)aminomethane (Tris), N-[tris(hydroxymethyl)methyl]glycine (Tricine), 3-[N-tris(hydroxymethyl)-methylamino]-2-hydroxypropanesulfonic acid (TAPSO), 4-(2-hydroxyethyl)-1-piperazineethanesulfonic acid (HEPES), 2-[[1,3-dihydroxy-2-(hydroxymethyl)-propan-2-yl]amino]ethanesulfonic acid (TES), 3-(N-morpholino)propanesulfonic acid (MOPS), piperazine-N,N'-bis(2-ethanesulfonic acid (PIPES), 2-(N-morpholino)ethanesulfonic acid (MES).

Preferred the at least one of bases is selected from the group consisting of metal hydroxide, metal carbonate, metal bicarbonate, metal phosphate, metal biphosphate; more preferred, sodium hydroxide, calcium hydroxide, potassium hydroxide, sodium bicarbonate, sodium carbonate, calcium carbonate, potassium carbonate, monosodium phosphate, monocalcium phosphate, monopotassium phosphate, monomagnesium phosphate, disodium phosphate, calcium phosphate, and potassium phosphate.

An appropriate concentration of $Mg^{2+}$ as cofactor contributes full activation of the uridine monophosphate (UMP) kinase.

In some embodiments, the resulting solution in the method of the present invention further comprises $Mg^{2+}$ with a concentration in a range of 0.1 mM to 500 mM, 0.1 mM to 200 mM, preferably 10 to 100 mM, more preferably, 50 to 100 mM, most preferably 20 mM to 50 mM. Preferably, a source of $Mg^{2+}$ is magnesium bromide, magnesium chloride, magnesium carbonate, monomagnesium phosphate, magnesium phosphate, magnesium sulfate and hydrates thereof.

Optionally, the resulting solution further comprises a reducing reagent such as 2-mercaptoethanol and dithiothreitol (DTT).

The reaction temperature of the reaction solution affects the efficiency of the enzymatic cascade reactions. Therefore, in the methods of the present invention, the optimal reaction temperature of the step B) is in a range of 20° C. to 65° C., preferred, 25° C. to 60° C., still preferred 25° C. to 55° C., more preferred 30° C. to 55° C., still more preferred 35° C. to 55° C., and most preferred 34° C. to 50° C.

In the present invention, a concentration of N-acetyl-D-glucosamine is in a range of 1 mM to 5000 mM, preferred 1 mM to 4000 mM, more preferred 2 mM to 4500 mM, still more preferred 5 mM to 3000 mM, most preferred 10 mM to 2000 mM; and/or a concentration of the pyruvate is in a range of 1 mM to 5000 mM, preferred 2 mM to 4000 mM, more preferred 5 mM to 3000 mM, still more preferred 10 mM to 3000 mM, most preferred 20 mM to 2000 mM; and/or a concentration of the cytidine is in a range of 0.1 mM to 2000 mM, preferred 1 mM to 1000 mM, more preferred 1 mM to 500 mM, and/or a concentration of adenosine 5'-triphosphate (ATP) is in a range of 0.001 mM to 100 mM, preferred 0.01 mM to 100 mM, more preferred 0.1 mM to 500 mM, still more preferred 0.1 mM to 100 mM, most preferred 0.1 mM to 40 mM:

Thus, the present invention refers to a method for producing cytidine 5'-monophospho-N-acetyl-neuraminic acid (CMP-Neu5Ac, 1)

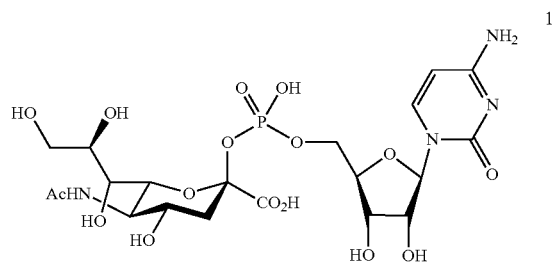

comprising:
A) providing a solution comprising N-acetyl-D-glucosamine, pyruvate, polyphosphate, cytidine, and adenosine 5'-triphosphate (ATP), and
a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);

B) mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine monophosphate (CMP); and
wherein a concentration of N-acetyl-D-glucosamine is in the range of 1 mM to 5000 mM; and/or a concentration of the pyruvate is in the range of 1 mM to 5000 mM; and/or a concentration of the cytidine is in the range of 0.1 mM to 2000 mM; and/or a concentration of adenosine 5'-triphosphate (ATP) is in the range of 0.001 mM to 100 mM. Preferably, the concentration of N-acetyl-D-glucosamine is in the range of 1 mM to 2000 mM; and/or the concentration of the pyruvate is in the range of 1 mM to 2000 mM; and/or the concentration of the cytidine is in the range of 0.1 mM to 2000 mM; and/or the concentration of adenosine 5'-triphosphate (ATP) is in the range of 0.01 mM to 100 mM. More preferably the concentration of N-acetyl-D-glucosamine is in the range of 1 mM to 2000 mM and the concentration of the pyruvate is in the range of 1 mM to 2000 mM and the concentration of the cytidine is in the range of 0.1 mM to 2000 mM and the concentration of adenosine 5'-triphosphate (ATP) is in the range of 0.01 mM to 100 mM. Preferably, the set of enzymes is co-immobilized on a solid support.

In some embodiments of the method of the present invention, a concentration of N-acetyl-D-glucosamine is in a range of 1 mM to 500 mM; and/or a concentration of the pyruvate is in a range of 1 mM to 500 mM; and/or a concentration of the cytidine is in a range of 1 mM to 500 mM; and/or a concentration of adenosine 5'-triphosphate (ATP) is in a range of 2 mM to 40 mM.

Thus, the present invention refers to a method for producing cytidine 5'-monophospho-N-acetyl-neuraminic acid (CMP-Neu5Ac, 1)

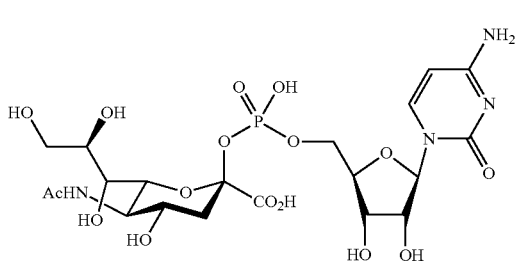

comprising:
A) providing a solution comprising N-acetyl-D-glucosamine, pyruvate, polyphosphate, cytidine, and adenosine 5'-triphosphate (ATP), and
a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);
B) mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine monophosphate (CMP); and wherein a concentration of N-acetyl-D-glucosamine is in the range of 1 mM to 500 mM; and/or a concentration of the pyruvate is in the range of 1 mM to 500 mM; and/or a concentration of the cytidine is in the range of 1 mM to 500 mM; and/or a concentration of adenosine 5'-triphosphate (ATP) is in the range of 2 mM to 40 mM. Preferably, the concentration of N-acetyl-D-glucosamine is in the range of 1 mM to 500 mM and the concentration of the pyruvate is in the range of 1 mM to 500 mM and the concentration of the cytidine is in the range of 1 mM to 500 mM and the concentration of adenosine 5'-triphosphate (ATP) is in the range of 2 mM to 40 mM. Preferably, the set of enzymes is co-immobilized on a solid support.

Preferably, in the method of the present invention, the ratio of N-acetyl-D-glucosamine (GlcNAc) and pyruvate is in the range of 1:1 to 1:10000, 1:1 to 1:5000, 1:1 to 1:2000, 1:1 to 1:1000, or 1:1 to 1:100. The pyruvate refers to sodium pyruvate, or alternatively pyruvic acid is applied.

More preferably, in the method of the present invention, the ratio of N-acetyl-D-glucosamine (GlcNAc) and pyruvate is in the range of 1:1 to 1:20, preferred 1:1 to 1:15, more preferred 1:1 to 1:10, still more preferred 1:1 to 1:5, most preferred 1:1 to 1:2. The pyruvate refers to sodium pyruvate, or alternatively pyruvic acid is applied.

Preferably, in the method of the present invention, the ratio of N-acetyl-D-glucosamine (GlcNAc) and cytidine is in the range of 1:1 to 100:1, preferred 1:1 to 50:1, more preferred 1:1 to 30:1, still more preferred 1:1 to 20:1, most preferred 1:1 to 15:1.

Preferably, in the method of the present invention, the ratio of D-glucosamine (GlcN) and acetate is in the range of 1:1 to 1:10000, 1:1 to 1:5000, 1:1 to 1:2000, 1:1 to 1:1000, or 1:1 to 1:100. The acetate refers to lithium acetate, sodium acetate, potassium acetate or alternatively acetic acid is applied.

Preferably, in the method of the present invention, the ratio of adenosine 5'-triphosphate (ATP) and cytidine is in the range of 1:1 to 1:2000, preferred 1:2 to 1:1000, more preferred 1:4 to 1:1000 most preferred 1:10 to 1:500.

In a preferred embodiment of the method of the present invention,
the ratio of N-acetyl-D-glucosamine (GlcNAc) and pyruvate is in the range of 1:1 to 1:50; and
the ratio of N-acetyl-D-glucosamine (GlcNAc) and cytidine is in the range of 1:1 to 100:1; and
the ratio of adenosine 5'-triphosphate (ATP) and cytidine is in the range of 1:1 to 1:100; and
the ratio of adenosine 5'-triphosphate (ATP) and polyphosphate is in the range of 1:1 to 1:200; and/or
the concentration of N-acetyl-D-glucosamine (GlcNAc) is in the range of 20 to 3000 mM; and
the concentration of pyruvate is in the range of 20 to 3000 mM; and
the concentration of cytidine is in the range of 1 to 50 mM; and
the concentration of adenosine 5'-triphosphate (ATP) is in the range of 0.001 to 10 mM; and
the concentration of polyphosphate is in the range of 1 to 30 mM.

In another preferred embodiment of the method disclosed herein,
the ratio of N-acetyl-D-glucosamine (GlcNAc) and pyruvate is in the range of 1:1 to 1:20; and
the ratio of N-acetyl-D-glucosamine (GlcNAc) and cytidine is in the range of 1:1 to 30:1; and the ratio of adenosine 5'-triphosphate (ATP) and cytidine is in the range of 1:1 to 1:20; and the ratio of adenosine 5'-triphosphate (ATP) and polyphosphate is in the range of 1:1 to 1:50; and/or the concentration of N-acetyl-D-glucosamine (GlcNAc) is in the range of 20 to 2000 mM; and the concentration of pyruvate is in the range of 20 to 2000 mM; and the concentration of cytidine is in the range of 1 to 20 mM; and the concentration of adenosine 5'-triphosphate (ATP) is in the range of 0.01 to 10 mM; and the concentration of polyphosphate is in the range of 1 to 20 mM.

In another preferred embodiment of the method disclosed herein, the ratio of N-acetyl-D-glucosamine (GlcNAc) and pyruvate is in the range of 1:1 to 1:2; and the ratio of N-acetyl-D-glucosamine (GlcNAc) and cytidine is in the range of 1:1 to 15:1; and the ratio of adenosine 5'-triphosphate (ATP) and cytidine is in the range of 1:1 to 1:10; and the ratio of adenosine 5'-triphosphate (ATP) and polyphosphate is in the range of 1:1 to 1:5; and/or the concentration of N-acetyl-D-glucosamine (GlcNAc) is in the range of 20 to 1000 mM; and the concentration of pyruvate is in the range of 20 to 1000 mM; and the concentration of cytidine is in the range of 1 to 15 mM; and the concentration of adenosine 5'-triphosphate (ATP) is in the range of 0.1 to 10 mM; and the concentration of polyphosphate is in the range of 1 to 10 mM.

In one aspect of the present invention, the present invention refers to a method for producing cytidine 5'-monophospho-N-acetyl-neuraminic acid (CMP-Neu5Ac, 1)

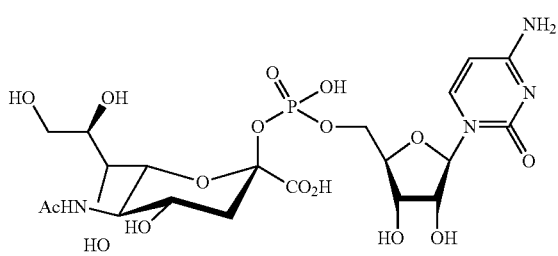

comprising:
A) providing a solution comprising N-acetyl-D-glucosamine, pyruvate, polyphosphate, cytidine, and adenosine 5'-triphosphate (ATP), and
    a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);
B) mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine monophosphate (CMP); and wherein the ratio of N-acetyl-D-glucosamine (GlcNAc) and pyruvate is in the range of 1:1 to 1:50 and the ratio of N-acetyl-D-glucosamine (GlcNAc) and cytidine is in the range of 1:1 to 100:1 and the ratio of adenosine 5'-triphosphate (ATP) and cytidine is in the range of 1:1 to 1:100 and the ratio of adenosine 5'-triphosphate (ATP) and polyphosphate is in the range of 1:1 to 1:200. Preferably, the ratio of N-acetyl-D-glucosamine (GlcNAc) and pyruvate is in the range of 1:1 to 1:20 and the ratio of N-acetyl-D-glucosamine (GlcNAc) and cytidine is in the range of 1:1 to 30:1 and the ratio of adenosine 5'-triphosphate (ATP) and cytidine is in the range of 1:1 to 1:20 and the ratio of adenosine 5'-triphosphate (ATP) and polyphosphate is in the range of 1:1 to 1:50. More preferably, the ratio of N-acetyl-D-glucosamine (GlcNAc) and pyruvate is in the range of 1:1 to 1:2 and the ratio of N-acetyl-D-glucosamine (GlcNAc) and cytidine is in the range of 1:1 to 15:1 and the ratio of adenosine 5'-triphosphate (ATP) and cytidine is in the range of 1:1 to 1:10 and the ratio of adenosine 5'-triphosphate (ATP) and polyphosphate is in the range of 1:1 to 1:5. Preferably, the set of enzymes is co-immobilized on a solid support.

In the present invention, the N-acylglucosamine 2-epimerase (AGE) comprises at least 80%, preferred at least 85%, also preferred at least 90%, more preferred at least 95%, still more preferred at least 98% of an amino acid sequence as set forth in SEQ ID NO: 1. Most preferred, the N-acylglucosamine 2-epimerase (AGE) comprises the same amino acid sequence as set forth in SEQ ID NO: 1.

The N-acetylneuraminate lyase (NAL) comprises at least 80%, preferred at least 85%, also preferred at least 90%, more preferred at least 95%, still more preferred at least 98% of an amino acid sequence as set forth in SEQ ID NO: 2. Most preferred, the N-acetylneuraminate lyase (NAL) comprises the same amino acid sequence as set forth in SEQ ID NO: 2.

The N-acylneuraminate cytidylyltransferase (CSS) is obtained from microorganisms including *Cricetulus griseus, Escherichia coli, Haemophilus ducreyi, Haemophilus influenza, Hungateiclostridium thermocellum, Mannheimia haemolytica, Neisseria meningitidis, Oncorhynchus mykiss, Pelophylax esculentus, Photobacterium leiognathi, Rattus norvegicus, Streptococcus agalactiae,* and *Sus scrofa*; mouse; and Rainbow trout. Preferably, the N-acylneuraminate cytidylyltransferase is derived from *Neisseria meningitidis* CSS. Optionally, *Neisseria meningitidis* CSS has at least one of the following mutations: Q104A, R165A, Q166A, N175A, Y179A, F192A, and F193A.

Thus, the N-acylneuraminate cytidylyltransferase (CSS) comprises at least 80%, preferred at least 85%, also preferred at least 90%, more preferred at least 95%, still more preferred at least 98% of an amino acid sequence as set forth in SEQ ID NO: 3. Most preferred, the N-acylneuraminate cytidylyltransferase (CSS) comprises the same amino acid sequence as set forth in SEQ ID NO: 3.

The uridine kinase (UDK) comprises at least 80%, preferred at least 85%, also preferred at least 90%, more preferred at least 95%, still more preferred at least 98% of an amino acid sequence as set forth in SEQ ID NO: 4. Most preferred, the uridine kinase (UDK) comprises the same amino acid sequence as set forth in SEQ ID NO: 4.

The uridine monophosphate kinase (URA6) comprises at least 80%, preferably at least 85%, also preferably at least 90%, more preferably at least 95%, still more preferably at least 98% of an amino acid sequence as set forth in SEQ ID NO: 5. Most preferably, the uridine monophosphate kinase (URA6) comprises the same amino acid sequence as set forth in SEQ ID NO: 5.

The polyphosphate kinase 3 (PPK3) comprises at least 80%, preferably at least 85%, also preferably at least 90%, more preferably at least 95%, still more preferably at least 98% of an amino acid sequence as set forth in SEQ ID NO: 6. Most preferably, the polyphosphate kinase 3 (PPK3) comprises the same amino acid sequence as set forth in SEQ ID NO: 6.

The inorganic diphosphatase (PPA) comprises at least 80%, preferably at least 85%, also preferably at least 90%, more preferably at least 95%, still more preferably at least 98% of an amino acid sequence as set forth in SEQ ID NO: 7. Most preferably, the inorganic diphosphatase (PPA) comprises the same amino acid sequence as set forth in SEQ ID NO: 7.

The two-domain polyphosphate kinase 2 (2D-PPK2) comprises at least 80%, preferred at least 85%, also preferred at least 90%, more preferred at least 95%, still more preferred at least 98% of an amino acid sequence as set forth in SEQ ID NO: 8. Most preferred, the two-domain polyphosphate kinase 2 (2D-PPK2) comprises the same amino acid sequence as set forth in SEQ ID NO: 8.

The one-domain polyphosphate kinase 2 (1D-PPK2) comprises at least 80%, preferably at least 85%, also preferably at least 90%, more preferably at least 95%, still more preferably at least 98% of an amino acid sequence as set forth in SEQ ID NO: 9. Most preferably, the one-domain polyphosphate kinase 2 (1D-PPK2) comprises the same amino acid sequence as set forth in SEQ ID NO: 9.

Thus, the present invention is preferably directed to a method for producing cytidine 5'-monophospho-N-acetyl-neuraminic acid (CMP-Neu5Ac, 1)

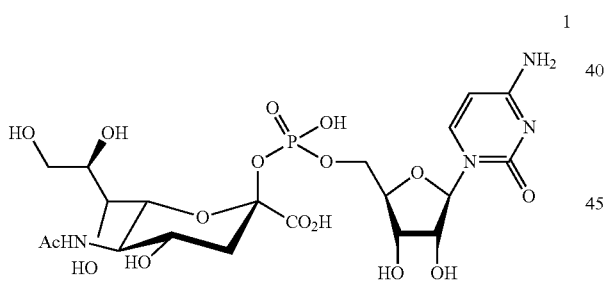

comprising:
A) providing a solution comprising N-acetyl-D-glucosamine, pyruvate, polyphosphate, cytidine, and adenosine 5'-triphosphate (ATP), and a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);
B) mixing said solution and said set of enzymes and reacting a resulting solution to produce cytidine 5'-monophospho-N-acetyl-neuraminic acid (CMP-Neu5Ac),
  wherein the uridine kinase (UDK) transfers in situ the cytidine to a cytidine monophosphate (CMP); and
  wherein the N-acylglucosamine 2-epimerase (AGE) comprises at least 80% of an amino acid sequence as set forth in SEQ ID NO: 1;
  the N-acetylneuraminate lyase (NAL) comprises at least 80% of an amino acid sequence as set forth in SEQ ID NO: 2;
  the N-acylneuraminate cytidylyltransferase (CSS) comprises at least 80% of an amino acid sequence as set forth in SEQ ID NO: 3;
  the uridine kinase (UDK) comprises at least 80% of an amino acid sequence as set forth in SEQ ID NO: 4;
  the uridine monophosphate kinase (URA6) comprises at least 80% of an amino acid sequence as set forth in SEQ ID NO: 5; and the polyphosphate kinase 3 (PPK3) comprises at least 80% of an amino acid sequence as set forth in SEQ ID NO: 6;
preferably,
  wherein the N-acylglucosamine 2-epimerase (AGE) comprises at least 85% of an amino acid sequence as set forth in SEQ ID NO: 1;
  the N-acetylneuraminate lyase (NAL) comprises at least 85% of an amino acid sequence as set forth in SEQ ID NO: 2;
  the N-acylneuraminate cytidylyltransferase (CSS) comprises at least 85% of an amino acid sequence as set forth in SEQ ID NO: 3;
  the uridine kinase (UDK) comprises at least 85% of an amino acid sequence as set forth in SEQ ID NO: 4;
  the uridine monophosphate kinase (URA6) comprises at least 85% of an amino acid sequence as set forth in SEQ ID NO: 5; and the polyphosphate kinase 3 (PPK3) comprises at least 85% of an amino acid sequence as set forth in SEQ ID NO: 6;
also preferably,
  wherein the N-acylglucosamine 2-epimerase (AGE) comprises at least 90% of an amino acid sequence as set forth in SEQ ID NO: 1;
  the N-acetylneuraminate lyase (NAL) comprises at least 90% of an amino acid sequence as set forth in SEQ ID NO: 2;
  the N-acylneuraminate cytidylyltransferase (CSS) comprises at least 90% of an amino acid sequence as set forth in SEQ ID NO: 3;
  the uridine kinase (UDK) comprises at least 90% of an amino acid sequence as set forth in SEQ ID NO: 4;
  the uridine monophosphate kinase (URA6) comprises at least 90% of an amino acid sequence as set forth in SEQ ID NO: 5; and the polyphosphate kinase 3 (PPK3) comprises at least 90% of an amino acid sequence as set forth in SEQ ID NO: 6;
more preferably,
  wherein the N-acylglucosamine 2-epimerase (AGE) comprises at least 95% of an amino acid sequence as set forth in SEQ ID NO: 1;
  the N-acetylneuraminate lyase (NAL) comprises at least 95% of an amino acid sequence as set forth in SEQ ID NO: 2;
  the N-acylneuraminate cytidylyltransferase (CSS) comprises at least 95% of an amino acid sequence as set forth in SEQ ID NO: 3;
  the uridine kinase (UDK) comprises at least 95% of an amino acid sequence as set forth in SEQ ID NO: 4;
  the uridine monophosphate kinase (URA6) comprises at least 95% of an amino acid sequence as set forth in SEQ ID NO: 5; and the polyphosphate kinase 3 (PPK3) comprises at least 95% of an amino acid sequence as set forth in SEQ ID NO: 6;
still more preferably, wherein the N-acylglucosamine 2-epimerase (AGE) comprises at least 98% of an amino acid sequence as set forth in SEQ ID NO: 1;
the N-acetylneuraminate lyase (NAL) comprises at least 98% of an amino acid sequence as set forth in SEQ ID NO: 2;
the N-acylneuraminate cytidylyltransferase (CSS) comprises at least 98% of an amino acid sequence as set forth in SEQ ID NO: 3;
the uridine kinase (UDK) comprises at least 98% of an amino acid sequence as set forth in SEQ ID NO: 4;
the uridine monophosphate kinase (URA6) comprises at least 98% of an amino acid sequence as set forth in SEQ ID NO: 5; and the polyphosphate kinase 3 (PPK3) comprises at least 98% of an amino acid sequence as set forth in SEQ ID NO: 6.

In one embodiment, the present invention is directed to a method for producing cytidine 5'-monophospho-N-acetyl-neuraminic acid (CMP-Neu5Ac, 1)

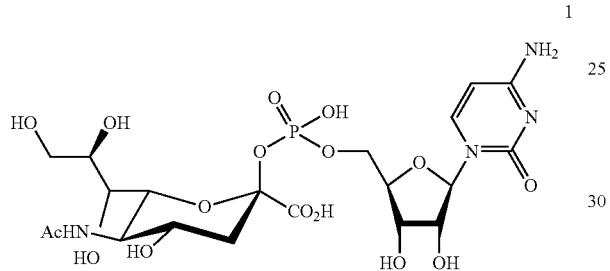

comprising:
A) providing a solution comprising N-acetyl-D-glucosamine, pyruvate, polyphosphate, cytidine, and adenosine 5'-triphosphate (ATP), and
a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);
B) mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine monophosphate (CMP); and
wherein the N-acylglucosamine 2-epimerase (AGE) comprises an amino acid sequence as set forth in SEQ ID NO: 1;
the N-acetylneuraminate lyase (NAL) comprises an amino acid sequence as set forth in SEQ ID NO: 2;
the N-acylneuraminate cytidylyltransferase (CSS) comprises an amino acid sequence as set forth in SEQ ID NO: 3;
the uridine kinase (UDK) comprises an amino acid sequence as set forth in SEQ ID NO: 4;
the uridine monophosphate kinase (URA6) comprises an amino acid sequence as set forth in SEQ ID NO: 5; and
the polyphosphate kinase 3 (PPK3) comprises an amino acid sequence as set forth in SEQ ID NO: 6. Preferably, the set of enzymes is co-immobilized on a solid support.

In case inorganic diphosphatase (PPA) is further applied, the present invention refers to a method for producing cytidine 5'-monophospho-N-acetyl-neuraminic acid (CMP-Neu5Ac, 1)

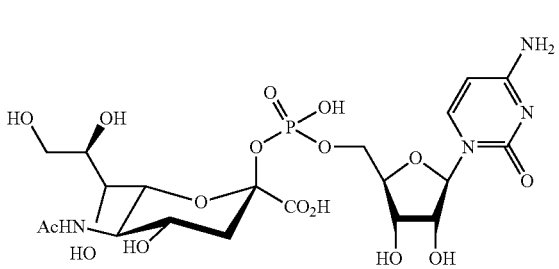

comprising:
A) providing a solution comprising N-acetyl-D-glucosamine, pyruvate, polyphosphate, cytidine, and adenosine 5'-triphosphate (ATP), and
a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase, a polyphosphate kinase 3 (PPK3), and an inorganic diphosphatase (PPA);
B) mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine monophosphate (CMP); and
wherein the N-acylglucosamine 2-epimerase (AGE) comprises an amino acid sequence as set forth in SEQ ID NO: 1;
the N-acetylneuraminate lyase (NAL) comprises an amino acid sequence as set forth in SEQ ID NO: 2;
the N-acylneuraminate cytidylyltransferase (CSS) comprises an amino acid sequence as set forth in SEQ ID NO: 3;
the uridine kinase (UDK) comprises an amino acid sequence as set forth in SEQ ID NO: 4;
the uridine monophosphate kinase (URA6) comprises an amino acid sequence as set forth in SEQ ID NO: 5;
the polyphosphate kinase 3 (PPK3) comprises an amino acid sequence as set forth in SEQ ID NO: 6; and
the inorganic diphosphatase (PPA) comprises an amino acid sequence as set forth in SEQ ID NO: 7. Preferably, the set of enzymes is co-immobilized on a solid support.

The regeneration of ATP can be enhanced by adding a 1-domain polyphosphate kinase (1D-PPK), which also catalyzes the phosphorylation of ADP to ATP, preferably a 1-domain polyphosphate kinase 2 (1D-PPK2) to the enzyme cascade of the inventive methods. Moreover, nucleoside phosphates, such as ADP are instable in aqueous media and tend to hydrolyze rapidly. To avoid the loss of ADP by hydrolysis to AMP, a 2-domain polyphosphate kinase (2D-PPK) which catalyzes the phosphorylation of AMP to ADP, preferably a 2-domain polyphosphate kinase 2 (2D-PPK2) can be added along with a 1D-PPK or alone to the inventive enzyme cascade.

In case inorganic diphosphatase (PPA), one-domain polyphosphate kinase 2 (1D-PPK2), and/or two-domain polyphosphate kinase 2 (2DPPK2) are further applied, the present invention refers to a method for producing cytidine 5'-monophospho-N-acetyl-neuraminic acid (CMP-Neu5Ac, 1)

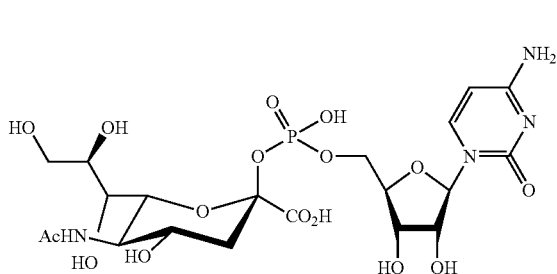

comprising:
A) providing a solution comprising N-acetyl-D-glucosamine, pyruvate, polyphosphate, cytidine, and adenosine 5'-triphosphate (ATP), and
a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase, a polyphosphate kinase 3 (PPK3), an inorganic diphosphatase (PPA), a one-domain polyphosphate kinase 2 (1 DPPK2) and/or a two-domain polyphosphate kinase 2 (2DPPK2);
B) mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine monophosphate (CMP);
wherein the N-acylglucosamine 2-epimerase (AGE) comprises an amino acid sequence as set forth in SEQ ID NO: 1;
the N-acetylneuraminate lyase (NAL) comprises an amino acid sequence as set forth in SEQ ID NO: 2;
the N-acylneuraminate cytidylyltransferase (CSS) comprises an amino acid sequence as set forth in SEQ ID NO: 3;
the uridine kinase (UDK) comprises an amino acid sequence as set forth in SEQ ID NO: 4;
the uridine monophosphate kinase (URA6) comprises an amino acid sequence as set forth in SEQ ID NO: 5;
the polyphosphate kinase 3 (PPK3) comprises an amino acid sequence as set forth in SEQ ID NO: 6;
the inorganic diphosphatase (PPA) comprises an amino acid sequence as set forth in SEQ ID NO: 7;
the two-domain polyphosphate kinase 2 (2DPPK2) comprises an amino acid sequence as set forth in SEQ ID NO: 8; and
the one-domain polyphosphate kinase 2 (1D-PPK2) comprises an amino acid sequence as set forth in SEQ ID NO: 9. Preferably, the set of enzymes is co-immobilized on a solid support.
Preferably, the reaction time of the method for producing cytidine 5'-monophospho-N-acetyl-neuraminic acid (CMP-Neu5Ac, 1) is in the range of 0.1 to 48 hours, preferred 0.2 to 35 hours, more preferred 0.5 to 30 hours, most referred 1 to 24 hours.

Preferably, during performing the method for producing cytidine 5'-monophospho-N-acetyl-neuraminic acid (CMP-Neu5Ac, 1), the resulting reaction solution is stirred with the range of 10 to 5000 rpms, preferred 50 to 2000 rpms, more preferred 100 to 1000 rpms, most referred 200 to 500 rpms.

Preferably, the set of enzymes is co-immobilized on a reusable, mechanically stable solid support thereby increasing or retaining a large fraction of the activity of each enzyme. Therefore, in the method of the present invention, the set of enzymes is preferably recycled.

Optionally, the set of enzymes is treated with a reducing agent such as DTT or 2-mercaptoethanol to retaining of the activity of each of enzymes after performing the method described herein.

In a further aspect of the present invention, the method for producing cytidine 5'-monophospho-N-acetyl-neuraminic acid comprises an additional step C):
C) isolating cytidine 5'-monophospho-N-acetyl-neuraminic acid (CMP-Neu5Ac) produced after the step B) by ion exchange chromatography or nanofiltration.

Preferably, ion-exchange chromatography is performed by using the formate form of anion-exchange resin such as Dowex 1×8. The column was eluted with a gradient of aqueous bicarbonate such as ammonium bicarbonate. The use of ammonium bicarbonate prevented hydrolysis of the extremely acid-labile CMP-Neu5Ac and provided it as the ammonium salt. Excess ammonium bicarbonate was easily removed by passing gel filtration column such as the Bio-Gel P-2.

Thus, the present invention refers to a method for producing cytidine 5'-monophospho-N-acetyl-neuraminic acid (CMP-Neu5Ac, 1)

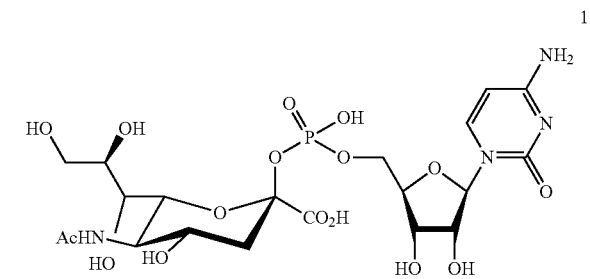

comprising:
A) providing a solution comprising N-acetyl-D-glucosamine, pyruvate, polyphosphate, cytidine, and adenosine 5'-triphosphate (ATP), and
a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);
B) mixing said solution and said set of enzymes and reacting a resulting solution to produce cytidine 5'-monophospho-N-acetyl-neuraminic acid (CMP-Neu5Ac),
C) isolating cytidine 5'-monophospho-N-acetyl-neuraminic acid (CMP-Neu5Ac) produced after the step B) by ion exchange chromatography;
wherein the uridine kinase (UDK) transfers in situ the cytidine to a cytidine monophosphate (CMP). Preferably, the set of enzymes is co-immobilized on a solid support.

Optionally, the method for producing cytidine 5'-monophospho-N-acetyl-neuraminic acid comprises an additional step C'):

C') drying the isolated cytidine 5'-monophospho-N-acetyl-neuraminic acid (CMP-Neu5Ac) obtained after the step C) by lyophilization.

Thus, the present invention refers to a method for producing cytidine 5'-monophospho-N-acetyl-neuraminic acid (CMP-Neu5Ac, 1)

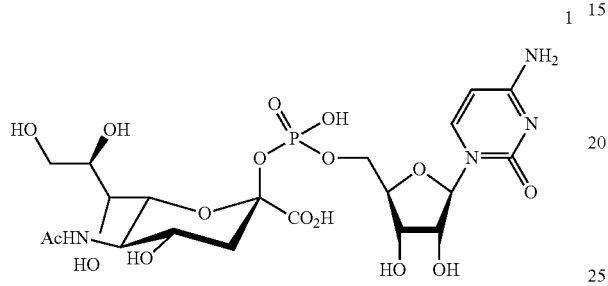

comprising:

A) providing a solution comprising N-acetyl-D-glucosamine, pyruvate, polyphosphate, cytidine, and adenosine 5'-triphosphate (ATP), and a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);

B) mixing said solution and said set of enzymes and reacting a resulting solution to produce cytidine 5'-monophospho-N-acetyl-neuraminic acid (CMP-Neu5Ac), C) isolating cytidine 5'-monophospho-N-acetyl-neuraminic acid (CMP-Neu5Ac) produced after the step B) by ion exchange chromatography;

C') drying the isolated cytidine 5'-monophospho-N-acetyl-neuraminic acid (CMP-Neu5Ac) obtained after the step C) by lyophilization, wherein the uridine kinase (UDK) transfers in situ the cytidine to a cytidine monophosphate (CMP). Preferably, the set of enzymes is co-immobilized on a solid support.

The excess amount of starting materials are also isolated in the step C) and directly reused for the reaction in the next reaction cycle. Preferably, N-acetyl-D-glucosamine and/or cytidine may be isolated and reused in the next reaction cycle.

Alternatively, N-acyl-glucosamine can be in situ formed from the substrates D-glucosamine, acetate. In this case the present invention is directed to a method for producing cytidine 5'-monophospho-N-acetyl-neuraminic acid (CMP-Neu5Ac, 1)

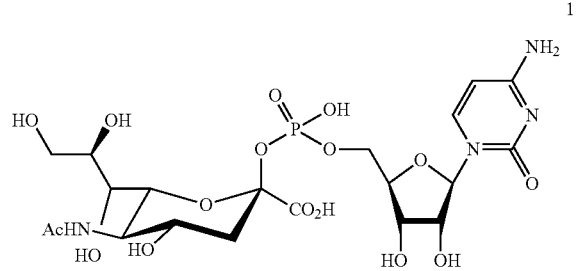

comprising:

A') providing a solution comprising D-glucosamine, acetate, pyruvate, polyphosphate, cytidine, and adenosine 5'-triphosphate (ATP), and a set of enzymes comprising an N-acetylglucosamine deacetylase, an N-acyl-glucosamine 2-epimerase (AGE), an N-acetylneuraminate lyase (NAL), an N-acetylneuraminate cytidylyltransferase (CSS), a uridine kinase (UDK), a uridine monophosphate kinase and a polyphosphate kinase 3 (PPK3);

B') mixing said solution and said set of enzymes and reacting a resulting solution to produce cytidine 5'-monophospho-N-acetyl-neuraminic acid (CMP-Neu5Ac), C) isolating cytidine 5'-monophospho-N-acetyl-neuraminic acid (CMP-Neu5Ac) produced after the step B') by ion exchange chromatography;

wherein the uridine kinase (UDK) transfers in situ the cytidine to a cytidine monophosphate (CMP). Preferably, the set of enzymes is co-immobilized on a solid support.

Optionally, the method for producing cytidine 5'-monophospho-N-acetyl-neuraminic acid comprises A') providing a solution comprising D-glucosamine, acetate, pyruvate, polyphosphate, cytidine, and adenosine 5'-triphosphate (ATP), and a set of enzymes comprising an N-acetylglucosamine deacetylase, an N-acyl-glucosamine 2-epimerase (AGE), an N-acetylneuraminate lyase (NAL), an N-acetylneuraminate cytidylyltransferase (CSS), a uridine kinase (UDK), a uridine monophosphate kinase and a polyphosphate kinase 3 (PPK3);

B') mixing said solution and said set of enzymes and reacting a resulting solution to produce cytidine 5'-monophospho-N-acetyl-neuraminic acid (CMP-Neu5Ac), C) isolating cytidine 5'-monophospho-N-acetyl-neuraminic acid (CMP-Neu5Ac) produced after the step B') by ion exchange chromatography;

C') drying the isolated cytidine 5'-monophospho-N-acetyl-neuraminic acid (CMP-Neu5Ac) obtained after the step C) by lyophilization, wherein the uridine kinase (UDK) transfers in situ the cytidine to a cytidine monophosphate (CMP). Preferably, the set of enzymes is co-immobilized on a solid support.

The inventive method for producing cytidine 5'-monophospho-N-acetyl-neuraminic acid (CMP-Neu5Ac) is preferably carried out with a set of co-immobilized enzymes. Thus, the present invention also is directed to a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3), wherein the set of enzymes is preferably co-immobilized on a solid support, more preferably a polymer functionalized with epoxy groups.

Preferably, said set of enzymes comprises:
the N-acylglucosamine 2-epimerase (AGE) comprises at least 80% of an amino acid sequence as set forth in SEQ ID NO: 1;
the N-acetylneuraminate lyase (NAL) comprises at least 80% of an amino acid sequence as set forth in SEQ ID NO: 2;
the N-acylneuraminate cytidylyltransferase (CSS) comprises at least 80% of an amino acid sequence as set forth in SEQ ID NO: 3;
the uridine kinase (UDK) comprises at least 80% of an amino acid sequence as set forth in SEQ ID NO: 4;
the uridine monophosphate kinase (URA6) comprises at least 80% of an amino acid sequence as set forth in SEQ ID NO: 5; and
the polyphosphate kinase 3 (PPK3) comprises at least 80% of an amino acid sequence as set forth in SEQ ID NO: 6,
wherein the set of enzymes is co-immobilized on a solid support, preferably a polymer functionalized with epoxy groups.

More preferably, said set of enzymes comprises:
the N-acylglucosamine 2-epimerase (AGE) comprises an amino acid sequence as set forth in SEQ ID NO: 1;
the N-acetylneuraminate lyase (NAL) comprises an amino acid sequence as set forth in SEQ ID NO: 2;
the N-acylneuraminate cytidylyltransferase (CSS) comprises an amino acid sequence as set forth in SEQ ID NO: 3;
the uridine kinase (UDK) comprises an amino acid sequence as set forth in SEQ ID NO: 4;
the uridine monophosphate kinase (URA6) comprises an amino acid sequence as set forth in SEQ ID NO: 5;
the polyphosphate kinase 3 (PPK3) comprises an amino acid sequence as set forth in SEQ ID NO: 6
wherein the set of enzymes is co-immobilized on a solid support, preferably a polymer functionalized with epoxy groups.

Optionally, the set of enzymes of the present invention further comprises an inorganic diphosphatase (PPA). In some embodiments, the set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3), and an inorganic diphosphatase (PPA), wherein the set of enzymes is co-immobilized on a solid support, preferably a polymer functionalized with epoxy groups.

Preferably, said set of enzymes comprises:
the N-acylglucosamine 2-epimerase (AGE) comprises at least 80% of an amino acid sequence as set forth in SEQ ID NO: 1;
the N-acetylneuraminate lyase (NAL) comprises at least 80% of an amino acid sequence as set forth in SEQ ID NO: 2;
the N-acylneuraminate cytidylyltransferase (CSS) comprises at least 80% of an amino acid sequence as set forth in SEQ ID NO: 3;
the uridine kinase (UDK) comprises at least 80% of an amino acid sequence as set forth in SEQ ID NO: 4;
the uridine monophosphate kinase (URA6) comprises at least 80% of an amino acid sequence as set forth in SEQ ID NO: 5;
the polyphosphate kinase 3 (PPK3) comprises at least 80% of an amino acid sequence as set forth in SEQ ID NO: 6; and
the inorganic diphosphatase (PPA) comprises at least 80% of an amino acid sequence as set forth in SEQ ID NO: 7
wherein the set of enzymes is co-immobilized on a solid support, preferably a polymer functionalized with epoxy groups.

Preferably, wherein the N-acylglucosamine 2-epimerase (AGE) comprises at least 85% of an amino acid sequence as set forth in SEQ ID NO: 1;
the N-acetylneuraminate lyase (NAL) comprises at least 85% of an amino acid sequence as set forth in SEQ ID NO: 2;
the N-acylneuraminate cytidylyltransferase (CSS) comprises at least 85% of an amino acid sequence as set forth in SEQ ID NO: 3;
the uridine kinase (UDK) comprises at least 85% of an amino acid sequence as set forth in SEQ ID NO: 4;
the uridine monophosphate kinase (URA6) comprises at least 85% of an amino acid sequence as set forth in SEQ ID NO: 5;
the polyphosphate kinase 3 (PPK3) comprises at least 85% of an amino acid sequence as set forth in SEQ ID NO: 6; and
the inorganic diphosphatase (PPA) comprises at least 85% of an amino acid sequence as set forth in SEQ ID NO: 7,
wherein the set of enzymes is co-immobilized on a solid support, preferably a polymer functionalized with epoxy groups.

Also preferably, wherein the N-acylglucosamine 2-epimerase (AGE) comprises at least 90% of an amino acid sequence as set forth in SEQ ID NO: 1;
the N-acetylneuraminate lyase (NAL) comprises at least 90% of an amino acid sequence as set forth in SEQ ID NO: 2;
the N-acylneuraminate cytidylyltransferase (CSS) comprises at least 90% of an amino acid sequence as set forth in SEQ ID NO: 3;
the uridine kinase (UDK) comprises at least 90% of an amino acid sequence as set forth in SEQ ID NO: 4;
the uridine monophosphate kinase (URA6) comprises at least 90% of an amino acid sequence as set forth in SEQ ID NO: 5;
the polyphosphate kinase 3 (PPK3) comprises at least 90% of an amino acid sequence as set forth in SEQ ID NO: 6; and
the inorganic diphosphatase (PPA) comprises at least 90% of an amino acid sequence as set forth in SEQ ID NO: 7;
wherein the set of enzymes is co-immobilized on a solid support, preferably a polymer functionalized with epoxy groups.

More preferably, wherein the N-acylglucosamine 2-epimerase (AGE) comprises at least 95% of an amino acid sequence as set forth in SEQ ID NO: 1; the N-acetylneuraminate lyase (NAL) comprises at least 95% of an amino acid sequence as set forth in SEQ ID NO: 2;
the N-acylneuraminate cytidylyltransferase (CSS) comprises at least 95% of an amino acid sequence as set forth in SEQ ID NO: 3;
the uridine kinase (UDK) comprises at least 95% of an amino acid sequence as set forth in SEQ ID NO: 4;

the uridine monophosphate kinase (URA6) comprises at least 95% of an amino acid sequence as set forth in SEQ ID NO: 5;

the polyphosphate kinase 3 (PPK3) comprises at least 95% of an amino acid sequence as set forth in SEQ ID NO: 6; and the inorganic diphosphatase (PPA) comprises at least 95% of an amino acid sequence as set forth in SEQ ID NO: 7;

wherein the set of enzymes is co-immobilized on a solid support, preferably a polymer functionalized with epoxy groups.

Still more preferably, wherein the N-acylglucosamine 2-epimerase (AGE) comprises at least 98% of an amino acid sequence as set forth in SEQ ID NO: 1;

the N-acetylneuraminate lyase (NAL) comprises at least 98% of an amino acid sequence as set forth in SEQ ID NO: 2;

the N-acylneuraminate cytidylyltransferase (CSS) comprises at least 98% of an amino acid sequence as set forth in SEQ ID NO: 3;

the uridine kinase (UDK) comprises at least 98% of an amino acid sequence as set forth in SEQ ID NO: 4;

the uridine monophosphate kinase (URA6) comprises at least 98% of an amino acid sequence as set forth in SEQ ID NO: 5;

the polyphosphate kinase 3 (PPK3) comprises at least 98% of an amino acid sequence as set forth in SEQ ID NO: 6; and the inorganic diphosphatase (PPA) comprises at least 98% of an amino acid sequence as set forth in SEQ ID NO: 7 wherein the set of enzymes is co-immobilized on a solid support, preferably a polymer functionalized with epoxy groups.

Most preferably, said set of enzymes comprises:
the N-acylglucosamine 2-epimerase (AGE) comprises an amino acid sequence as set forth in SEQ ID NO: 1;
the N-acetylneuraminate lyase (NAL) comprises an amino acid sequence as set forth in SEQ ID NO: 2;
the N-acylneuraminate cytidylyltransferase (CSS) comprises an amino acid sequence as set forth in SEQ ID NO: 3;
the uridine kinase (UDK) comprises an amino acid sequence as set forth in SEQ ID NO: 4;
the uridine monophosphate kinase (URA6) comprises an amino acid sequence as set forth in SEQ ID NO: 5;
the polyphosphate kinase 3 (PPK3) comprises an amino acid sequence as set forth in SEQ ID NO: 6; and
the inorganic diphosphatase (PPA) comprises an amino acid sequence as set forth in SEQ ID NO: 7
wherein the set of enzymes is co-immobilized on a solid support, preferably a polymer functionalized with epoxy groups.

Optionally, the set of enzymes of the present invention further comprises an inorganic diphosphatase (PPA), a one-domain polyphosphate kinase 2 (1D-PPK2) and/or a two-domain polyphosphate kinase 2 (2D-PPK2). In some embodiments, the set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3), an inorganic diphosphatase (PPA), a one-domain polyphosphate kinase 2 (1D-PPK2) and/or a two-domain polyphosphate kinase 2 (2D-PPK2), wherein the set of enzymes is co-immobilized on a solid support, preferably a polymer functionalized with epoxy groups.

Preferably, said set of enzymes comprises:
the N-acylglucosamine 2-epimerase (AGE) comprises at least 80% of an amino acid sequence as set forth in SEQ ID NO: 1;
the N-acetylneuraminate lyase (NAL) comprises at least 80% of an amino acid sequence as set forth in SEQ ID NO: 2;
the N-acylneuraminate cytidylyltransferase (CSS) comprises at least 80% of an amino acid sequence as set forth in SEQ ID NO: 3;
the uridine kinase (UDK) comprises at least 80% of an amino acid sequence as set forth in SEQ ID NO: 4;
the uridine monophosphate kinase (URA6) comprises at least 80% of an amino acid sequence as set forth in SEQ ID NO: 5;
the polyphosphate kinase 3 (PPK3) comprises at least 80% of an amino acid sequence as set forth in SEQ ID NO: 6;
the inorganic diphosphatase (PPA) comprises at least 80% of an amino acid sequence as set forth in SEQ ID NO: 7;
the two-domain polyphosphate kinase 2 (2DPPK2) comprises at least 80% of an amino acid sequence as set forth in SEQ ID NO: 8.
the one-domain polyphosphate kinase 2 (1D-PPK2) comprises at least 80% of an amino acid sequence as set forth in SEQ ID NO: 9,
wherein the set of enzymes is co-immobilized on a solid support, preferably a polymer functionalized with epoxy groups.

Preferably, said set of enzymes comprises:
the N-acylglucosamine 2-epimerase (AGE) comprises at least 85% of an amino acid sequence as set forth in SEQ ID NO: 1;
the N-acetylneuraminate lyase (NAL) comprises at least 85% of an amino acid sequence as set forth in SEQ ID NO: 2;
the N-acylneuraminate cytidylyltransferase (CSS) comprises at least 85% of an amino acid sequence as set forth in SEQ ID NO: 3;
the uridine kinase (UDK) comprises at least 85% of an amino acid sequence as set forth in SEQ ID NO: 4;
the uridine monophosphate kinase (URA6) comprises at least 85% of an amino acid sequence as set forth in SEQ ID NO: 5;
the polyphosphate kinase 3 (PPK3) comprises at least 85% of an amino acid sequence as set forth in SEQ ID NO: 6;
the inorganic diphosphatase (PPA) comprises at least 85% of an amino acid sequence as set forth in SEQ ID NO: 7;
the two-domain polyphosphate kinase 2 (2DPPK2) comprises at least 85% of an amino acid sequence as set forth in SEQ ID NO: 8.
the one-domain polyphosphate kinase 2 (1D-PPK2) comprises at least 85% of an amino acid sequence as set forth in SEQ ID NO: 9,
wherein the set of enzymes is co-immobilized on a solid support, preferably a polymer functionalized with epoxy groups.

Also preferably, said set of enzymes comprises:
the N-acylglucosamine 2-epimerase (AGE) comprises at least 90% of an amino acid sequence as set forth in SEQ ID NO: 1;

the N-acetylneuraminate lyase (NAL) comprises at least 90% of an amino acid sequence as set forth in SEQ ID NO: 2;

the N-acylneuraminate cytidylyltransferase (CSS) comprises at least 90% of an amino acid sequence as set forth in SEQ ID NO: 3;

the uridine kinase (UDK) comprises at least 90% of an amino acid sequence as set forth in SEQ ID NO: 4;

the uridine monophosphate kinase (URA6) comprises at least 90% of an amino acid sequence as set forth in SEQ ID NO: 5;

the polyphosphate kinase 3 (PPK3) comprises at least 90% of an amino acid sequence as set forth in SEQ ID NO: 6;

the inorganic diphosphatase (PPA) comprises at least 90% of an amino acid sequence as set forth in SEQ ID NO: 7;

the two-domain polyphosphate kinase 2 (2DPPK2) comprises at least 90% of an amino acid sequence as set forth in SEQ ID NO: 8.

the one-domain polyphosphate kinase 2 (1D-PPK2) comprises at least 90% of an amino acid sequence as set forth in SEQ ID NO: 9, wherein the set of enzymes is co-immobilized on a solid support, preferably a polymer functionalized with epoxy groups.

More preferably, said set of enzymes comprises:
the N-acylglucosamine 2-epimerase (AGE) comprises at least 95% of an amino acid sequence as set forth in SEQ ID NO: 1;

the N-acetylneuraminate lyase (NAL) comprises at least 95% of an amino acid sequence as set forth in SEQ ID NO: 2;

the N-acylneuraminate cytidylyltransferase (CSS) comprises at least 95% of an amino acid sequence as set forth in SEQ ID NO: 3;

the uridine kinase (UDK) comprises at least 95% of an amino acid sequence as set forth in SEQ ID NO: 4;

the uridine monophosphate kinase (URA6) comprises at least 95% of an amino acid sequence as set forth in SEQ ID NO: 5;

the polyphosphate kinase 3 (PPK3) comprises at least 95% of an amino acid sequence as set forth in SEQ ID NO: 6;

the inorganic diphosphatase (PPA) comprises at least 95% of an amino acid sequence as set forth in SEQ ID NO: 7;

the two-domain polyphosphate kinase 2 (2DPPK2) comprises at least 95% of an amino acid sequence as set forth in SEQ ID NO: 8.

the one-domain polyphosphate kinase 2 (1D-PPK2) comprises at least 95% of an amino acid sequence as set forth in SEQ ID NO: 9, wherein the set of enzymes is co-immobilized on a solid support, preferably a polymer functionalized with epoxy groups, Still more preferably, said set of enzymes comprises:
the N-acylglucosamine 2-epimerase (AGE) comprises at least 98% of an amino acid sequence as set forth in SEQ ID NO: 1;

the N-acetylneuraminate lyase (NAL) comprises at least 98% of an amino acid sequence as set forth in SEQ ID NO: 2;

the N-acylneuraminate cytidylyltransferase (CSS) comprises at least 98% of an amino acid sequence as set forth in SEQ ID NO: 3;

the uridine kinase (UDK) comprises at least 98% of an amino acid sequence as set forth in SEQ ID NO: 4;

the uridine monophosphate kinase (URA6) comprises at least 98% of an amino acid sequence as set forth in SEQ ID NO: 5;

the polyphosphate kinase 3 (PPK3) comprises at least 98% of an amino acid sequence as set forth in SEQ ID NO: 6;

the inorganic diphosphatase (PPA) comprises at least 98% of an amino acid sequence as set forth in SEQ ID NO: 7;

the two-domain polyphosphate kinase 2 (2DPPK2) comprises at least 98% of an amino acid sequence as set forth in SEQ ID NO: 8.

the one-domain polyphosphate kinase 2 (1D-PPK2) comprises at least 98% of an amino acid sequence as set forth in SEQ ID NO: 9, wherein the set of enzymes is co-immobilized on a solid support, preferably a polymer functionalized with epoxy groups.

Most preferably, said set of enzymes comprises:
the N-acylglucosamine 2-epimerase (AGE) comprises an amino acid sequence as set forth in SEQ ID NO: 1;

the N-acetylneuraminate lyase (NAL) comprises an amino acid sequence as set forth in SEQ ID NO: 2;

the N-acylneuraminate cytidylyltransferase (CSS) comprises an amino acid sequence as set forth in SEQ ID NO: 3;

the uridine kinase (UDK) comprises an amino acid sequence as set forth in SEQ ID NO: 4;

the uridine monophosphate kinase (URA6) comprises an amino acid sequence as set forth in SEQ ID NO: 5;

the polyphosphate kinase 3 (PPK3) comprises an amino acid sequence as set forth in SEQ ID NO: 6; and the inorganic diphosphatase (PPA) comprises an amino acid sequence as set forth in SEQ ID NO: 7.

the two-domain polyphosphate kinase 2 (2DPPK2) comprises an amino acid sequence as set forth in SEQ ID NO: 8.

the one-domain polyphosphate kinase 2 (1D-PPK2) comprises an amino acid sequence as set forth in SEQ ID NO: 9, wherein the set of enzymes is co-immobilized on a solid support, preferably a polymer functionalized with epoxy groups.

Optionally, any set of enzymes as mentioned above further comprises an N-acetyl-glucosamine deacetylase.

The enzymes are then immobilized on a solid support such that they retain their activity, substrate specificity, stereoselectivity and/or other properties. Suitable solid supports are for instance beads, monoliths, spheres, particles, a particle bed, a fiber mat, granules, a gel, a membrane, a hollow-fiber membrane, a mixed-matrix membrane, a surface or other solid phase material.

Surprisingly it has been found that co-immobilization of the set of enzymes results in a higher productivity in the production of cytidine 5'-monophospho-N-acetylneuraminic acid (CMP-Neu5Ac) compared to non-immobilized or separately immobilization of the enzymes. Thus, preferably the enzymes used in the inventive methods described herein are co-immobilized on a solid support.

Methods of enzyme immobilization are well-known in the art. The enzymes can be bound non-covalently or covalently, such as adsorption, covalent binding, ionic binding, metal binding, crosslinking or crystallization. Various methods for conjugation and immobilization of enzymes to solid supports (e.g., resins, membranes, beads, glass, etc.) are well known in the art and described in e.g.: Yi et al., Process Biochemistry 2007, 42, 895; Martin et al., Applied Microbiology and Biotechnology 2007, 76, 843; Koszelewski et al., Journal of Molecular Catalysis B: Enzymatic, 2010, 63, 39; Truppo et al., Org. Process Res. Dev., 2011, 15, 1033; Hermanson, G. T., Bioconjugate Techniques, Second Edition, Academic Press (2008); Mateo et al., Biotechnology Progress, 2002, 18, 629; and Bioconjugation Protocols: Strategies and Methods, In Methods in Molecular Biology, C. M. Niemeyer ed., Humana Press (2004).

The enzymes used in the inventive methods described herein, namely an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3), the inorganic diphosphatase (PPA), 1-domain polyphosphate kinase 2 (1DPPK2), 2-domain polyphosphate kinase 2 (2DPPK2), and pyrophosphatase are well known to the skilled person and can be obtained by any method well known to the skilled person in the art.

Particularly, the enzymes can be overexpressed in, isolated from or prepared by recombinant methods from microbiological cultures comprising bacterial cultures, such as *E. coli*, virus and phage cultures and eukaryotic cell cultures. The inventive methods described herein are not restricted to enzymes from the sources described in the experimental section. Thus, the inventive method can be performed with the above listed enzymes obtained from various sources using common protein expression or isolation techniques. Further, it is well known to the skilled person to adapt the preparation of the enzymes to the specific applications in which the method is used. For instance, the above listed enzymes can be expressed in *E. coli* by using bacterial growth media of non-animal origin, such as a Luria-Bertani broth comprising tryptone from soy.

The enzyme-containing solutions obtained from cell homogenization or cell lysis, which are usually centrifuged and filtered to remove cell debris, can be directly used for immobilizing the enzymes on a solid support. Thus, no further purification step or isolation step is required and the crude cell lysate or cell homogenate can be used for immobilizing the enzymes on a solid support such that they retain their activity, substrate specificity, stereoselectivity and/or other properties.

Solid supports useful for immobilizing the enzymes used in the method of the present invention include but are not limited to beads, monoliths, spheres, particles, a particle bed, a fiber mat, granules, a gel, a membrane, a hollow-fiber membrane, a mixed-matrix membrane or a surface. Preferably, the solid support has the form of beads.

In particular, the solid support is composed of beads or resins comprising a polymer with epoxide functional groups, with amino epoxide functional groups, with ethylenediamine functional groups, with amino C2 functional groups, with amino C6 functional groups, with anionic/amino C6 spacer functional groups. Preferably, the solid support is composed of porous beads having a pore size of 0.1 Å to 100000 Å.

Particularly preferred are solid supports that are functionalized with epoxy functional groups. Further preferred solid supports include, but are not limited to solid supports with ethylenediamine functional groups, with epoxy functional groups and further functionalized with a hydrophobic group, such as butyl, octyl, methyl, phenyl, for example with epoxide functional groups and butyl functional groups, with amino C2 spacer functional groups, with amino C6 spacer functional groups, or other amino spacer such as amino C3 spacer, amino C4 spacer, amino C5 spacer, amino C7 spacer, with epoxy functional groups, with anionic/amino C6 spacer functional groups, with anionic/tertiary amine functional groups, anionic/quaternary amine functional groups, with cationic/sulphonic functional groups, with carboxylic ester functional groups, with phenyl functional groups, with octadecyl functional groups, with styrene/methyl functional groups, macroporous resins or beads. The solid support may consist of a polymeric material, non-polymeric material, e.g. silica gel. The solid support may consists of a polymeric material including, but not limited to polymethacrylate, polyacrylic acid, acrylic polymer, polystyrene, styrene, styrene/methacrylate and mixtures thereof.

Examples of solid supports useful for immobilizing the enzymes used in the method of the present invention include but are not limited to beads or resins comprising polymethacrylate with epoxide functional groups, polymethacrylate with amino epoxide functional groups, polymethacrylate with ethylenediamine functional groups, polymethacrylate with epoxide functional groups and further functionalized with a hydrophobic group, such as butyl, octyl, methyl, phenyl, for example polymethacrylate with epoxide functional groups and butyl functional groups, polymethacrylate with amino C2 spacer functional groups, polymethacrylate with amino C6 spacer functional groups, polyacrylic acid with epoxy functional groups, acrylic polymer with epoxy functional groups polyacrylic acid with anionic/amino C6 spacer functional groups, polyacrylic acid with anionic/tertiary amine functional groups, polystyrene with anionic/quaternary amine functional groups, polystyrene with cationic/sulphonic functional groups, polyacrylic acid with carboxylic ester functional groups, polystyrene with phenyl functional groups, polymethacrylate with octadecyl functional groups, polystyrene with styrene/methyl functional groups, magnetic silica particles with Ni-NTA functional group, or magnetic nanoparticles with a core of magnetite and a dextran shell with Ni-NTA functional group, macroporous resins or beads of macroporous styrene or styrene/methacrylate. While, in principle, any suitable solid support known in the art can be used in the inventive method, Ni agarose beads or Ni NTA agarose resins are not preferred for the reasons as set forth above. Exemplary solid supports useful for immobilizing the enzymes used in the inventive method include, but are not limited to, Sepabeads/ReliZyme (Resindion): EC-EP, including EC-EP/S and EC-EP/M, EP403/M, EP403/S HFA403M, HFA403S, HG403, EP400/SS EC-HG, EC-HFA, EC-EA/M, EA403/S and EC-HA including EC-HA/S and EC-HA/M; Immobeads (ChiralVision) Imm150P, IB-COV1, IB-COV2, IB-COV3, IB-AN11, IB-AN12, IB-AN13, IB-AN14, IB-CAT1, IB-ADS1, IB-ADS2, IB-ADS3 and IB-ADS4, IB-CAT-1, IB-ANI-1, IB-ANI-2, IB-ANI-3, IB-ANI-4; Eupergit (Rohm GmbH & Co. KG) and magnetic particles (micromod GmbH): Nano-mag, Sicastar-6 and Sicastar-1.5, enzyme immobilization resins Lifetech™ (Purolite): Epoxy methacrylate: ECR8215, ECR8215F, ECR8215M, ECR8206, ECR8206F, ECR8206M, ECR8204, ECR8204F, ECR8204M, ECR8209, ECR8209F, ECR8209M, ECR8285, ECR8285F, ECR8285M, Amino C2 or C6 methacrylate: ECR8305, ECR8305F, ECR8305M, ECR8309, ECR8309F, ECR8309M, ECR8315, ECR8315F, ECR8315M, ECR8404 ECR8404F, ECR8404M, ECT8409, ECT8409F, ECT8409M, ECR8415, ECR8415F, ECR8415M, macroporous resins ECR1090, ECR1091, ECR1091M, ECR1061, ECR1030, ECR1030F, ECR8806F; ionic resins ECR1504, ECR1508, ECR1604, ECR1640, and magnetic particles (micromod GmbH): Nano-mag-D and Sicastar-M-CT.

Solid support materials which result in mechanically stable beads or resins with enzymes immobilized thereon are preferred with regard to reuse and/or recycling of the beads or resins for the production of CMP-Neu5Ac and more preferred with regard to a continuous process of the method for production of CMP-Neu5Ac. A mechanically stable solid support is characterized in resistance to abrasion, mechanical stress and is suitable for a high number of cycles, such as at least 10, more preferably at least 12, more preferably at least 14, more preferably at least 16, more preferably at least 18, and most preferably at least 20 cycles. It could be shown that immobilization of enzymes through covalent binding to a solid support provides mechanically stable beads or resins, which has been shown to be particularly suitable for reuse and/or recycling of the resins or beads with immobilized enzymes for the production of CMP-Neu5Ac.

Surprisingly it has been found that with beads or resins comprising a polymer with epoxide functional groups, such as for example, but not limited to polymethacrylate with epoxide functional groups, polymethacrylate with amino epoxide functional groups, polymethacrylate with ethylenediamine functional groups, polymethacrylate with epoxide functional groups and butyl functional groups polyacrylic acid with epoxy functional groups, acrylic polymer with epoxy functional groups, that allow covalent binding of the enzymes to be immobilized, mechanically robust resins or beads may be obtained.

Thus, reusable, mechanically stable solid support in form of beads or resins with enzymes immobilized thereon are preferred with regard to co-immobilization of the set of enzymes from crude cell lysate or crude cell homogenate, and with regard to retaining larges parts of or increasing the activity of all enzymes co-immobilized and with regard to reuse and/or recycling of the beads or resins for the production of CMP-Neu5Ac and with regard to a continuous process of the method for production of CMP-Neu5Ac. The solid supports are inter alia characterized in resistance to abrasion, mechanical stress and are suitable for a high number of cycles, such as at least 10, more preferably at least 12, more preferably at least 14, more preferably at least 16, more preferably at least 18, and most preferably at least 20 cycles. It could be shown that immobilization of enzymes through covalent binding to a solid support provides mechanically robust beads or resins, which has been shown to be particularly suitable for reuse and/or recycling of the resins or beads with immobilized enzymes for the production of CMP-Neu5Ac, which allows the co-immobilization of the set of enzymes from crude cell lysate and which retains large parts of or increases the activity of all enzymes co-immobilized. Surprisingly it has been found that with beads or resins comprising epoxide functional groups, amino epoxide functional groups, ethylenediamine functional groups, or epoxide functional groups and a hydrophobic group, such as butyl, octyl, methyl, phenyl, butyl functional groups that allow covalent binding of the enzymes to be immobilized, robust solid resins or beads may be obtained.

Epoxy-activated resins or beads allow multipoint covalent binding between an enzyme and the resin or bead. Preferably the resin backbone is composed of methacrylate with porosities of 0.01 nm to 10000 nm or 0.1 Å to 100000 Å. In a preferred embodiment the porosity of an epoxy functionalized resin or bead, for example an epoxy methacrylate resin or bead, may be 30 nm to 60 nm. In a preferred embodiment the porosity of an epoxy methacrylate resin or bead may be 40 nm to 60 nm. In a preferred embodiment the porosity of an epoxy functionalized resin or bead, for example an epoxy methacrylate resin or bead, may be 50 nm to 60 nm. In a preferred embodiment the porosity of an epoxy functionalized resin or bead, for example an epoxy methacrylate resin or bead, may be 60 nm to 120 nm. In a preferred embodiment the porosity of an epoxy functionalized resin or bead, for example an epoxy methacrylate resin or bead, may be 120 nm to 180 nm. The epoxy functionalized resin or bead, for example an epoxy methacrylate resin or bead, may form very stable covalent linkages with different protein groups, such as amino, thiol, phenolic, preferably under very mild pH and temperature conditions. The resins are preferably mechanically stable and the resin with immobilized enzymes may be preferably used in a stirred tank or column reactor.

Amino resins, such as amino C2 functionalized resins or amino C6 functionalized resins or other amino resins such as amino C3, amino C4, amino C5, amino C7 and so on, such as for example but not limited to amino C2 methacrylate resins or amino C6 methacrylate resins may pre-activated, for example by glutaraldehyde and then used in the covalent immobilization of enzyme. Reaction of the aldehyde groups with amino groups of enzymes form Schiff bases which results in multipoint covalent binding. A linkage may be also achieved by reduction with borohydrides. Thus a reversible immobilization may become irreversible by means of cross-linking step: the enzyme may be adsorbed onto the carrier and then crosslinked by using, for example, glutaraldehyde. The crosslinked enzyme or the crosslinked enzyme may cover the carrier like a net. Amino functionalized resins, such as amino C2 methacrylate resins or amino C6 methacrylate resins have preferably porosities in the range of 30 nm to 180 nm or 300 Å to 1800 Å. In a preferred embodiment the porosity of an amino functionalized resin, such as amino C2 methacrylate resin or bead or of an amino C6 methacrylate resin or bead may be 30 nm to 60 nm. In a preferred embodiment the porosity of an amino functionalized resin, such as an amino C2 methacrylate resin or bead or of an amino C6 methacrylate resin or bead may be 60 nm to 120 nm. In a preferred embodiment the porosity of an amino functionalized resin, such as an amino C2 methacrylate resin or bead or of an amino C6 methacrylate resin or bead may be 120 nm to 180 nm.

Another method for irreversible immobilization is the activation of hydroxyl functional groups, such as for example for 1,2-diol-functionalized resins or beads.

Thus, particularly preferred are beads or resins comprising polymethacrylate with epoxide functional groups and polymethacrylate with amino epoxide functional groups. Preferably the beads or resins comprising polymethacrylate with epoxide functional groups are hydrophilic. Covalent enzyme immobilization is particularly preferred. In preferred embodiments the beads or resins are not functionalized with apolar groups such as butyl or octadecyl groups. In preferred embodiments the resins or beads are hydrophilic.

Preferably, the methacrylate polymer has the form of beads. Preferably, the beads have a particle size in the range of 150 μm-300 μm. Preferably, the methacrylate polymer is porous with a pore diameter between 600 Å-1200 Å. In one embodiment, the methacrylate polymer is of low porosity having a pore diameter between 300 Å-600 Å. In one embodiment, the methacrylate polymer is of low porosity having a pore diameter between 450 Å-650 Å. In one embodiment, the methacrylate polymer is of high porosity having a pore diameter between 1200 Å-1800 Å. In one embodiment, the methacrylate polymer is further functionalized with butyl groups. In one embodiment, the methacrylate polymer is further functionalized with a hydrophobic group such as butyl, methyl, phenyl, octyl.

Preferably, the solid support is composed of a resin or beads selected from: sepabeads (Resindion): EC-EP, EP403/M, EP403/S, HFA403, EA403, HA403, EC-EA/M and EC-HA; immobeads (ChiralVision) IB-COV1, IB-COV2, IB-COV3, IB-AN11, IB-AN11, IB-CAT1; Eupergit® (R6hm GmbH & Co. KG), enzyme immobilization resins (Purolite): Epoxy methacrylate: ECR8215, ECR8215F, ECR8215M, ECR8206, ECR8206F, ECR8206M, ECR8204, ECR8204F, ECR8204M, ECR8209, ECR8209F, ECR8209M, ECR8285, ECR8285F, ECR8285M, Amino C2 or C6 methacrylate: ECR8305, ECR8305F, ECR8305M, ECR8309, ECR8309F, ECR8309M, ECR8315, ECR8315F, ECR8315M, ECR8404 ECR8404F, ECR8404M, ECT8409, ECT8409F, ECT8409M, ECR8415, ECR8415F, ECR8415M.

Preferably, the solid support is composed of a resin or beads selected from: sepabeads (Resindion): EC-EP, EP403, EP403/M, EP403/S, EC-HFA, HFA403, HFA403/M, HFA 403/S, immobeads (ChiralVision) IB-COV2, IB-COV3, (Purolite) ECR8215, ECR8215F, ECR8215M, ECR8204F, ECR8204M, ECR8204, ECR8209F, ECR8209M, ECR8209; Eupergit® (R6hm GmbH & Co. KG).

Thus, the present invention is directed to a method for producing cytidine 5'-monophospho-N-acetyl-neuraminic acid (CMP-Neu5Ac, 1)

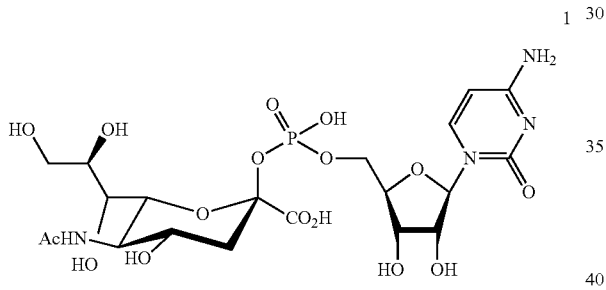

1 comprising:
A) providing a solution comprising N-acetyl-D-glucosamine, pyruvate, polyphosphate, cytidine, and adenosine 5'-triphosphate (ATP), and
 a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);
B) mixing said solution and said set of enzymes and reacting a resulting solution to produce cytidine 5'-monophospho-N-acetyl-neuraminic acid (CMP-Neu5Ac),
wherein the set of enzymes is co-immobilized on a solid support, the solid support is composed of a resin or beads selected from sepabeads (Resindion): EC-EP, EP403, EP403/M, EP403/S, EC-HFA, HFA403, HFA403/M, HFA 403/S, immobeads (ChiralVision) IB-COV2, IB-COV3, (Purolite) ECR8215, ECR8215F, ECR8215M, ECR8204F, ECR8204M, ECR8204, ECR8209F, ECR8209M, ECR8209; Eupergit®; and the uridine kinase (UDK) transfers in situ the cytidine to a cytidine monophosphate (CMP).

Thus, the present invention is further directed to a method for producing cytidine 5'-monophospho-N-acetyl-neuraminic acid (CMP-Neu5Ac, 1)

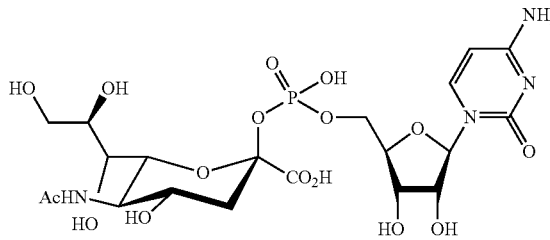

1 comprising:
A) providing a solution comprising N-acetyl-D-glucosamine, pyruvate, polyphosphate, cytidine, and adenosine 5'-triphosphate (ATP), and
 a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase, a polyphosphate kinase 3 (PPK3), and an inorganic diphosphatase (PPA);
B) mixing said solution and said set of enzymes and reacting a resulting solution to produce cytidine 5'-monophospho-N-acetyl-neuraminic acid (CMP-Neu5Ac),
wherein the set of enzymes is co-immobilized on a solid support; the set of enzymes is co-immobilized on a solid support, the solid support is composed of a resin or beads selected from sepabeads (Resindion): EC-EP, EP403, EP403/M, EP403/S, EC-HFA, HFA403, HFA403/M, HFA 403/S, immobeads (ChiralVision) IB-COV2, IB-COV3, (Purolite) ECR8215, ECR8215F, ECR8215M, ECR8204F, ECR8204M, ECR8204, ECR8209F, ECR8209M, ECR8209; Eupergit (R6hm GmbH & Co. KG); and the uridine kinase (UDK) transfers in situ the cytidine to a cytidine monophosphate (CMP).

Thus, the present invention is further directed to a method for producing cytidine 5'-monophospho-N-acetyl-neuraminic acid (CMP-Neu5Ac, 1)

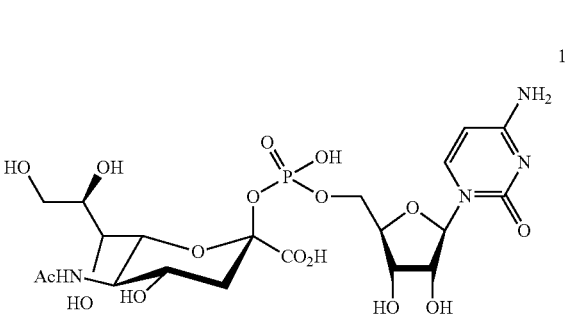

1 comprising:
A) providing a solution comprising N-acetyl-D-glucosamine, pyruvate, polyphosphate, cytidine, and adenosine 5'-triphosphate (ATP), and
 a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase, a polyphosphate kinase 3 (PPK3), an inorganic diphosphatase (PPA), a one-domain polyphosphate kinase 2 (1DPPK2) and/or a two-domain polyphosphate kinase 2 (2DPPK2);

B) mixing said solution and said set of enzymes and reacting a resulting solution to produce cytidine 5'-monophospho-N-acetyl-neuraminic acid (CMP-Neu5Ac), wherein the set of enzymes is co-immobilized on a solid support; the set of enzymes is co-immobilized on a solid support, the solid support is composed of a resin or beads selected from sepabeads (Resindion): EC-EP, EP403, EP403/M, EP403/S, EC-HFA, HFA403, HFA403/M, HFA 403/S, immobeads (ChiralVision) IB-COV2, IB-COV3, (Purolite) ECR8215, ECR8215F, ECR8215M, ECR8204F, ECR8204M, ECR8204, ECR8209F, ECR8209M, ECR8209; Eupergit (R6hm GmbH & Co. KG); and the uridine kinase (UDK) transfers in situ the cytidine to a cytidine monophosphate (CMP).

Preferably the enzymes are co-immobilized on a polymer functionalized with epoxy groups which may be used in reactors in multiple runs or cycles. Preferably the enzymes co-immobilized on a solid support may be used in at least 3 cycles, more preferably in at least 4 cycles, more preferably in at least 5 cycles, more preferably in at least 6 cycles, more preferably in at least 7 cycles, more preferably in at least 8 cycles, more preferably in at least 9 cycles, more preferably in at least 10 cycles, more preferably in at least 12 cycles, more preferably in at least 14 cycles, more preferably in at least 16 cycles, more preferably in at least 18 cycles, more preferably in at least 20 cycles, more preferably in at least 25 cycles, more preferably in at least 25 cycles, more preferably in at least 30 cycles, and most preferably in at least 50 cycles. Preferably the enzymes are co-immobilized on a solid support and may be used in at least 3-10, preferably 5-12, more preferably 7-14, more preferably 9-16 and even more preferably at least 10-20 runs or cycles.

In preferred embodiments, epoxy beads or resin with co-immobilized set of enzymes, allow in general CMP-Neu5Ac synthesis in more than 3 cycles, preferably more than 5 cycles, preferably more than 10 cycles, and preferably even more than 20 cycles. The synthesis of CMP-Neu5Ac in such a large number of cycles is a significant improvement of the process and has not been reported before in the prior art.

A further aspect of the present invention is directed to a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3), wherein the set of enzymes is co-immobilized on a solid support, and the solid support is composed of a resin or beads selected from sepabeads (Resindion): EC-EP, EP403, EP403/M, EP403/S, EC-HFA, HFA403, HFA403/M, HFA 403/S, immobeads (ChiralVision) IB-COV2, IB-COV3, (Purolite) ECR8215, ECR8215F, ECR8215M, ECR8204F, ECR8204M, ECR8204, ECR8209F, ECR8209M, ECR8209; Eupergit (R6hm GmbH & Co. KG); and the uridine kinase (UDK) transfers in situ the cytidine to a cytidine monophosphate (CMP).

A further aspect of the present invention is also directed to a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3), an inorganic diphosphatase (PPA), wherein the set of enzymes is co-immobilized on a solid support, and the solid support is composed of a resin or beads selected from sepabeads (Resindion): EC-EP, EP403, EP403/M, EP403/S, EC-HFA, HFA403, HFA403/M, HFA 403/S, immobeads (ChiralVision) IB-COV2, IB-COV3, (Purolite) ECR8215, ECR8215F, ECR8215M, ECR8204F, ECR8204M, ECR8204, ECR8209F, ECR8209M, ECR8209; Eupergit (R6hm GmbH & Co. KG); and the uridine kinase (UDK) transfers in situ the cytidine to a cytidine monophosphate (CMP).

A further aspect of the present invention is also directed to a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3), an inorganic diphosphatase (PPA), a one-domain polyphosphate kinase 2 (1 DPPK2) and/or a two-domain polyphosphate kinase 2 (2DPPK2), wherein the set of enzymes is co-immobilized on a solid support, and the solid support is composed of a resin or beads selected from sepabeads (Resindion): EC-EP, EP403, EP403/M, EP403/S, EC-HFA, HFA403, HFA403/M, HFA 403/S, immobeads (ChiralVision) IB-COV2, IB-COV3, (Purolite) ECR8215, ECR8215F, ECR8215M, ECR8204F, ECR8204M, ECR8204, ECR8209F, ECR8209M, ECR8209; Eupergit (R6hm GmbH & Co. KG); and the uridine kinase (UDK) transfers in situ the cytidine to a cytidine monophosphate (CMP).

The present invention also refers to a method for producing a Neu5Acylated i.e. sialylated biomolecule comprising
i) performing the method as mentioned above to obtain CMP-Neu5Ac,
ii) reacting the CMP-Neu5Ac obtained after step i) with a biomolecule,
wherein the biomolecule is a saccharide, a glycopeptide, a glycoprotein, a glycolipid, a glycan, a peptide, a protein, an antibody, an antibody drug conjugate, a carbohydrate conjugate vaccine, or a flavonoid by forming an O-glycosidic bond with an hydroxyl group of the biomolecule with removal of CMP group in the presence of a sialyltransferase.

Sialyltransferases (EC 2.4.99) belong to glycosyltransferase family 29 (CAZY GT_29) which comprises enzymes with a number of known activities. There are about twenty different sialyltransferases which can be distinguished on the basis of the acceptor structure on which they act and on the type of sugar linkage they form. For example, a group of sialyltransferases adds sialic acid with an alpha-2,3 linkage to galactose, while other sialyltransferases add sialic acid with an alpha-2,6 linkage to galactose (Gal) or N-acetylgalactosamine (GalNAc). A peculiar type of sialyltransferases add sialic acid to other sialic acid units with an α-2,8 linkage, forming structures referred to as polysialic acid. As occurs for other glycosyl-transferases, the expression of sialyltransferases undergoes profound modifications during cell differentiation and neoplastic transformation; in some cases such changes induce phenotypic alterations.

Preferably, the sialyltransferase is selected from beta-galactosamide alpha-2,6-sialyltransferase (EC 2.4.99.1), alpha-N-acetylgalactosaminide alpha-2,6-sialyltransferase (EC 2.4.99.3), beta-galactoside alpha-2,3-sialyltransferase (EC 2.4.99.4), N-acetyllactosaminide alpha-2,3-sialyltransferase (EC 2.4.99.6), alpha-N-acetyl-neuraminide alpha-2,8-sialyltransferase (EC 2.4.99.8); and lactosylceramide alpha-2,3-sialyltransferase (EC 2.4.99.9). These enzymes use the CMP-Neu5Ac as a glycosyl donor.

Therefore, the present invention also refers to a method for producing a Neu5Acylated i.e. sialylated biomolecule comprising i) performing the method as mentioned above to obtain CMP-Neu5Ac,
ii) reacting the CMP-Neu5Ac obtained after step i) with a biomolecule, wherein the biomolecule is a saccharide, a glycopeptide, a glycoprotein, a glycolipid, a glycan, a peptide, a protein, an antibody, an antibody drug conjugate, a carbohydrate conjugate vaccine, virus, virus like particles, virus vaccine, or a flavonoid by forming an O-glycosidic bond with an hydroxyl group of the biomolecule with removal of CMP group in the presence of a sialyltransferase, and the sialyltransferase is selected from the group consisting of: beta-galactosamide alpha-2,6-sialyltransferase (EC 2.4.99.1), alpha-N-acetylgalactosaminide alpha-2,6-sialyltransferase (EC 2.4.99.3), beta-galactoside alpha-2,3-sialyltransferase (EC 2.4.99.4), N-acetyllactosaminide alpha-2,3-sialyltransferase (EC 2.4.99.6), alpha-N-acetyl-neuraminide alpha-2,8-sialyltransferase (EC 2.4.99.8); and lactosylceramide alpha-2,3-sialyltransferase (EC 2.4.99.9).

Furthermore, in some embodiments, the biomolecule contains any of galactoside (Gal), galactosaminide (GalN), N-acetylgalactosaminide (GalNAc), neuraminide, N-acetyl neuraminide (Neu5Ac), N-glycolylneuraminide, 3-Deoxy-D-glycero-D-galacto-2-nonulosonic Acid (KDN), and N-acetyllacosaminide (Gal-β-1-3-GlcNAc) moiety as terminal end group.

More preferred, the biomolecule is glycopeptide, glycoprotein, or antitumor vaccine which comprises T-antigen (Gal-β-1-3-GalNAc-α-1-O—) or Tn-antigen (GalNAc-α-1-O—); or glycolipid comprising Gal-β-1-4-GlcNAc-β-1-O—.

Therefore, the present invention also refers to a method for producing a Neu5Acylated i.e. sialylated biomolecule comprising
i) performing the method as mentioned above to obtain CMP-Neu5Ac,
ii) reacting the CMP-Neu5Ac obtained after step i) with a biomolecule, wherein the biomolecule is a saccharide, a glycopeptide, a glycoprotein, a glycolipid, a glycan, a peptide, a protein, an antibody, an antibody drug conjugate, a carbohydrate conjugate vaccine, virus, virus like particles, virus vaccine, or a flavonoid by forming an O-glycosidic bond with an hydroxyl group of the biomolecule with removal of CMP group in the presence of a sialyltransferase, and the biomolecule contains any of galactoside (Gal), galactosaminde (GalN), N-acetylgalactosaminide (GalNAc), neuraminide, N-acetyl neuraminide (Neu5Ac), N-glycolylneuraminide, 3-Deoxy-D-glycero-D-galacto-2-nonulosonic Acid (KDN), and N-acetyllacosaminide (Gal-β-1-3-GlcNAc) moiety as terminal end group.

The step i) performing the method as mentioned above to obtain CMP-Neu5Ac, refers to all of above described method for producing cytidine 5'-monophospho-N-acetyl-neuraminic acid (CMP-Neu5Ac, 1)

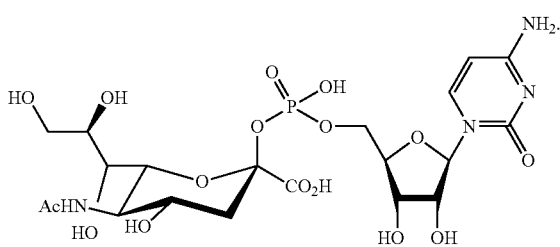

Therefore, the present invention also refers to a method for producing a Neu5Acylated i.e. sialylated biomolecule comprising
i) performing the method as mentioned above to obtain CMP-Neu5Ac comprising:
A) providing a solution comprising N-acetyl-D-glucosamine, pyruvate, polyphosphate, cytidine, and adenosine 5'-triphosphate (ATP), and
a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);
B) mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine monophosphate (CMP); and
ii) reacting the CMP-Neu5Ac obtained after step i) with a biomolecule, wherein the biomolecule is a saccharide, a glycopeptide, a glycoprotein, a glycolipid, a glycan, a peptide, a protein, an antibody, an antibody drug conjugate, a carbohydrate conjugate vaccine, virus, virus like particles, virus vaccine, or a flavonoid by forming an O-glycosidic bond with an hydroxyl group of the biomolecule with removal of CMP group in the presence of a sialyltransferase.

Preferably, the set of enzymes is co-immobilized on a solid support.

Therefore, the present invention also refers to a method for producing a Neu5Acylated i.e. sialylated biomolecule comprising
ii) performing the method as mentioned above to obtain CMP-Neu5Ac comprising:
A) providing a solution comprising N-acetyl-D-glucosamine, pyruvate, polyphosphate, cytidine, and adenosine 5'-triphosphate (ATP), and
a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);
B) mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine monophosphate (CMP); and
iii) reacting the CMP-Neu5Ac obtained after step i) with a biomolecule, wherein the biomolecule is a saccharide, a glycopeptide, a glycoprotein, a glycolipid, a glycan, a peptide, a protein, an antibody, an antibody drug conjugate, a carbohydrate conjugate vaccine, virus, virus like particles, virus vaccine, or a flavonoid by forming an O-glycosidic bond with an hydroxyl group of the biomolecule with removal of CMP group in the presence of a sialyltransferase. Preferably, the set of enzymes is co-immobilized on a solid support.

Preferably, the present invention also refers to a method for producing a Neu5Acylated i.e. sialylated biomolecule comprising
i) performing the method as mentioned above to obtain CMP-Neu5Ac comprising:
A) providing a solution comprising N-acetyl-D-glucosamine, pyruvate, polyphosphate, cytidine, and adenosine 5'-triphosphate (ATP), and a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);

B) mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine monophosphate (CMP);

C) isolating cytidine 5'-monophospho-N-acetyl-neuraminic acid (CMP-Neu5Ac) produced after the step B) by ion exchange chromatography;
wherein the uridine kinase (UDK) transfers in situ the cytidine to a cytidine monophosphate (CMP); and ii) reacting the CMP-Neu5Ac obtained after step i) with a biomolecule, wherein the biomolecule is a saccharide, a glycopeptide, a glycoprotein, a glycolipid, a glycan, a peptide, a protein, an antibody, an antibody drug conjugate, a carbohydrate conjugate vaccine, virus, virus like particles, virus vaccine, or a flavonoid by forming an O-glycosidic bond with an hydroxyl group of the biomolecule with removal of CMP group in the presence of a sialyltransferase. Preferably, the set of enzymes is co-immobilized on a solid support.

Preferably, the present invention also refers to a method for producing a Neu5Acylated i.e. sialylated biomolecule comprising i) performing the method as mentioned above to obtain CMP-Neu5Ac comprising:

A) providing a solution comprising N-acetyl-D-glucosamine, pyruvate, polyphosphate, cytidine, and adenosine 5'-triphosphate (ATP), and a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);

B) mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine monophosphate (CMP);

C) isolating cytidine 5'-monophospho-N-acetyl-neuraminic acid (CMP-Neu5Ac) produced after the step B) by ion exchange chromatography;

C') drying the isolated cytidine 5'-monophospho-N-acetyl-neuraminic acid (CMP-Neu5Ac) obtained after the step C) by lyophilization,
wherein the uridine kinase (UDK) transfers in situ the cytidine to a cytidine monophosphate (CMP); and ii) reacting the CMP-Neu5Ac obtained after step i) with a biomolecule, wherein the biomolecule is a saccharide, a glycopeptide, a glycoprotein, a glycolipid, a glycan, a peptide, a protein, an antibody, an antibody drug conjugate, a carbohydrate conjugate vaccine, or a flavonoid by forming an O-glycosidic bond with an hydroxyl group of the biomolecule with removal of CMP group in the presence of a sialyltransferase. Preferably, the set of enzymes is co-immobilized on a solid support.

Preferably, the saccharide is a human milk oligosaccharide including lactose, N-acetyl-lactosamine, lacto-N-biose, 2'-fucosyllactose, 3-fucosyllactose (3-FL), lacto-N-tetraose (LNT), lacto-N-neotetraose (LNnT), difucosyllactose (DiFL), lacto-N-triose II (LNT-II), lacto-N-fucopentaose I (LNFP I), lacto-N-fucopentaose III (LNFP III), lacto-N-fucopentaose V (LNFPV).

Therefore, the present invention refers to a method for producing a Neu5Acylated biomolecule comprising i) performing the method as mentioned above to obtain a CMP-Neu5Ac, ii) reacting the CMP-Neu5Ac obtained after step i) with a biomolecule, wherein the biomolecule is a human milk oligosaccharide including lactose, N-acetyl-lactosamine, lacto-N-biose, 2'-fucosyllactose, 3-fucosyllactose (3-FL), lacto-N-tetraose (LNT), lacto-N-neotetraose (LNnT), difucosyllactose (DiFL), lacto-N-triose II (LNT-II), lacto-N-fucopentaose I (LNFP I), lacto-N-fucopentaose III (LNFP III), lacto-N-fucopentaose V (LNFPV).

Preferably, the present invention also refers to a method for producing a Neu5Acylated i.e. sialylated biomolecule comprising i) performing the method as mentioned above to obtain CMP-Neu5Ac comprising:

A) providing a solution comprising N-acetyl-D-glucosamine, pyruvate, polyphosphate, cytidine, and adenosine 5'-triphosphate (ATP), and a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);

B) mixing said solution and said set of enzymes and reacting a resulting solution to produce cytidine 5'-monophospho-N-acetyl-neuraminic acid (CMP-Neu5Ac),
wherein the uridine kinase (UDK) transfers in situ the cytidine to a cytidine monophosphate (CMP);

C) isolating cytidine 5'-monophospho-N-acetyl-neuraminic acid (CMP-Neu5Ac) produced after the step B) by ion exchange chromatography;
wherein the uridine kinase (UDK) transfers in situ the cytidine to a cytidine monophosphate (CMP); and ii) reacting the CMP-Neu5Ac obtained after step i) with a biomolecule, wherein the biomolecule is a human milk oligosaccharide including lactose, N-acetyl-lactosamine, lacto-N-biose, 2'-fucosyllactose, 3-fucosyllactose (3-FL), lacto-N-tetraose (LNT), lacto-N-neotetraose (LNnT), difucosyllactose (DiFL), lacto-N-triose II (LNT-II), lacto-N-fucopentaose I (LNFP I), lacto-N-fucopentaose III (LNFP III), lacto-N-fucopentaose V (LNFPV).

Preferably, the present invention also refers to a method for producing a Neu5Acylated i.e. sialylated biomolecule comprising i) performing the method as mentioned above to obtain CMP-Neu5Ac comprising:

A) providing a solution comprising N-acetyl-D-glucosamine, pyruvate, polyphosphate, cytidine, and adenosine 5'-triphosphate (ATP), and a set of enzymes comprising an N-acylglucosamine 2-epimerase (AGE), an N-acetylneuraminate lyase (NAL), an N-acylneuraminate cytidylyltransferase (CSS), a uridine kinase (UDK), a uridine monophosphate kinase and a polyphosphate kinase 3 (PPK3);

B) mixing said solution and said set of enzymes and reacting a resulting solution to produce cytidine 5'-monophospho-N-acetyl-neuraminic acid (CMP-Neu5Ac), C) isolating cytidine 5'-monophospho-N-acetyl-neuraminic acid (CMP-Neu5Ac) produced after the step B) by ion exchange chromatography;

C') drying the isolated cytidine 5'-monophospho-N-acetyl-neuraminic acid (CMP-Neu5Ac) obtained after the step C) by lyophilization, wherein the uridine kinase (UDK) transfers in situ the cytidine to a cytidine monophosphate (CMP); and ii) reacting the CMP-Neu5Ac obtained after step i) with a biomolecule, wherein the biomolecule is a human milk oligosaccharide including lactose, N-acetyl-lactosamine, lacto-N-biose, 2'-fucosyllactose, 3-fucosyllactose (3-FL), lacto-N-tetraose (LNT), lacto-N-neotetraose (LNnT), difucosyllactose (DiFL), lacto-N-triose II (LNT-II), lacto-N-fucopentaose I (LNFP I), lacto-N-fucopentaose III (LNFP III), lacto-N-fucopentaose V (LNFPV).

Preferably, the carbohydrate conjugate vaccine comprises a saccharide selected from a *N. meningitidis* serotype B saccharide, a *Pasteurella haemolytica* A2 saccharide, a *Streptococcus agalactiae* saccharide, and a *Haemophilus ducreyi* saccharide.

Preferably, the glycolipid is a glycosphingolipid comprising a galactosylceramide moiety. In particular, the Neu5Acteylated glycolipid is a ganglioside with one or more N-acetylneuraminic acid, Neu5Ac) linked on the sugar chain. Types of ganglioside includes LM1, GM1, GM1b, and GM2 which comprise one N-acetyl-neuraminic acid; GD1a, GalNAc-GD1a, GD1b, GD2, and GD3 which comprise two N-acetylneuraminic acids; GT1a, and GT3 which comprise three N-acetyl-neuraminic acids; and GQ1 b which comprises four N-acetylneuraminic acids.

Preferably, the therapeutic protein is a protein of the immunoglobulin superfamily. Preferably, the protein of the immunoglobulin superfamily and is an antibody. Preferably, the antibody is a monoclonal antibody including bispecific monoclonal antibodies and antibody-based drugs. Preferably, the antibody is not fully Neu5Acylated. Preferably the therapeutic protein is selected from the group consisting of:

3F8, 8H9, Arcitumomab, Ascrinvacumab, Aselizumab, Atezolizumab, Atidortoxumab, Atinuma, Atorolimumab, Avelumab, Azintuxizumab vedotin, Bapineuzumab, Basiliximab, Bavituximab, BCD-100, Bectumomab, Begelomab, Belantamab mafodotin, Belimumab, Bemarituzuma, Benralizumab, Berlimatoxumab, Bermekimab, Bersanlimab, Bertilimumab, Besilesomab, Bevacizumab, Bezlotoxumab, Biciromab, Bimagrumab, Bimekizumab, Birtamimab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Camidanlumab tesirine, Camrelizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cemiplimab, Cergutuzumab amunaleukin, Certolizumab pegol, Cetrelimab, Cetuximab, Cibisatamab, Cirmtuzumab, Citatuzumab bogatox, Cixutumumab, Clazakizumab, Clenoliximab, Clivatuzumab tetraxetan, Codrituzumab, Cofetuzumab pelidotin, Coltuximab ravtansine, Conatumumab, Concizumab, Cosfroviximab, CR6261, Crenezumab, Crizanlizumab, Crotedumab, Cusatuzumab, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dezamizumab, Dinutuximab, Diridavumab, Domagrozumab, Dorlimomab aritox, Dostarlima, Drozitumab, DS-8201, Duligotuzumab, Dupilumab, Durvalumab, Dusigitumab, Duvortuxizumab, Ecromeximab, Eculizumab, Edobacomab, Edrecolomab, Efalizumab, Efungumab, Eldelumab, Elezanumab, Elgemtumab, Elotuzumab, Elsilimomab, Emactuzumab, Emapalumab, Emibetuzumab, Emicizumab, Enapotamab vedotin, Enavatuzumab, Enfortumab vedotin, Enlimomab pegol, Enoblituzumab, Enokizumab, Enoticumab, Ensituximab, Epitumomab cituxetan, Epratuzumab, Eptinezumab, Erenumab, Erlizumab, Ertumaxomab, Etaracizumab, Etigilimab, Etrolizumab, Evinacumab, Evolocumab, Exbivirumab, Fanolesomab, Faralimomab, Faricimab, Farletuzumab, Fasinumab, FBTA05, Felvizumab, Fezakinumab, Fibatuzumab, Ficlatuzumab, Figitumumab, Firivumab, Flanvotumab, Fletikumab, Flotetuzumab, Fontolizumab, Foralumab, Foravirumab, Fremanezumab, Fresolimumab, Frovocimab, Frunevetmab, Fulranumab, Futuximab, Galcanezumab, Galiximab, Gancotama, Ganitumab, Gantenerumab, Gatipotuzumab, Gavilimomab, Gedivumab, Gemtuzumab ozogamicin, Gevokizumab, Gilvetmab, Gimsilumab, Girentuximab, Glembatumumab vedotin, Golimumab, Gomiliximab, Gosuranemab, Guselkumab, Ianalumab, Ibalizumab, IBI308, Ibritumomab tiuxetan, Icrucumab, Idarucizumab, Ifabotuzumab, Igovomab, Iladatuzumab vedotin, IMAB362, Imalumab, Imaprelimab, Imciromab, Imgatuzumab, Inclacumab, Indatuximab ravtansine, Indusatumab vedotin, Inebilizumab, Infliximab, Inolimomab, Inotuzumab ozogamicin, Intetumumab, Iomab-B, Ipilimumab, Iratumumab, Isatuximab, Iscalimab, Istiratumab, Itolizumab, Ixekizumab, Keliximab, Labetuzumab, Lacnotuzumab, Ladiratuzumab vedotin, Lampalizumab, Lanadelumab, Landogrozumab, Laprituximab emtansine, Larcaviximab, Lebrikizumab, Lemalesomab, Lendalizumab, Lenvervimab, Lenzilumab, Lerdelimumab, Leronlimab, Lesofavumab, Letolizumab, Lexatumumab, Libivirumab, Lifastuzumab vedotin, Ligelizumab, Lilotomab satetraxetan, Lintuzumab, Lirilumab, Lodelcizumab, Lokivetmab, Loncastuximab tesirine, Lorvotuzumab mertansine, Losatuxizumab vedotin, Lucatumumab, Lulizumab pegol, Lumiliximab, Lumretuzumab, Lupartumab amadotin, Lutikizumab, Mapatumumab, Margetuximab, Marstacima, Maslimomab, Matuzumab, Mavrilimumab, Mepolizumab, Metelimumab, Milatuzumab, Minretumomab, Mirikizumab, Mirvetuximab soravtansine, Mitumomab, Modotuximab, Mogamulizumab, Monalizumab, Morolimumab, Mosunetuzumab, Motavizumab, Moxetumomab pasudotox, Muromonab-CD3, Nacolomab tafenatox, Namilumab, Naptumomab estafenatox, Naratuximab emtansine, Narnatumab, Natalizumab, Navicixizumab, Navivumab, Naxitamab, Nebacumab, Necitumumab, Nemolizumab, NEOD001, Nerelimomab, Nesvacumab, Netakimab, Nimotuzumab, Nirsevimab, Nivolumab, Nofetumomab merpentan, Obiltoxaximab, Obinutuzumab, Ocaratuzumab, Ocrelizumab, Odulimomab, Ofatumumab, Olaratumab, Oleclumab, Olendalizumab, Olokizumab, Omalizumab, Omburtamab, OMS721, Onartuzumab, Ontuxizumab, Onvatilimab, Opicinumab, Oportuzumab monatox, Oregovomab, Orticumab, Otelixizumab, Otilimab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, PDR001, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Porgaviximab, Prasinezumab, Prezalizumab, Priliximab, Pritoxaximab, Pritumumab, PRO 140, Quilizumab, Racotumomab, Radretumab, Rafivirumab, Ralpancizumab, Ramucirumab, Ranevetmab, Ranibizumab, Ravagalimab, Ravulizumab, Raxibacumab, Refanezumab, Regavirumab, Relatlimab, Remtolumab, Reslizumab, Rilotumumab, Rinucumab, Risankizumab, Rituximab, Rivabazumab pegol, Rmab, Robatumumab, Roledumab, Romilkimab, Romosozumab, Rontalizumab, Rosmantuzumab, Rovalpituzumab tesirine, Rovelizumab, Rozanolixizumab, Ruplizumab, SA237, Sacituzumab govitecan, Samalizumab, Samrotamab vedotin, Sarilumab, Satralizumab, Satumomab pendetide, Secukinumab, Selicrelumab, Seribantumab, Setoxaximab, Setrusumab, Sevirumab, SGN-CD19A, SHP647, Sibrotuzumab, Sifalimumab, Siltuximab, Simtuzumab, Siplizumab, Sirtratumab vedotin, Sirukumab, Sofituzumab vedotin, Solanezumab, Solitomab, Sonepcizumab, Sontuzumab, Spartalizumab, Stamulumab, Sulesomab, Suptavumab, Sutimlimab, Suvizumab, Suvratoxumab, Tabalumab, Tacatuzumab tetraxetan, Tadocizumab, Talacotuzumab, Talizumab, Tamtuvetmab, Tanezumab, Taplitumomab paptox, Tarextumab, Tavolimab, Tefibazumab, Telimomab aritox, Telisotuzumab vedotin, Tenatumomab, Teneliximab, Teplizumab, Tepoditamab, Teprotumumab, Tesidolumab, Tetulomab, Tezepelumab, TGN1412, Tibulizumab, Tigatuzumab, Tildrakizumab, Timigutuzumab, Timolumab, Tiragotumab, Tislelizumab, Tisotumab vedotin, TNX-650, Tocilizumab, Tomuzotuximab, Toralizumab, Tosatoxumab, Tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vanalimab, Vandortuzumab vedotin, Vantictumab, Vanucizumab, Vapaliximab, Varisacumab, Varlilumab, Vatelizumab, Vedolizumab, Veltuzumab, Vepalimomab, Vesencumab, Visilizumab, Vobarilizumab, Volociximab, Vonlerolizumab, Vopratelimab, Vorsetuzumab mafodotin, Votumumab, Vunakizumab, Xentuzumab, XMAB-5574, Zalutumumab, Zanolimumab, Zatuximab, Zenocutuzumab, Ziralimumab, Zolbetuximab (=IMAB36, Claudiximab), and Zolimomab aritox.

Preferably, the flavonoids include flavones, falvonols, valvanones, falavanonols, flavans flavanols, flavandiols, and isoflavones, isoflavanes, isoflavandiols, isoflavenes and coumestans and pterocarpans, more preferred said flavonoids are O-glycosylated.

Neu5Ac can potentially be transferred to the viruses as well as virus like particles and vaccines related to the following viruses.

| Virus | Genus |
|---|---|
| Adeno-associated virus | *Dependovirus, Parvoviridae* |
| Aichi virus | *Kobuvirus, Picornaviridae* |
| Australian bat lyssavirus | *Lyssavirus, Rhabdoviridae* |
| BK polyomavirus | *Polyomavirus, Polyomaviridae* |
| Banna virus | *Seadornavirus, Reoviridae* |
| Barmah forest virus | *Alphavirus, Togaviridae* |
| Bunyamwera virus | *Orthobunyavirus, Bunyaviridae* |
| Bunyavirus La Crosse | *Orthobunyavirus, Bunyaviridae* |
| Bunyavirus snowshoe hare | *Orthobunyavirus, Bunyaviridae* |
| Cercopithecine herpesvirus | *Lymphocryptovirus, Herpesviridae* |
| Chandipura virus | *Vesiculovirus, Rhabdoviridae* |
| Chikungunya virus | *Alphavirus, Togaviridae* |
| Cosavirus A | *Cosavirus, Picornaviridae* |
| Cowpox virus | *Orthopoxvirus, Poxviridae* |
| Coxsackievirus | *Enterovirus, Picornaviridae* |
| Crimean-Congo hemorrhagic fever virus | *Nairovirus, Bunyaviridae* |
| Dengue virus | *Flavivirus, Flaviviridae* |
| Dhori virus | *Thogotovirus, Orthomyxoviridae* |
| Dugbe virus | *Nairovirus, Bunyaviridae* |
| Duvenhage virus | *Lyssavirus, Rhabdoviridae* |
| Eastern equine encephalitis virus | *Alphavirus, Togaviridae* |
| Ebolavirus | *Ebolavirus, Filoviridae* |
| Echovirus | *Enterovirus, Picornaviridae* |
| Encephalomyocarditis virus | *Cardiovirus, Picornaviridae* |
| Epstein-Barr virus | *Lymphocryptovirus, Herpesviridae* |
| European bat lyssavirus | *Lyssavirus, Rhabdovirus* |
| GB virus C/Hepatitis G virus | *Pegivirus, Flaviviridae* |
| Hantaan virus | *Hantavirus, Bunyaviridae* |
| Hendra virus | *Henipavirus, paramyxoviridae* |
| Hepatitis A virus | *Hepatovirus, picornaviridae* |
| Hepatitis B virus | *Orthohepadnavirus, Hepadnaviridae* |
| Hepatitis C virus | *Hepacivirus, Flaviviridae* |
| Hepatitis E virus | *Hepevirus, Unassigned* |
| Hepatitis delta virus | *Deltavirus, Unassigned* |
| Horsepox virus | *Orthopoxvirus, Poxviridae* |
| Human adenovirus | *Mastadenovirus, Adenoviridae* |
| Human astrovirus | *Mamastrovirus, Astroviridae* |
| Human coronavirus | *Alphacoronavirus, Coronaviridae* |
| Human cytomegalovirus | *Cytomegalovirus, Herpesviridae* |

-continued

| Virus | Genus |
|---|---|
| Human enterovirus 68, 70 | *Enterovirus, Picornaviridae* |
| Human herpesvirus 1 | *Simplexvirus, Herpesviridae* |
| Human herpesvirus 2 | *Simplexvirus, Herpesviridae* |
| Human herpesvirus 6 | *Roseolovirus, Herpesviridae* |
| Human herpesvirus 7 | *Roseolovirus, Herpesviridae* |
| Human herpesvirus 8 | *Rhadinovirus, Herpesviridae* |
| Human immunodeficiency virus | *Lentivirus, Retroviridae* |
| Human papillomavirus 1 | *Mupapillomavirus, Papillomaviridae* |
| Human papillomavirus 2 | *Alphapapillomavirus, Papillomaviridae* |
| Human papillomavirus 16, 18 | *Alphapapillomavirus, Papillomaviridae* |
| Human parainfluenza | *Respirovirus, Paramyxoviridae* |
| Human parvovirus B19 | *Erythrovirus, Parvoviridae* |
| Human respiratory syncytial virus | *Orthopneumovirus, Pneumoviridae* |
| Human rhinovirus | *Enterovirus, Picornaviridae* |
| Human SARS coronavirus | *Betacoronavirus, Coronaviridae* |
| Human spumaretrovirus | *Spumavirus, Retroviridae* |
| Human T-lymphotropic virus | *Deltaretrovirus, Retroviridae* |
| Human torovirus | *Torovirus, Coronaviridae* |
| Influenza A virus | *Influenzavirus A, Orthomyxoviridae* |
| Influenza B virus | *Influenzavirus B, Orthomyxoviridae* |
| Influenza C virus | *Influenzavirus C, Orthomyxoviridae* |
| Isfahan virus | *Vesiculovirus, Rhabdoviridae* |
| JC polyomavirus | *Polyomavirus, Polyomaviridae* |
| Japanese encephalitis virus | *Flavivirus, Flaviviridae* |
| Junin arenavirus | *Arenavirus, Arenaviridae* |
| Kl Polyomavirus | *Polyomavirus, Polyomaviridae* |
| Kunjin virus | *Flavivirus, Flaviviridae* |
| Lagos bat virus | *Lyssavirus, Rhabdoviridae* |
| Lake Victoria marburgvirus | *Marburgvirus, Filoviridae* |
| Langat virus | *Flavivirus, Flaviviridae* |
| Lassa virus | *Arenavirus, Arenaviridae* |
| Lordsdale virus | *Norovirus, Caliciviridae* |
| Louping ill virus | *Flavivirus, Flaviviridae* |
| Lymphocytic choriomeningitis virus | *Arenavirus, Arenaviridae* |
| Machupo virus | *Arenavirus, Arenaviridae* |
| Mayaro virus | *Alphavirus, Togaviridae* |
| MERS coronavirus | *Betacoronavirus, Coronaviridae* |
| Measles virus | *Morbilivirus, Paramyxoviridae* |
| Mengo encephalomyocarditis virus | *Cardiovirus, Picornaviridae* |
| Merkel cell polyomavirus | *Polyomavirus, Polyomaviridae* |
| Mokola virus | *Lyssavirus, Rhabdoviridae* |
| Molluscum contagiosum virus | *Molluscipoxvirus, Poxviridae* |
| Monkeypox virus | *Orthopoxvirus, Poxviridae* |
| Mumps virus | *Rubulavirus, Paramyxoviridae* |
| Murray valley encephalitis virus | *Flavivirus, Flaviviridae* |
| New York virus | *Hantavirus, Bunyavirus* |
| Nipah virus | *Henipavirus, Paramyxoviridae* |
| Norwalk virus | *Norovirus, Caliciviridae* |
| O'nyong-nyong virus | *Alphavirus, Togaviridae* |
| Orf virus | *Parapoxvirus, Poxviridae* |
| Oropouche virus | *Orthobunyavirus, Bunyaviridae* |
| Pichinde virus | *Arenavirus, Arenaviridae* |
| Poliovirus | *Enterovirus, Picornaviridae* |
| Punta toro phlebovirus | *Phlebovirus, Bunyaviridae* |
| Puumala virus | *Hantavirus, Bunyavirus* |
| Rabies virus | *Lyssavirus, Rhabdoviridae* |
| Rift valley fever virus | *Phlebovirus, Bunyaviridae* |
| Rosavirus A | *Rosavirus, Picornaviridae* |
| Ross river virus | *Alphavirus, Togaviridae* |
| Rotavirus A | *Rotavirus, Reoviridae* |
| Rotavirus B | *Rotavirus, Reoviridae* |
| Rotavirus C | *Rotavirus, Reoviridae* |
| Rubella virus | *Rubivirus, Togaviridae* |
| Sagiyama virus | *Alphavirus, Togaviridae* |
| Salivirus A | *Salivirus, Picornaviridae* |
| Sandfly fever sicilian virus | *Phlebovirus, Bunyaviridae* |
| Sapporo virus | *Sapovirus, Caliciviridae* |
| Semliki forest virus | *Alphavirus, Togaviridae* |
| Seoul virus | *Hantavirus, Bunyavirus* |
| Simian foamy virus | *Spumavirus, Retroviridae* |
| Simian virus 5 | *Rubulavirus, Paramyxoviridae* |
| Sindbis virus | *Alphavirus, Togaviridae* |
| Southampton virus | *Norovirus, Caliciviridae* |
| St. louis encephalitis virus | *Flavivirus, Flaviviridae* |
| Tick-borne powassan virus | *Flavivirus, Flaviviridae* |
| Torque teno virus | *Alphatorquevirus, Anelloviridae* |
| Toscana virus | *Phlebovirus, Bunyaviridae* |

| Virus | Genus |
|---|---|
| Uukuniemi virus | Phlebovirus, Bunyaviridae |
| Vaccinia virus | Orthopoxvirus, Poxviridae |
| Varicella-zoster virus | Varicellovirus, Herpesviridae |
| Variola virus | Orthopoxvirus, Poxviridae |
| Venezuelan equine encephalitis virus | Alphavirus, Togaviridae |
| Vesicular stomatitis virus | Vesiculovirus, Rhabdoviridae |
| Western equine encephalitis virus | Alphavirus, Togaviridae |
| WU polyomavirus | Polyomavirus, Polyomaviridae |
| West Nile virus | Flavivirus, Flaviviridae |
| Yaba monkey tumor virus | Orthopoxvirus, Poxviridae |
| Yaba-like disease virus | Orthopoxvirus, Poxviridae |
| Yellow fever virus | Flavivirus, Flaviviridae |
| Zika virus | Flavivirus, Flaviviridae |

DESCRIPTION OF THE FIGURES

FIG. 1: (A) shows the multi-enzyme cascade through which CMP-Neu5Ac is enzymatically synthesized from low-cost substrates N-acetyl-D-glucosamine (GlcNAc), pyruvate, polyphosphate and cytidine. The reaction cascade comprises (a) the formation of N-acetyl-D-mannosamine (ManNAc) from N-acetyl-D-glucosamine (GlcNAc), (b) the formation of N-acetyl-D-neuraminic acid (Neu5Ac) from ManNAc and pyruvate, (c) the formation of cytidine 5'-monophosphate (CMP) from cytidine and adenosine 5'-triphosphate (ATP), (d) the formation of cytidine 5'-diphosphate (CDP) from CMP and ATP, (e) the formation of cytidine 5'-triphosphate (CTP) from CDP and polyphosphate (PolyP$_n$), and (f) the reaction of Neu5Ac with CTP to CMP-Neu5Ac. Optionally, the cascade can be extended by adding a 1D-PPK2 to assist the conversion of ADP to ATP. Also, the cascade can be extended by adding a 2D-PPK2 in order to activate phosphorylation of AMP to ADP. Moreover, the cascade can be extended by adding a 1D-PPK2 and a 2D-PPK2 in order to inhibit frequent hydrolysis of adenosine phosphates.
  (B) shows the multi-enzyme cascade through which CMP-Neu5Ac is enzymatically synthesized from the substrates D-glucosamine (GlcN) and acetate. In this cascade, a step (a') is further added. (a') the formation of N-acetyl-D-glucosamine (GlcNAc) from D-glucosamine (GlcN) and acetate being catalyzed by N-acetylglucosamine deacetylase.

FIG. 4 shows the sequence listings of enzymes.
  (A) AGE family epimerase/isomerase from Trichormus variabilis;
  (B) N-acetylneuraminate lyase (NANA) from Pasteurella multocida (strain Pm70);
  (C) N-acylneuraminate cytidylyltransferase (CSS) from Neisseria meningitidis serogroup B (strain MC58);
  (D) Uridine kinase (UDK) from Escherichia coli (strain K12);
  (E) UMP-CMP kinase 3 (URA6) from Arabidopsis thaliana;
  (F) Polyphosphate:NDP phosphotransferase 3 (PPK3) from Ruegeria pomeroyi (strain ATCC 700808/DSM 15171/DSS-3);
  (G) Inorganic pyrophosphatase (PPA) from Pasteurella multocida (strain Pm70);
  (H) 2-domain polyphosphate kinase 2 (2D-PPK2)=Polyphosphate: AMP phosphotransferase from Pseudomonas aeruginosa (strain ATCC 15692/DSM 22644/CIP 104116/JCM 14847/LMG 12228/IC/PRS 101/PA01).
  (I) 1-domain polyphosphate kinase 2 (1D-PPK2)=Polyphosphate:ADP phosphotransferase from Pseudomonas aeruginosa (strain ATCC 15692/DSM 22644/CIP 104116/JCM 14847/LMG 12228/IC/PRS 101/PA01); Uniprot-ID: Q91154

FIG. 28. Synthesis of 6'-SL: A. Chromatogram and B. MS spectra of the reaction at the reaction end point.

Figure 2:
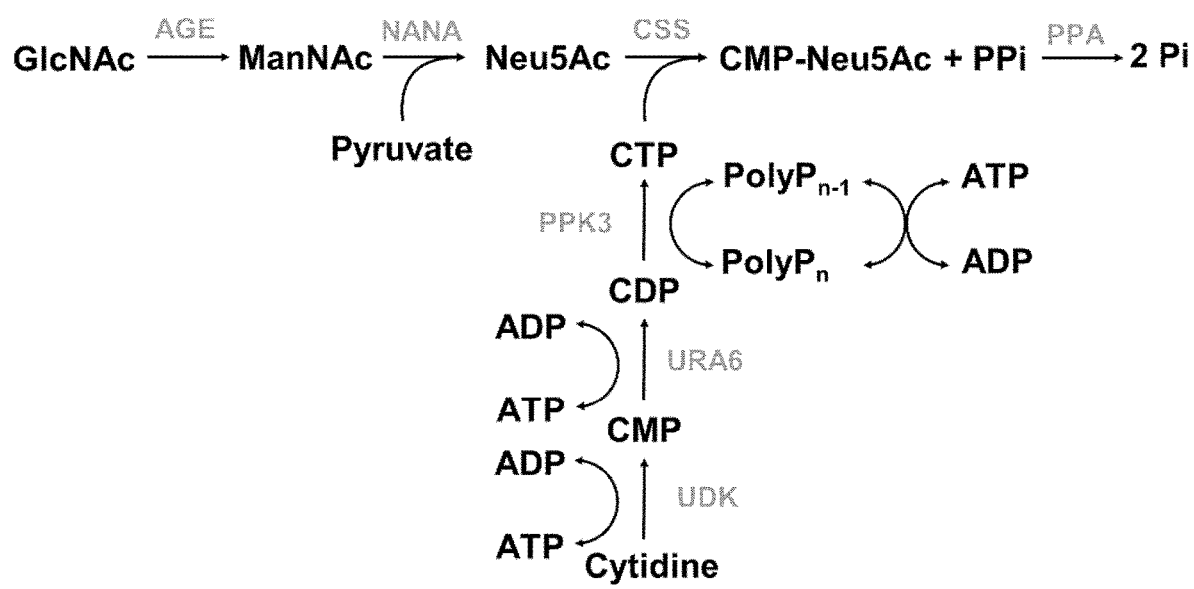
FIG. 2: shows the multi-enzyme cascade through which CMP-Neu5Ac is enzymatically synthesized from low-cost substrates N-acetyl-D-glucosamine (GlcNAc), pyruvate, polyphosphate and cytidine. Optionally, the cascade can be extended by adding an inorganic diphosphatase (PPA) to hydrolyze pyrophosphate PPi which inhibits the activity of N-acylneuraminate cytidylyltransferase (CSS).
Figure 3:
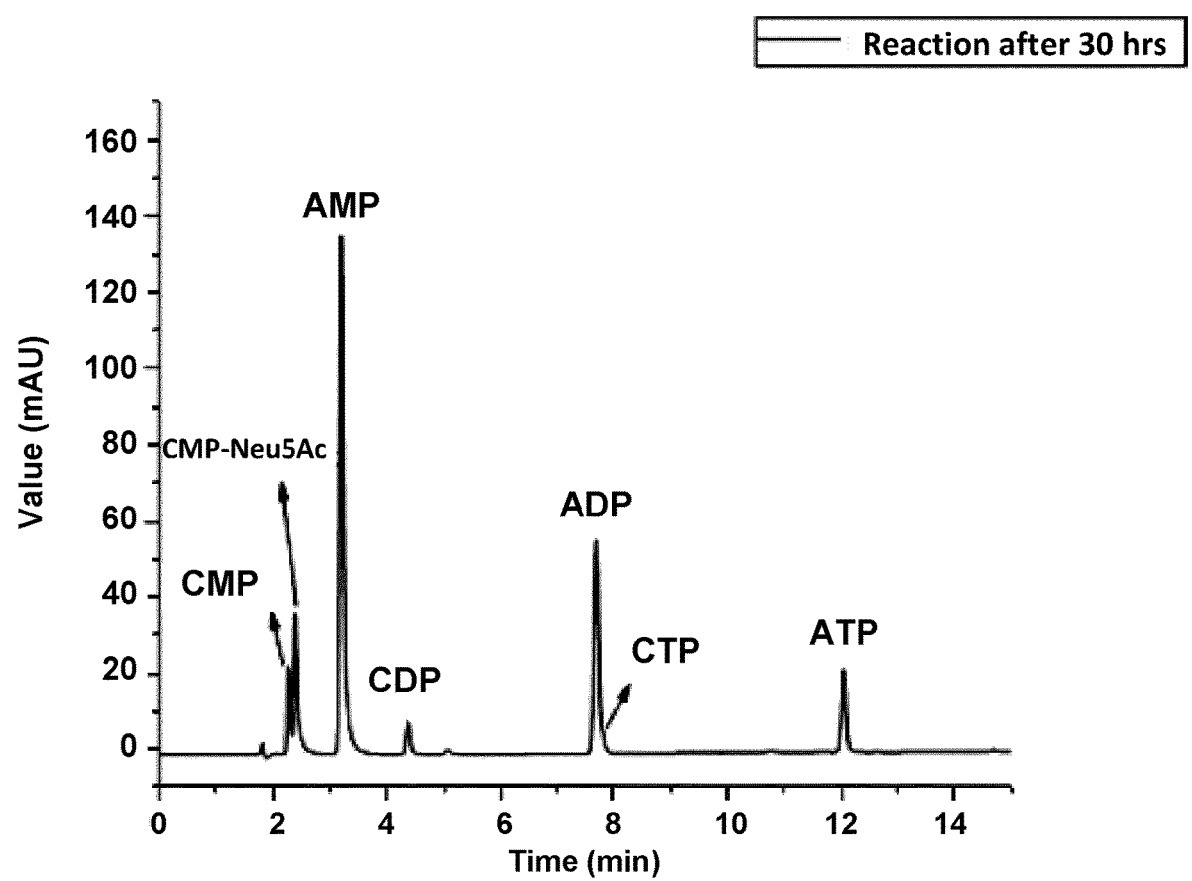
FIG. 3: shows the quantification of CMP-Neu5Ac by means of HPAEC-UV chromatograms.
  A) HPAEC-UV chromatograms of the quantification of CMP-Neu5Ac. The concentration curve of CMP-Neu5Ac shows saturation after 30 hours.
  B) HPAEC-UV chromatograms of the quantification of CMP-Neu5Ac (and other reactants) after 4 minutes reaction time.
  C) HPAEC-UV chromatograms of the quantification of CMP-Neu5Ac (and other reactants) after 30 hours reaction time.
Figure 5:
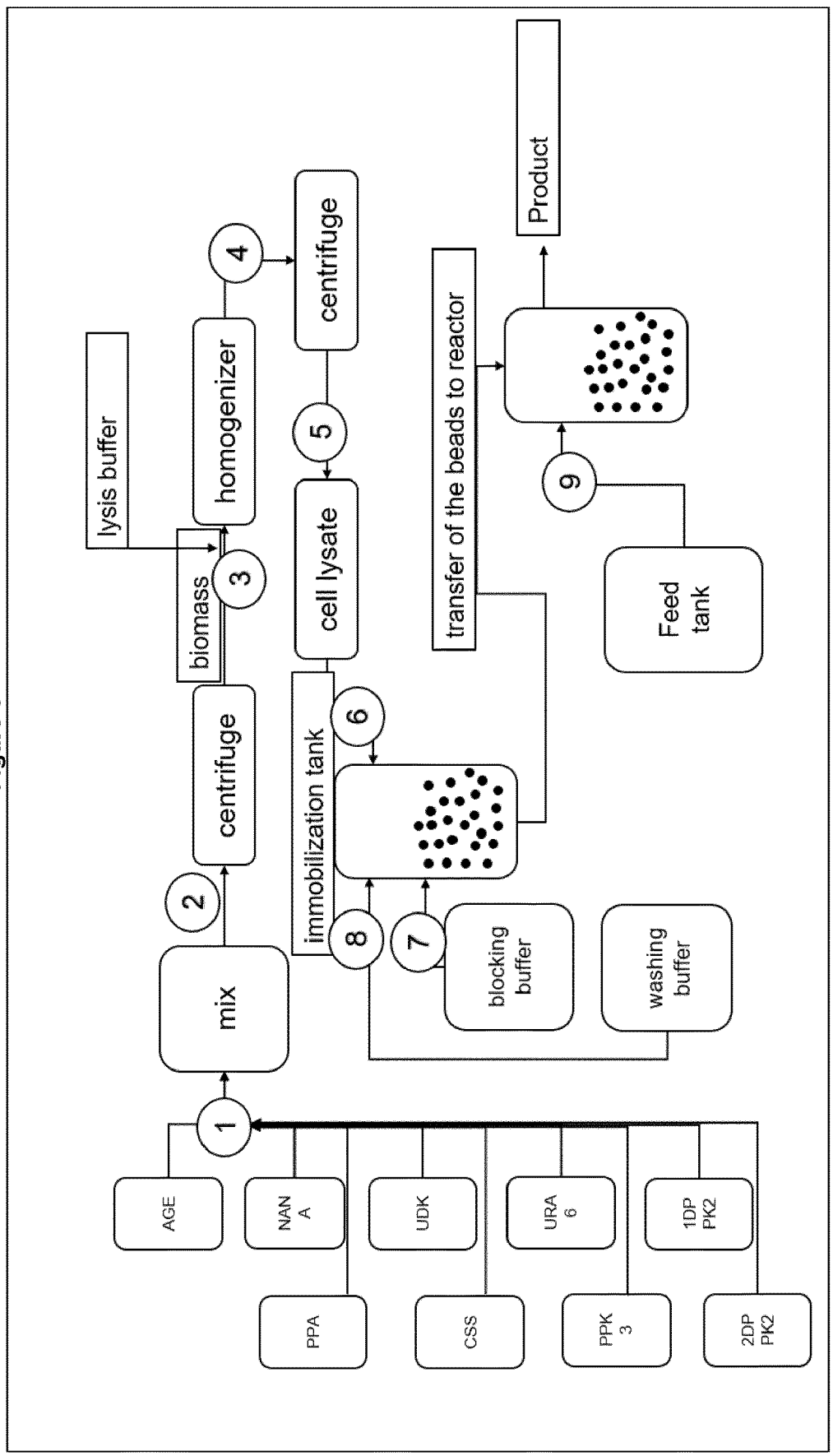
FIG. 5 shows a workflow scheme for the complete CMP-Neu5Ac cascade starting from mixing the biomasses containing the overexpressed enzymes to carrying out the synthesis reaction of CMP-Neu5Ac on a solid support. The workflow is also suitable for screening various solid supports for enzyme immobilization.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

| Abbreviations and Acronyms | |
|---|---|
| AGE | N-acetyl-D-glucosamine epimerase/isomerase |
| ADP | adenosine 5'-diphosphate |
| AMP | adenosine 5'-monophosphate |
| ATP | adenosine 5'-triphosphate |
| dH$_2$O | deionized water |
| CMP | cytidine 5'-monophosphate |
| CDP | cytidine 5'-diphosphate |
| CTP | cytidine 5'-triphosphate |
| CSS | N-acylneuraminate cytidylyltransferase |
| NmCSS | N-acylneuraminate cytidylyltransferase of *Neisseria meningitidis* serogroup B (strain MC58) |
| NAL | N-acetylneuraminate lyase, or N-acetylneuraminate pyruvate lyase |
| GlcN | D-glucosamine |
| GlcNAc | N-acetyl-D-glucosamine |
| ManNAc | N-acetyl-D-mannosamine |
| Neu5Ac | N-acetyl-D-neuraminic acid, or 5-(acetylamino)-3,5-dideoxy-D-glycero-α-D-galacto-non-2-ulopyranosonic acid |
| CMP-Neu5Ac | cytidine 5'-monophosphate N-acetyl-D-neuraminic acid |
| PolyP | polyphosphate |
| PPi | pyrophosphate |
| Pi | phosphate |
| PPK2 | polyphosphate kinase 2 |
| PPK3 | polyphosphate kinase 3 |

-continued

| Abbreviations and Acronyms | |
|---|---|
| 1D-PPK2 | 1-domain polyphosphate kinase 2, polyphosphate:ADP phosphotransferase |
| 2D-PPK2 | 2-domain polyphosphate kinase 2, polyphosphate:AMP phosphotransferase |
| URA6 | uridine monophosphate kinase |
| PPA | inorganic pyrophosphatase |
| PmPpA | *Pasteurella multocida* inorganic pyrophosphatase |

Chemicals & Reagents

Unless otherwise stated, all chemicals and reagents were acquired from Sigma-Aldrich and CarboSynth, and were of the highest purity available. Solid supports were obtained from Resindion, ChiralVision, Rohm GmbH & Co. KG and micromod GmbH.

Example 1: Preparation of Enzymes

Each plasmid was individually transformed into *E. coli* BL21 and followed by cultivation on LB agar plates with selection markers. For each enzyme expression the following protocol was followed:

A single colony from agar plate was incubated in LB media and a selection marker at 37° C. overnight. The main culture was prepared by applying a seeding factor of 100 from the overnight culture and incubation in TB media with 1 mM $MgSO_4$ and a selection marker at 37° C. up to $OD_{600}$ 0.8. The gene expression was induced by addition of 0.4 mM IPTG and cultivation at 16° C. for ~ 20 hrs. Cells were harvested by centrifugation at 7,000×g for 30 min. Afterwards, the cell pellet was resuspended in lysis buffer. Cells lysis was conducted by high pressure homogenization (800-1000 psi). Cell lysates were centrifuged at 7,000×g for 30 min and filtered through a 0.8 μm filter. Enzymes were purified through nickel affinity chromatography (see following slides).

Enzyme Purification

The clear cell lysate was loaded on a Ni-NTA affinity column on an AKTA system. The column was washed with 20% of elution buffer. Enzymes were eluted using elution buffer. Enzyme solutions were concentrated and dialysed (to remove imidazole) with 3 kDa Amicon filters and then stored in storage buffer at −20° C.

Buffer Composition of Lysis/Binding Buffer (A), Elution Buffer (B) and Storage Buffer (C)

TABLE 2

| Lysis/binding buffer (A) | |
|---|---|
| Lysis/Binding buffer | Conc. (mM) |
| MOPS | 50 mM |
| NaCl | 300 mM |
| $MgCl_2$ | 10 mM |
| glycerol | 5% |
| imidazole | 10 mM |
| pH | 7.4 |

TABLE 1

| Enzymes used in this example | | | | |
|---|---|---|---|---|
| Enzyme | Abbreviation | EC class | Origin | SEQ ID |
| AGE family epimerase/isomerase | AGE | 5.1.3.8 | *Trichormus variabilis* | SEQ ID 1 |
| N-acetylneuraminate lyase | NAL | 4.1.3.3 | *Pasteurella multocida* (strain Pm70) | SEQ ID 2 |
| N-acylneuraminate cytidylyltransferase | CSS | 2.7.7.43 | *Neisseria meningitidis* MC58 (serogroup B) | SEQ ID 3 |
| Uridine kinase | UDK | 2.7.1.48 | *Escherichia coli* (strain K12) | SEQ ID 4 |
| Uridine monophosphate kinase | URA6 | 2.7.4.47 | *Arabidopsis thaliana* | SEQ ID 5 |
| Polyphosphate kinase 3 | PPK3 | 2.7.4.1 | *Ruegeria pomeroyi* (strain ATCC 700808/DSM 15171/DSS-3) | SEQ ID 6 |
| Inorganic diphosphatase | PPA | 3.6.1.1 | *Pasteurella multocida* (strain Pm70) | SEQ ID 7 |
| 2-domain polyphosphate kinase 2 | 2D-PPK2 | 2.7.4.1 | *Pseudomonas aeruginosa* | SEQ ID 8 |
| 1-domain polyphosphate kinase 2 | 1D-PPK2 | 2.7.4.1 | *Pseudomonas aeruginosa* | SEQ ID 9 |

TABLE 3

Elution buffer (B)

| Elution buffer | Conc. (mM) |
| --- | --- |
| MOPS | 50 mM |
| NaCl | 300 mM |
| MgCl$_2$ | 10 mM |
| glycerol | 5% |
| imidazole | 250 mM |
| pH | 7.4 |

TABLE 4

Storage buffer (C)

| Enzyme Storage buffer | Conc. (mM) |
| --- | --- |
| MOPS | 25 mM |
| NaCl | 150 mM |
| MgCl$_2$ | 5 mM |
| glycerol | 5% |
| pH | 7.4 |

Plasmids and Stock Cultures

Stock solutions of all E. coli cultures carrying the plasmids (pET28a with kanamycin resistance) with the gene sequences were available from earlier studies [1,2]. The stock solutions contained 50% glycerol and were kept at −20° C.

The gene and corresponding protein sequences were obtained from the UniProt database: AGE (WP_011320279.1), NAL (Q9CKB0), CSS (P0A0Z7), UDK (P0A8F4, URA6 (O04905), PPA (P57918), PPK3 (Q5LSN8), 2DPPK2 (Q9HYF1), and 1 DPPK2 (Q92SA6). The plasmids were ordered from commercial suppliers (BioCat GmbH):

TABLE 5

Enzymes and plasmids used in the experiments

| Enzyme | Vector | Selection marker |
| --- | --- | --- |
| AGE | pET-28a(+) | Kanamycin |
| NANA | pET-22b(+) | Ampicilin |
| UDK | pET-28a(+) | Kanamycin |
| CSS | pET-100/D-TOPO | Ampicilin |
| URA6 | pET-28a(+) | Kanamycin |
| PPK3 | pET-28a(+) | Kanamycin |
| PmPPA | pET-28a(+) | Kanamycin |
| 1D-PPK2 | pET-28a(+) | Kanamycin |
| 2D-PPK2 | pET-28a(+) | Kanamycin |

PPA (PmPpA; enzymes carrying a C-terminal hexahistidin-tag (His-tag)), PPK3 and URA6 (for an N-terminal His-tag). After transformation of the plasmids into E. coli, the DNA was isolated and the accuracy of the constructs was checked by gene sequencing (Eurofins Genomics, Ebersberg, Germany).

1. Mahour, R., et al., *Establishment of a five-enzyme cell-free cascade for the synthesis of uridine diphosphate N-acetylglucosamine*. Journal of Biotechnology, 2018. 283: p. 120-129.
2. Rexer, T. F. T., et al., *One pot synthesis of GDP-mannose by a multi-enzyme cascade for enzymatic assembly of lipid-linked oligosaccharides*. Biotechnology and Bioengineering, 2018. 115(1): p. 192-205.

One-Pot Cascade Reactions

Immobilized enzymes can often be separated from solutions and reused. Moreover, they may exhibit higher activity and can be used for a wide range of processes, such as continuous synthesis in packed bed reactors. A wide range of commercially available solid supports were tested for the co-immobilization of the CMP-Neu5Ac multi-enzyme cascade.

Reactions

Cascade reactions were conducted in 1.5 mL safe-lock Eppendorf vials in volumes of 150 µL at 35° C. in a thermomixer at 450 rpm shaking.

All enzymes were mixed into one vial

Reactions were started by mixing enzymes, buffers and reactants

For profiling the time course of the reaction, at each time point 3 µL sample were aliquoted and quenched by adding 297 µL cold (4° C.) dH2O and measured by anion exchange chromatography without delay.

Measurements

High-performance anion exchange chromatography (HPAEC) with UV (260 nm) and pulsed amperometric detection (PAD) was utilized to measure concentrations of reactants. For analyte separation and quantification a step gradient elution method was developed and validated chromatographic separation was performed at a system flow of 0.5 mL/min using a non-porous pellicular column CarboPac PA200 (250×2 mm). The HPAEC system (ICS5000) as well as all columns, components and software were purchased from Thermo Scientific (Waltham, USA).

Enzyme Immobilization

It should be noted that finding the optimal solid support is always down to experimental trial and error as insufficient knowledge about the immobilization of enzymes exist to predict the optimal solid support.

The surprising finding was that the multi-enzyme cascade showed activity when co-immobilized on a wide range of epoxy supports. The epoxy supports that were tested and showed activity varied in support matrix, particle size, pore size and oxiran content. Other solid supports where enzymes are immobilized by hydrophobic adsorption, ionic interaction or covalent crosslinking with glutaraldehyde showed very little to no activity implying that at least one of the five key enzymes are little active to inactive. Moreover, the multi-enzyme cascade was active on epoxy supports when a large range of different rations of proteins to solid supports where used. For the synthesis of CMP-Neu5Ac, many of the epoxy supports loaded with the enzymes could be used in more than 20 reaction cycles without re-immobilizing the enzymes on the supports. Tested Epoxy supports are summarized in Table 7.

TABLE 7

Selection of tested epoxy (including amino-epoxy) supports

| Resin | Mass (mg) |
| --- | --- |
| EC-EP | 109 |
| EP403/M | 91 |
| IB-COV1 | 95 |
| IB-COV2 | 111 |
| IB-COV3 | 91 |
| Eupergit ® CM | 100 |
| ECR8215F | 92 |
| ECR8204F | 84 |
| ECR8209F | 84 |
| ECR8285 | 84 |
| EP403/S | 82 |
| EP400/SS | 102 |
| EC-HFA/M | 111 |

TABLE 7-continued

Selection of tested epoxy (including amino-epoxy) supports

| Resin | Mass (mg) |
|---|---|
| HFA403/M | 98 |
| HFA403/S | 94 |
| EC-HFA/S | 104 |

Experiment A

A wide range of commercially available solid supports (see Table 7) were tested for the co-immobilization of the enzymes, NmCSS, PPK3 and URA6, used in the CMP-Neu5Ac synthesis (see FIG. 1) and their effect on the synthesis of CMP-Neu5Ac was evaluated.

To test the multi-enzyme cascade on various enzyme loaded beads, a given mass (see Table 1) of each resin was added.

100 μL of reaction buffer (see below) was added to the beads and incubated at 30° C. and 550 rpm for 20 h. Afterwards, the supernatant was analyzed for CMP-Neu5Ac. The CMP-Neu5Ac concentrations were then measured by HPAEC-UV/PAD.

Results:

Surprisingly it has been found that co-immobilization of the set of enzymes results in a higher productivity in the production of cytidine 5'-monophospho-N-acetylneuraminic acid (CMP-Neu5Ac) compared to non-immobilized or separately immobilization of the enzymes. Thus, preferably the enzymes used in the inventive methods described herein are co-immobilized on a solid support. Surprisingly, the beads with the enzyme can be used in more than 11 cycles (see FIGS. 11-25).

TABLE 8

Concentration of reactants in the feed solution of Experiment A

| Substrate | Conc. (mM) |
|---|---|
| Neu5NAc | 5 |
| CMP | 5 |
| ATP | 5 |
| PolyP$_{25}$ | 30 |
| MgCl$_2$ | — |
| HEPES | — |

Experiment C—Proof of Concept

To check whether CMP-Neu5Ac can be produced in a one-pot reaction using the designed pathway, a reaction with the concentrations as detailed in the table below was conducted. The concentrations of reactants were measured over the time (see chromatograms after 4 min and 30 hours below). As shown in the chromatogram below, CMP-Neu5Ac was produced. The concentration time course of CMP-Neu5Ac is shown below.

TABLE 9

Concentration of reactants in the feed solution.

| Enzyme/Compound | Conc./Mass |
|---|---|
| AGE | 2.57 μg |
| NANA | 3 μg |
| CSS | 3 μg |
| UDK | 8.8 μg |
| URA6 | 8 μg |
| PPK3 | 21 μg |
| GlcNAc | 5 mM |
| Cytidine | 2 mM |
| Pyruvate | 5 mM |

TABLE 9-continued

Concentration of reactants in the feed solution.

| Enzyme/Compound | Conc./Mass |
|---|---|
| ATP | 4 mM |
| PolyP$_{25}$ | 4 mM |
| MOPS | 50 mM |
| MgCl2 | 20 mM |
| pH | 7.4 |
| Volume | 150 μL |

Results

It was shown that with the set of enzyme, CMP-Neu5Ac could successfully be produced from GlcNAc, pyruvate and cytidine.

Experiment D—Increased Substrate Concentrations

In experiment D, two cascade reaction (D1 with and D2 without PPA) were conducted with higher substrate concentrations (see below for initial concentrations). After overnight incubation the reactant concentrations were measured by HPAEC-UV detection.

CMP-Neu5Ac was successfully synthesized through the cascades. However, considerable concentration of CMP, CDP and CTP were detected implying low yields.

TABLE 10A

Figure 6:
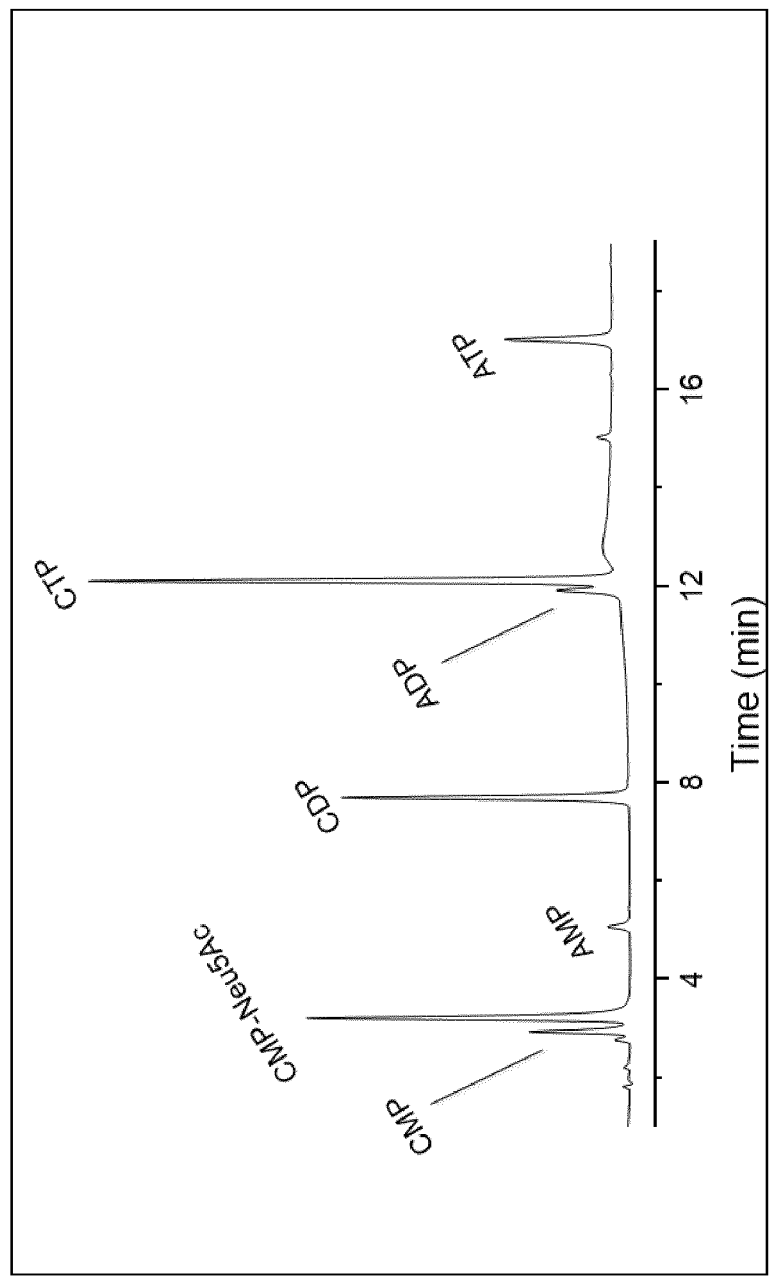
FIG. 6 shows the chromatogram of reaction D1, Measured after overnight incubation.

Initial concentration of reactants for reaction
D1 - cascade reaction without PPA (see FIG. 6)

| Enzyme | Conc. (μg/μL) |
|---|---|
| UDK | 95 |
| URA6/PPK3 | 185 |
| CSS | 1225 |
| AGE | 28 |
| NANA | 841 |

| Reactants | Conc. (mM) |
|---|---|
| Cytidine | 36 |
| GlcNAc | 39.6 |
| Pyruvate | 39.6 |
| ATP | 3.6 |
| PolyP$_{25}$ | 14.5 |

| Buffer | Conc. (mM) |
|---|---|
| Tris (8.5) | 145 |

| Co-factor | Conc. (mM) |
|---|---|
| MgCl$_2$ | 54 |

| Total volume (μL) | |
|---|---|
| 227.5 | |

TABLE 10B

Figure 7:
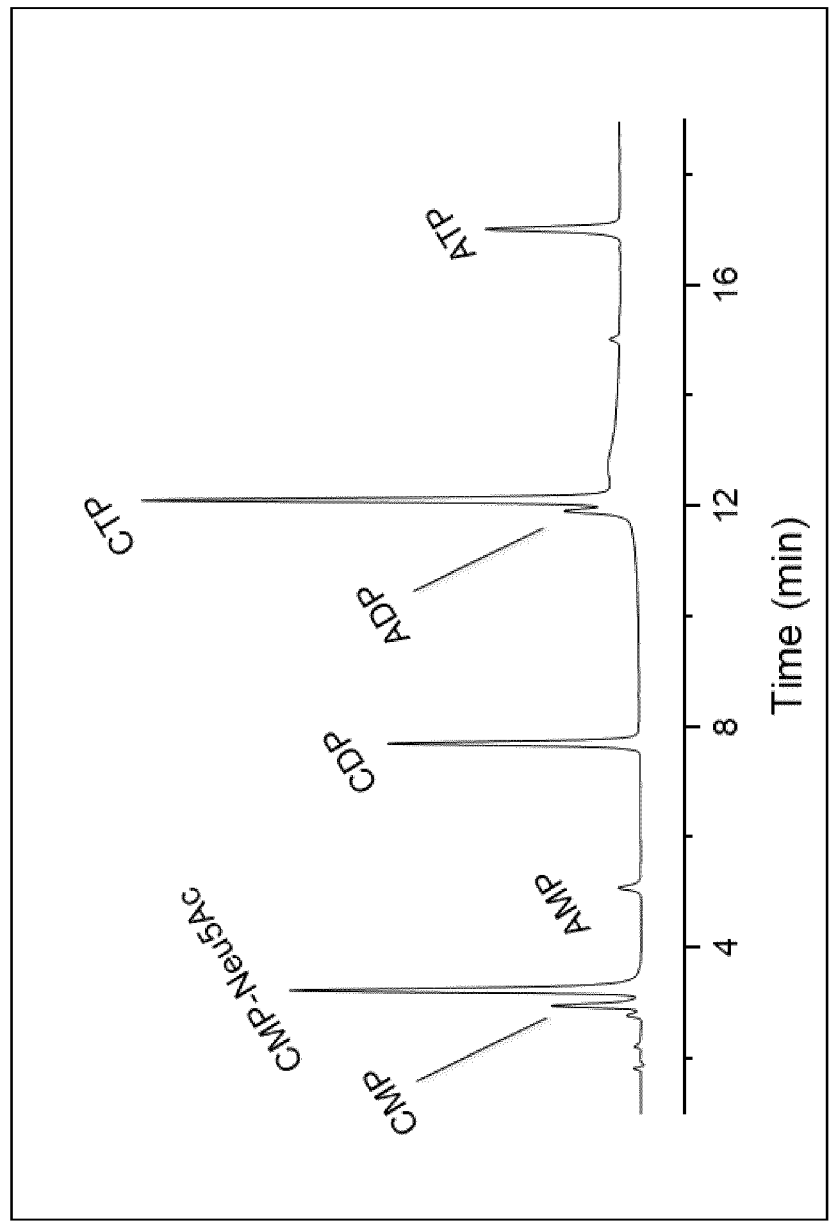
FIG. 7 shows the chromatogram of reaction D2, Measured after overnight incubation.

Initial concentration of reactants for reaction
D2 - cascade reaction with PPA (see FIG. 7)

| Enzyme | Conc. (μg/μL) |
|---|---|
| UDK | 93 |
| URA6/PPK3 | 155 |
| CSS | 1203 |
| AGE | 27 |
| NANA | 826 |
| PPA | 56 |

TABLE 10B-continued

Initial concentration of reactants for reaction
D2 - cascade reaction with PPA (see FIG. 7)

| Reactants | Conc. (mM) |
|---|---|
| Cytidine | 35.4 |
| GlcNAc | 39 |
| Pyruvate | 39 |
| ATP | 3.5 |
| PolyP$_{25}$ | 14.1 |

| Buffer | Conc. (mM) |
|---|---|
| Tris (8.5) | 140 |

| Co-factor | Conc. (mM) |
|---|---|
| MgCl$_2$ | 53 |

| Total volume (μL) |
|---|
| 282.5 |

Experiment E—Inhibition of AGE by CTP

As know from the literature, CTP inhibits AGE. We independently verified this in a reaction starting the synthesis of CMP-Neu5Ac from GlcNAc and CTP (see below). The initial substrate and enzyme concentrations are shown in the table below.

In an overnight reaction very little CMP-Neu5Ac was detected, verifying the inhibition of AGE by CTP (see chromatogram below).

Scheme 1: Shortened pathway starting the synthesis of CMP-Neu5Ac
from GlcNAc and CTP to detect AGE inhibition by CTP.

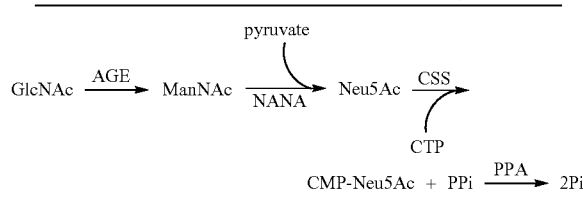

TABLE 11

Figure 8:
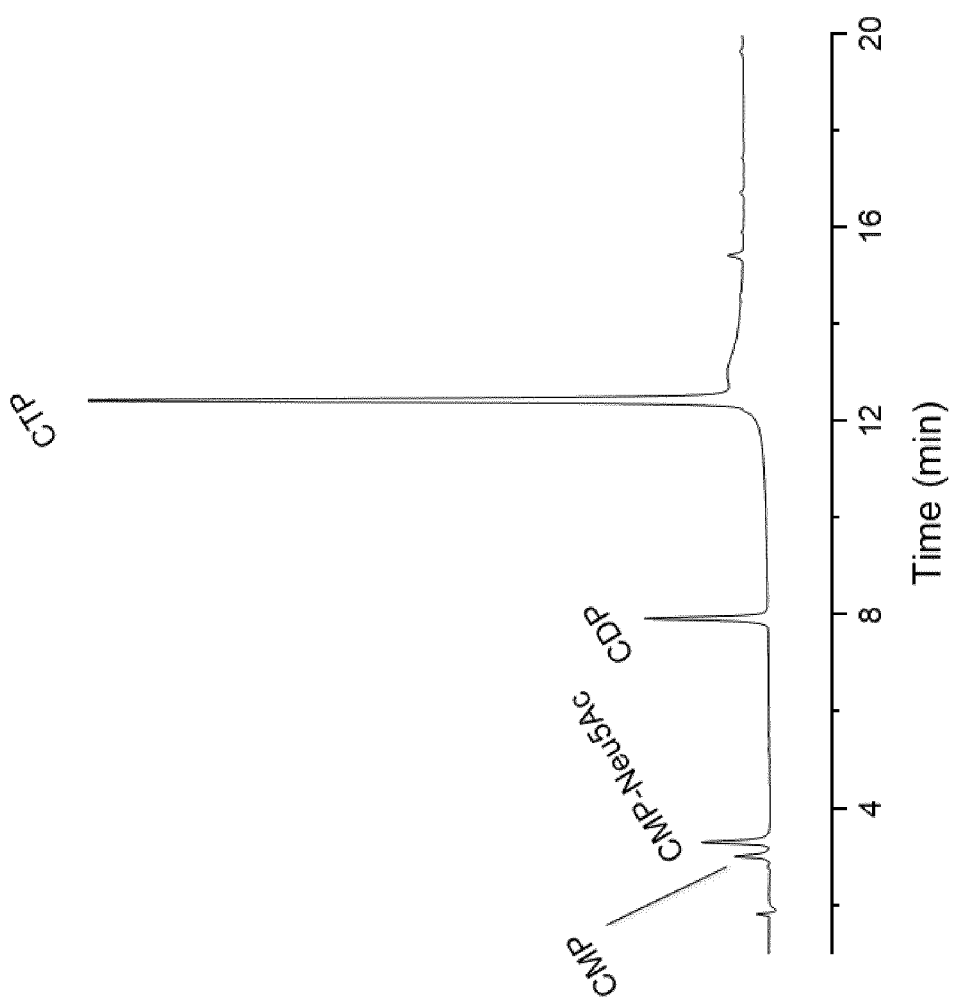
FIG. 8 shows the chromatogram of reaction E: synthesis of CMP-Neu5Ac. Strong inhibition of AGE by CTP.

Initial substrate and enzyme concentration
of experiment E (see also FIG. 8)

| Enzyme | Conc. (μg/μL) |
|---|---|
| UDK | 26 |
| URA6/PPK3 | 778 |
| CSS | 1275 |
| PPA | 47 |

| Reactants | Conc. (mM) |
|---|---|
| GlcNAc | 10 |
| Pyruvate | 10 |
| CTP | 10 |

| Buffer | Conc. (mM) |
|---|---|
| Tris (8.5) | 150 |

TABLE 11-continued

Initial substrate and enzyme concentration
of experiment E (see also FIG. 8)

| Co-factor | Conc. (mM) |
|---|---|
| MgCl$_2$ | 50 |

| Total volume (μL) |
|---|
| 200 |

Experiment F—Increasing the Yield

It is known that CTP inhibits AGE and ATP activates AGE. However, by adjusting the initial substrate and enzyme concentrations the yield and product concentration can be optimised. Decreasing cytidine is increasing the yield but decreases the CMP-Neu5Ac end concentration. In Experiment D, the ratio of cytidine-ATP-PolyP was kept constant (1-0.3-0.8) while the cytidine concentrations were increased (see below for initial concentrations).

Figure 9:
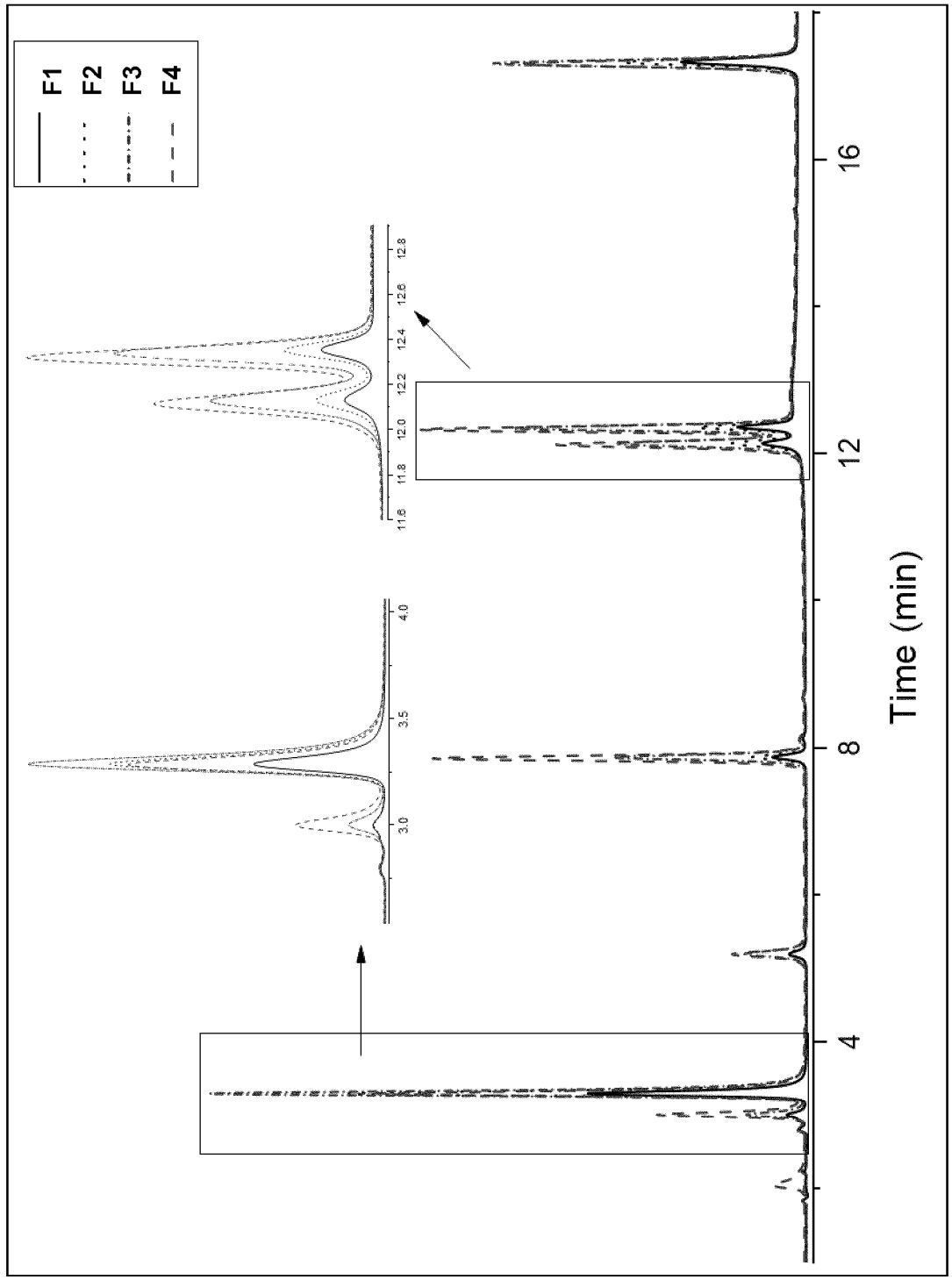
FIG. 9 shows the chromatogram of reaction F1-F4 after 40 hours of incubation. Initial concentration of reactants in the reactions F1-F4 are described in Table 12.

After 40 hours of incubation reactions F1 and F2 resulted in almost full conversion of cytidine to CMP-Neu5Ac as shown in FIG. 9.

TABLE 12

Initial concentration of reactions F1-F4 (see also FIG. 9)

| Reaction | F1 | F2 | F3 | F4 |
|---|---|---|---|---|
| Enzyme | Conc. (μg/μL) | | | |
| UDK | 65 | 61 | 56 | 53 |
| URA6/PPK3 | 82 | 76 | 71 | 66 |
| CSS | 1262 | 1173 | 1094 | 1024 |
| AGE | 38 | 35 | 33 | 31 |
| NANA | 1155 | 1075 | 1002 | 937 |
| PPA | 31 | 29 | 27 | 25 |
| Reactants | Conc. (mM) | | | |
| Cytidine | 10 | 18.4 | 25.7 | 32 |
| GlcNAc | 75 | 69 | 64.2 | 60.2 |
| Pyruvate | 80 | 73.5 | 68.5 | 64.2 |
| ATP | 3 | 5.3 | 7.8 | 9.6 |
| PolyP$_{25}$ | 8 | 14.5 | 20.5 | 26 |
| Buffer | Conc. (mM) | | | |
| Tris (8.5) | 150 | 140 | 130 | 120 |
| Cofactor | Conc. (mM) | | | |
| MgCl$_2$ | 75 | 70 | 65 | 60 |
| Total volume (μL) | 202 | 217 | 233 | 249 |

Experiment G

An additional reaction was carried out measuring concentrations over time (see below for initial concentrations). The reaction shows the conversion of cytidine, GlcNAc and pyruvate to CMP-Neu5Ac with a yield of about 75% with respect to cytidine and CMP-Neu5Ac titers of about 25 mM (16 g/L).

TABLE 13

Figure 10:
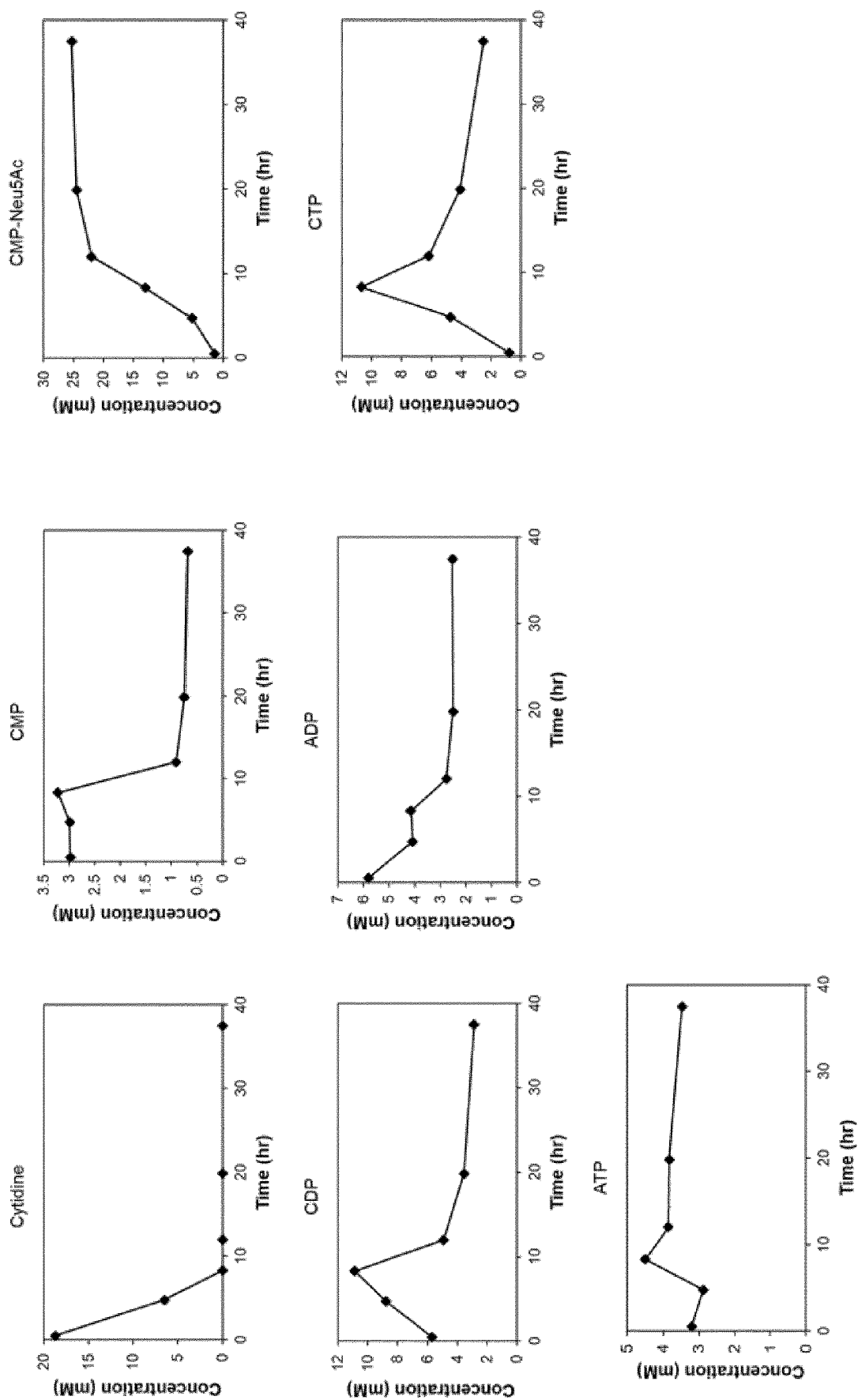
FIG. 10 shows concentrations over time of experiment G. Showing the enzymatic synthesis of CMP-Neu5Ac from cytidine, GlcNAc and pyruvate.
Figure 11:
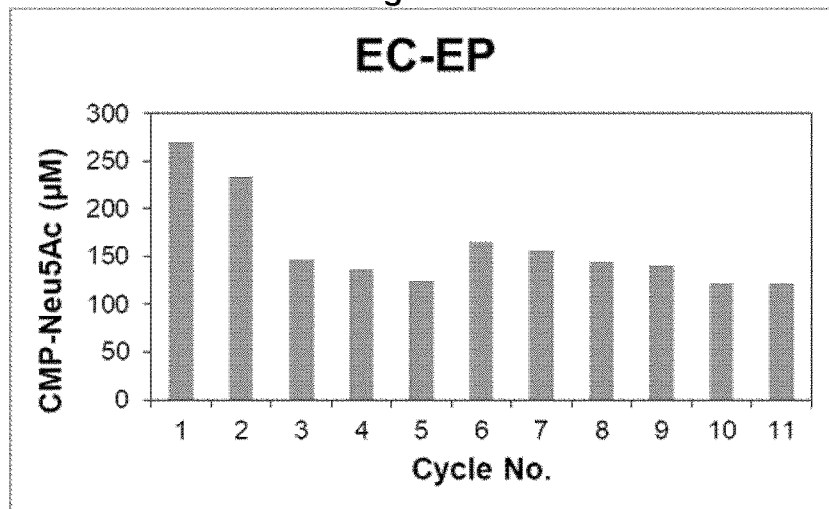
FIG. 11 shows the production of CMP-Neu5Ac in experiment A using co-immobilized enzymes (NmCSS, PPK3 and URA6) in multiple cycles when EC-EP resins were used as the solid support
Figure 12:
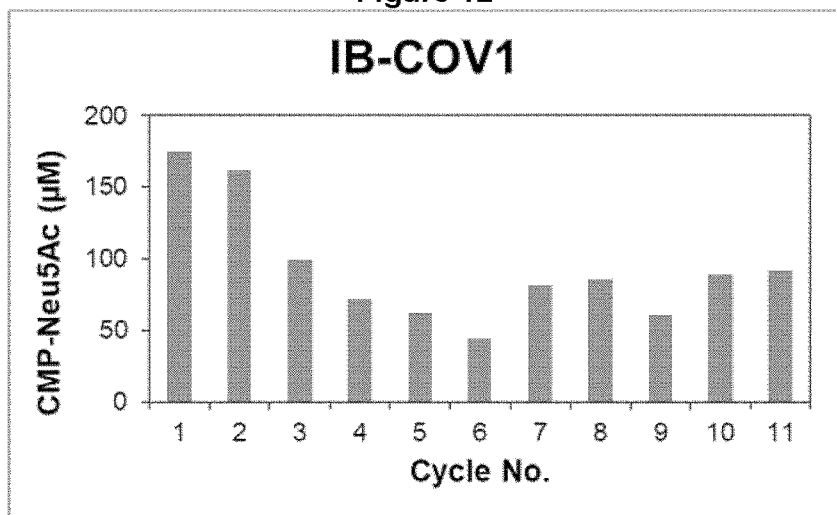
FIG. 12 shows the production of CMP-Neu5Ac in experiment A using co-immobilized enzymes (NmCSS, PPK3 and URA6) in multiple cycles when IBCOV-1 resins were used as the solid support
Figure 13:
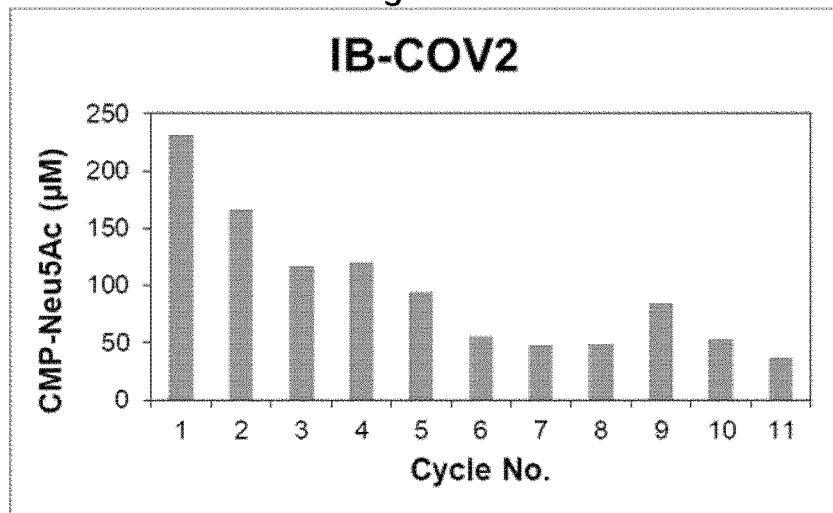
FIG. 13 shows the production of CMP-Neu5Ac in experiment A using co-immobilized enzymes (NmCSS, PPK3 and URA6) in multiple cycles when IBCOV-2 resins were used as the solid support
Figure 14:
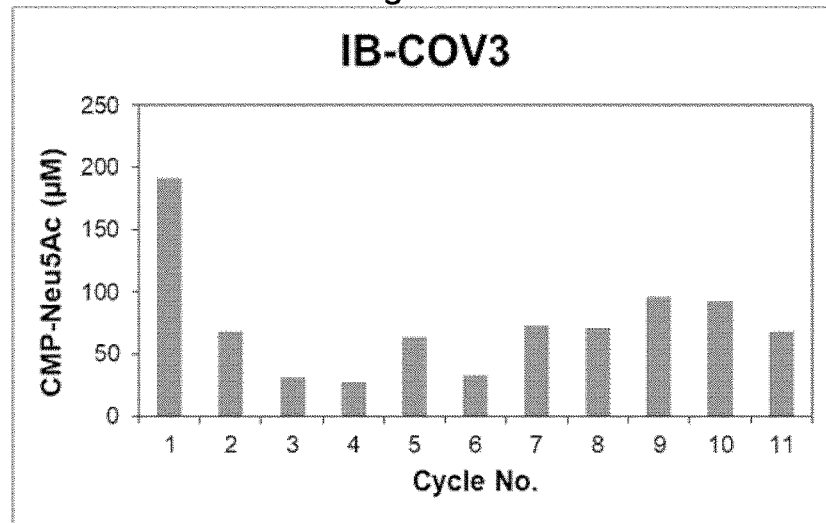
FIG. 14 shows the production of CMP-Neu5Ac in experiment A using co-immobilized enzymes (NmCSS, PPK3 and URA6) in multiple cycles when IBCOV-3 resins were used as the solid support
Figure 15:
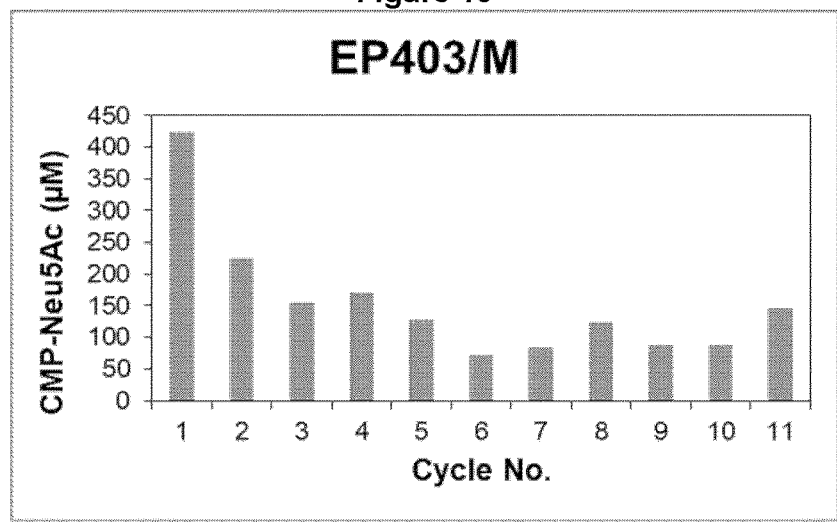
FIG. 15 shows the production of CMP-Neu5Ac in experiment A using co-immobilized enzymes (NmCSS, PPK3 and URA6) in multiple cycles when EP403/M resins were used as the solid support
Figure 16:
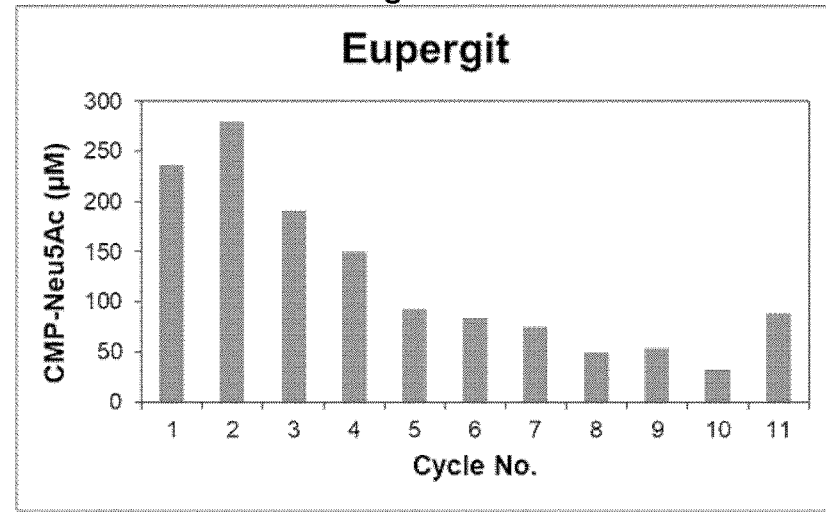
FIG. 16 shows the production of CMP-Neu5Ac in experiment A using co-immobilized enzymes (NmCSS, PPK3 and URA6) in multiple cycles when Eupergit resins were used as the solid support
Figure 17:
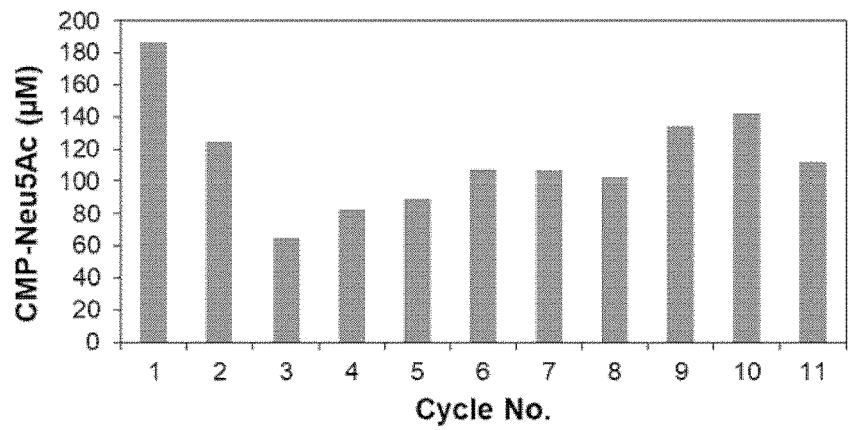
FIG. 17 shows the production of CMP-Neu5Ac in experiment A using co-immobilized enzymes (NmCSS, PPK3 and URA6) in multiple cycles when ECR8215F resins were used as the solid support
Figure 18:
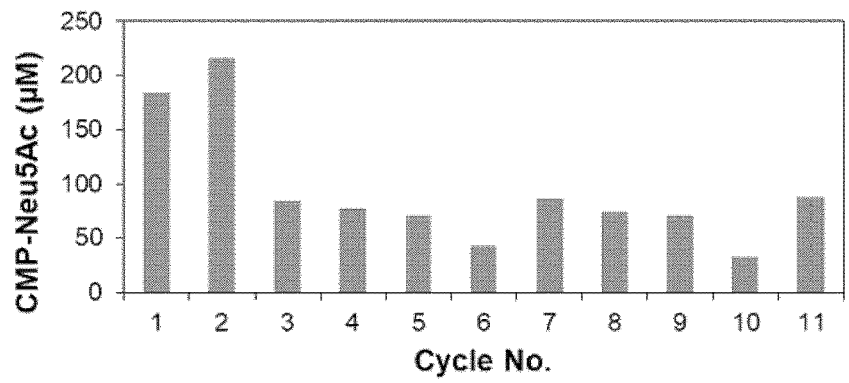
FIG. 18 shows the production of CMP-Neu5Ac in experiment A using co-immobilized enzymes (NmCSS, PPK3 and URA6) in multiple cycles when ECR8285 resins were used as the solid support
Figure 19:
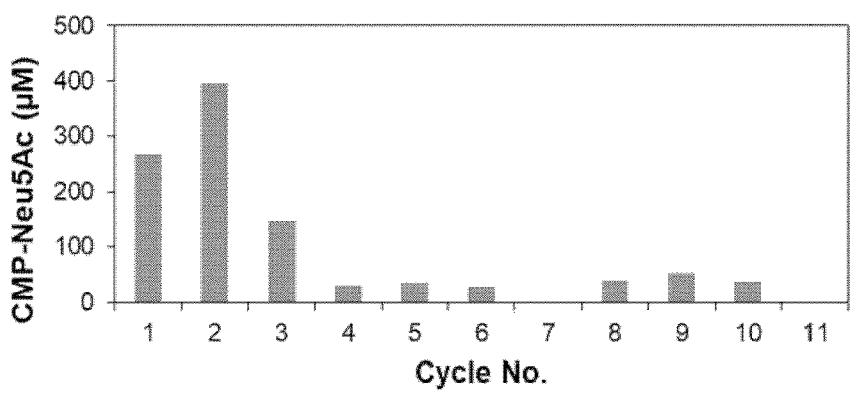
FIG. 19 shows the production of CMP-Neu5Ac in experiment A using co-immobilized enzymes (NmCSS, PPK3 and URA6) in multiple cycles when HFA403/M resins were used as the solid support
Figure 20:
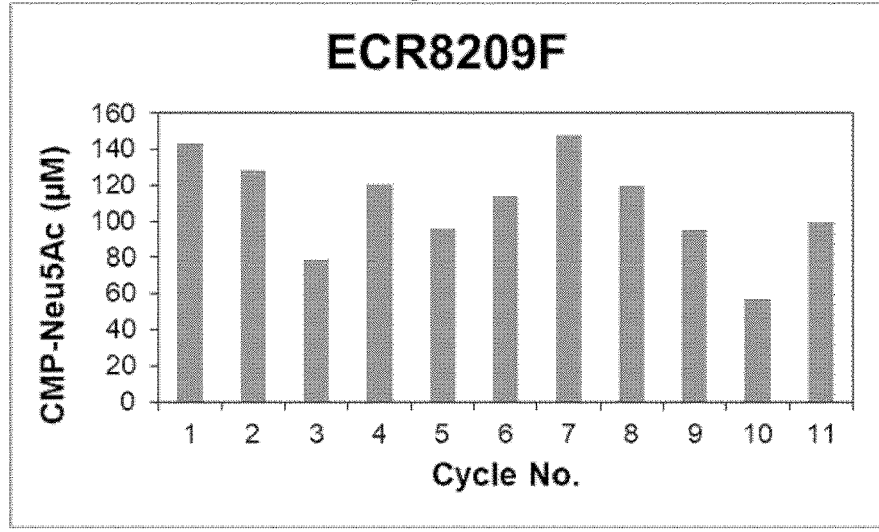
FIG. 20 shows the production of CMP-Neu5Ac in experiment A using co-immobilized enzymes (NmCSS, PPK3 and URA6) in multiple cycles when ECR8209F resins were used as the solid support
Figure 21:
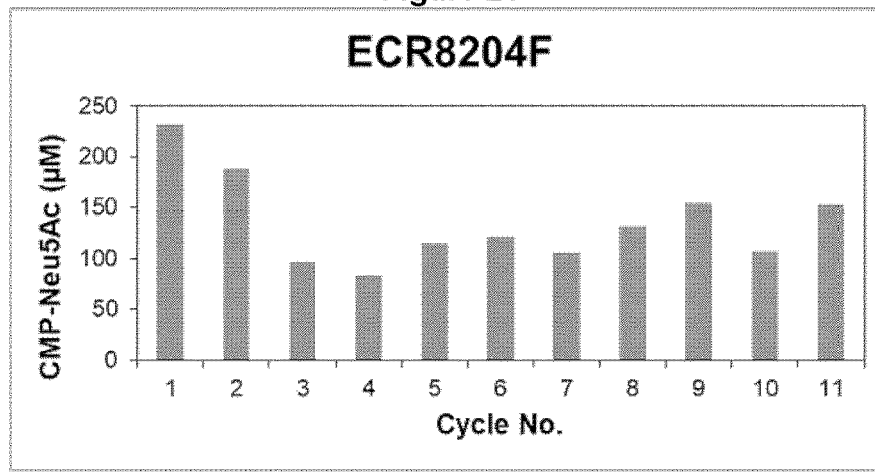
FIG. 21 shows the production of CMP-Neu5Ac in experiment A using co-immobilized enzymes (NmCSS, PPK3 and URA6) in multiple cycles when ECR8204F resins were used as the solid support
Figure 22:
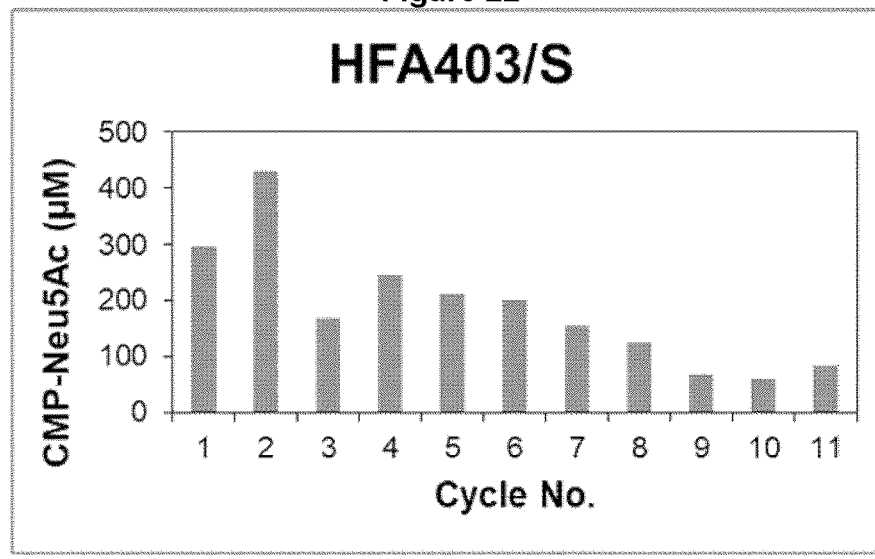
FIG. 22 shows the production of CMP-Neu5Ac in experiment A using co-immobilized enzymes (NmCSS, PPK3 and URA6) in multiple cycles when HFA403/S resins were used as the solid support
Figure 23:
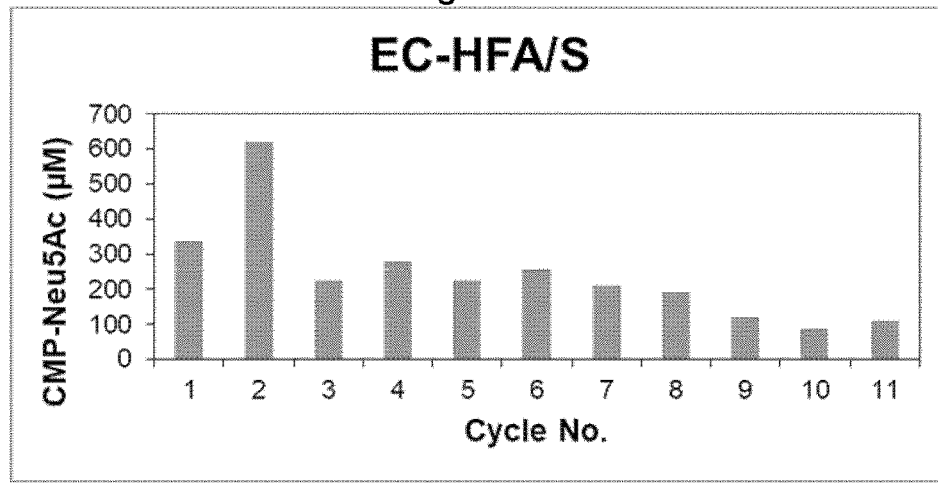
FIG. 23 shows the production of CMP-Neu5Ac in experiment A using co-immobilized enzymes (NmCSS, PPK3 and URA6) in multiple cycles when HFA/S resins were used as the solid support
Figure 24:
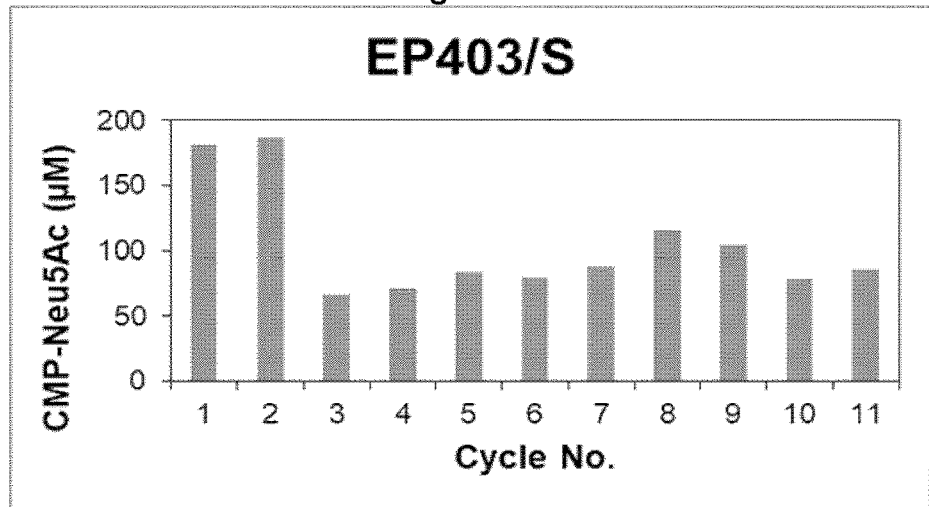
FIG. 24 shows the production of CMP-Neu5Ac in experiment A using co-immobilized enzymes (NmCSS, PPK3 and URA6) in multiple cycles when 403/S resins were used as the solid support
Figure 25:
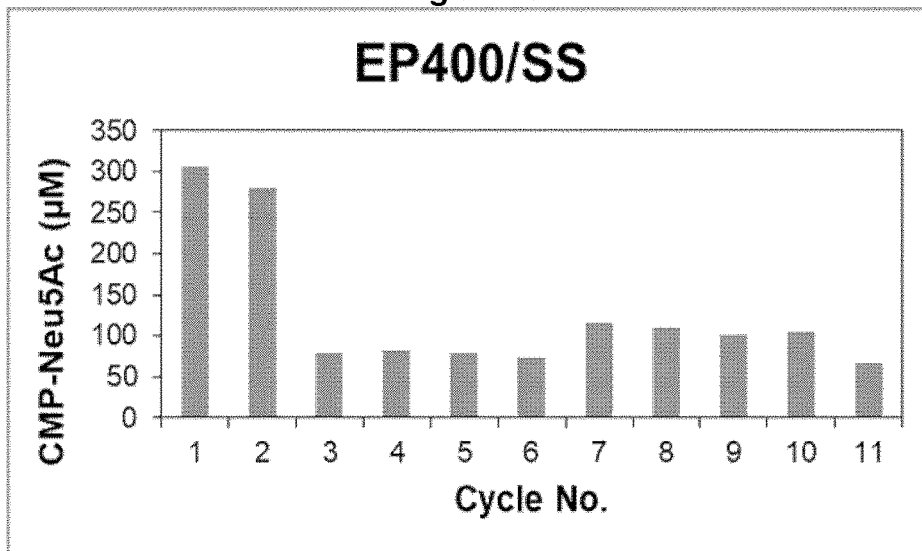
FIG. 25 shows the production of CMP-Neu5Ac in experiment A using coimmobilized enzymes (NmCSS, PPK3 and URA6) in multiple cycles when EP400/SS resins were used as the solid support FIG. 26. HPAEC-UV chromatogram of the 100 mL scale synthesis of CMP-Neu5Ac from CMP, Neu5Ac, PolyP$_n$, and catalytic amounts of ATP after 6.6 hours.

Initial concentration of experiment G (see also FIG. 10)

| Enzyme | Conc. (μg/μL) |
|---|---|
| UDK | 56 |
| URA6/PPK3 | 71 |

TABLE 13-continued

| Initial concentration of experiment G (see also FIG. 10) | |
| --- | --- |
| CSS | 1094 |
| AGE | 33 |
| NANA | 1002 |
| PPA | 27 |

| Reactants | Conc. (mM) |
| --- | --- |
| Cytidine | 33 |
| GlcNAc | 75 |
| Pyruvate | 80 |
| ATP | 9 |
| PolyP$_{25}$ | 24 |

| Buffer | Conc. (mM) |
| --- | --- |
| Tris (8.5) | 150 |

| Co-factor | Conc. (mM) |
| --- | --- |
| MgCl$_2$ | 75 |
| Total volume (µL) | 233.5 |

Example H: Simultaneous Production of Enzymes for the Synthesis of CMP-Neu5Ac at 100 mL Scale For the production of CMP-Neu5Ac from CMP, Neu5Ac, PolyP$_n$, and catalytic amounts of ATP one single strain was generated from which all three enzymes are overexpressed simultaneously. The genes and vectors used in this work are shown below:

TABLE 14

| Enzymes and vectors for the production of the cascade in one single strain. | | | | | |
| --- | --- | --- | --- | --- | --- |
| Gene | Enzyme | Source | Uniprot acc. No. | Plasmid | Restriction site |
| UMK3 | UMPK | Arabidopsis thaliana | O04905 | pACYCDuet | Ncol, Notl |
| SPO1727 | PPK3 | Ruegeria pomeroyi | Q5LSN8 | pACYCDuet | Ndel, Kpnl |
| neuA | CSS | Neisseria meningitidis | P0A0Z8 | pET100/D-TOPO | |

Figure 26:
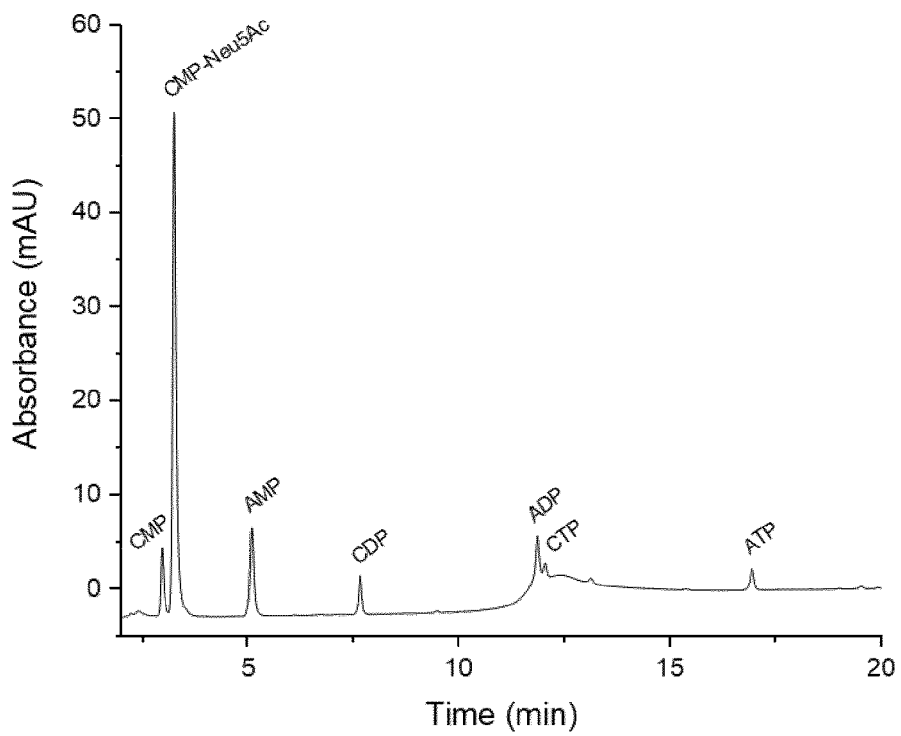

The biomass from a 200 mL culture was lysed by high pressure homogenizer in 40 mL lysis buffer containing 25 mM Tris-HCl (pH 7.1), 400 NaCl and 5% glycerol. After centrifugation, the supernatant containing the overexpressed enzymes was used to initiate a synthesis reaction. The 100 mL scale reaction was carried out in a spinner flask. The reaction matrix contained 150 mM Tris-HCl (pH 8.5), 75 mM MgCl$_2$, 50 mM CMP, 51 mM Neu5Ac, 5 mM ATP, 16 mM PolyP$_n$. After 6.6 h of incubation at 37° C. and 50 rpm, CMP-Neu5Ac was produced with a final concentration of 45.3 mM (27.8 g/L) and a yield of around 90%. The productivity was 4.2 g/(L*h). The chromatogram of the reaction mixture at the end of the reaction is shown in FIG. 26.

Example 3: Coupling of the Cascade

The cascade can be coupled to sialyltransferase to transfer CMP-Neu5Ac to acceptor molecules. Acceptor molecules can be for example monoclonal antibodies. For the coupling soluble sialyltransferase can be added, a sialyltransferase can be co-immobilized on the same support and/or the sialyltransferase can be immobilized on an additional support and then be added to reaction.

Example 4: Production of Neu5Acylated Biomolecules

The synthesis of Neu5Acylated biomolecules is facilitated by producing CMP-Neu5Ac in a one pot multi-enzyme cascade reaction first and then mixing it with the biomolecule substrate as well as a sialyltransferase to transfer Neu5Ac from CMP-Neu5Ac to the substrate. In the examples below the biomolecules are human milk oligosaccharides (HMOs).

Methods

All experiments were performed in 1.5 mL Eppendorf safe lock tubes and at 37° C. under shaking (550 rpm). For the identification of compounds, high performance anion chromatography (HPAEC) with pulsed amperometric detection (PAD) was used. The HPAEC system was equipped with Dionex™ CarboPac™ PA200 guard and analytical columns (in series, Thermo Scientific, USA). Aqueous solution with various concentrations of sodium hydroxide and sodium acetate were used as eluents.

Sample Preparation for Mass Spectrometry:

Before performing mass spectrometry (MS) on the samples, cotton hydrophilic interaction liquid chromatography (HILIC) was carried out to remove salts from the solution. In short, 15 µL of the samples were mixed with 85 µL of 100% acetonitrile (ACN). Approximately, one fifth of a 200 µL pipette tip was filled with cotton. Afterwards, the cotton was washed with water to remove any contamination. After equilibration with 85% ACN, samples were loaded by pipetting up and down, followed by washing steps (five times) with 85% ACN and 1% trifluoroacetic acid (TFA). Oligosaccharides were eluted from the cotton matrix with 50 µL of water in three steps (final volume: 150 µL).

Mass Spectrometry:

The UltraFlextreme matrix-assisted laser desorption/ionization time-of-flight (MALDI-TOF)-MS (Bruker Daltonics, Germany) was used for the analyses of HMOs and sugar nucleotides. For the analyses of HMOs, "super-DHB" (Merck, Germany) mixed with 10 mg/mL TA30 (2 mM NaCl in a solution consisting of 70% H$_2$O, supplemented with 0.1% TFA, and 30% ACN) was used the matrix. Briefly, 1 µL of matrix was spotted on a AnchorChip 384 BC MALDI target plate (Bruker Daltonics) and left to dry by air. Afterwards, a sample aliquot of 1 µL was added to the spots. After drying, 0.2 µL of ethanol per spot was added to allow rapid and homogenous recrystallization. The HMOs and sugar nucleotides analyses were measured in positive-ion, and negative-ion reflector mode, respectively. The calibration for positive-ion mode was carried out with a Dextran ladder.

Enzyme Preparation:

The list of genes, their origin and the vectors used are described in Table 15. The LOBSTR E. coli (Kerafast, USA) strain was used as the expression host. The cells harboring the plasmids were cultivated in terrific broth media supplemented with 1.5 mM MgSO$_4$ and selection markers at 37° C. At an OD of 0.8-1 the gene expression was induced by the addition of 0.4 mM IPTG, followed by 20-24 hours of incubation at 16° C. (15° C. for the α-2,6-sialyltransferase).

TABLE 15

List of genes, their origin, and plasmid used for heterologous expression

| Enzyme | Gene | Full name | origin | Plasmid |
|---|---|---|---|---|
| LGTA | LgtA | β-1,3-N-acetylglucosamine transferase | *Neisseria meningitidis* | pMAL-c4X |
| LGTB | LgtB | β-1,4-galactosyltransferase | *Neisseria meningitidis* | pET-15b |
| α-2,6-ST | P145-ST | α-2,6-sialyltransferase | *Photobacterium leiognathi* | pCold II |

At the end of cultivation, the cells were precipitated by centrifugation (7000×g, 30 minutes) and lysed by high-pressure homogenization (3 to 5 passages at 800-1000 psg). Afterwards, cell debris was removed by centrifugation (7000×g, 45 minutes) and filtration of supernatant through a 0.45 μm cellulose acetate filter. For the purification of enzymes, common His-tag purification method were used. The binding (lysis) buffer was: 50 mM MOPS (pH 7.5). 10 mM $MgCl_2$, 300 mM NaCl, 5% glycerol, and 10 mM imidazole. The elution buffer was 50 mM MOPS (pH 7.5). 10 mM $MgCl_2$, 300 mM NaCl, 5% glycerol, and 250 mM imidazole.

After elution, fractions containing the enzymes of interest were pooled together. A buffer exchange and enzyme concentration was carried out using 3 kDa Amicon filter units. Enzymes were mixed 1:1 with glycerol and stored at −20° C.

Figure 27:
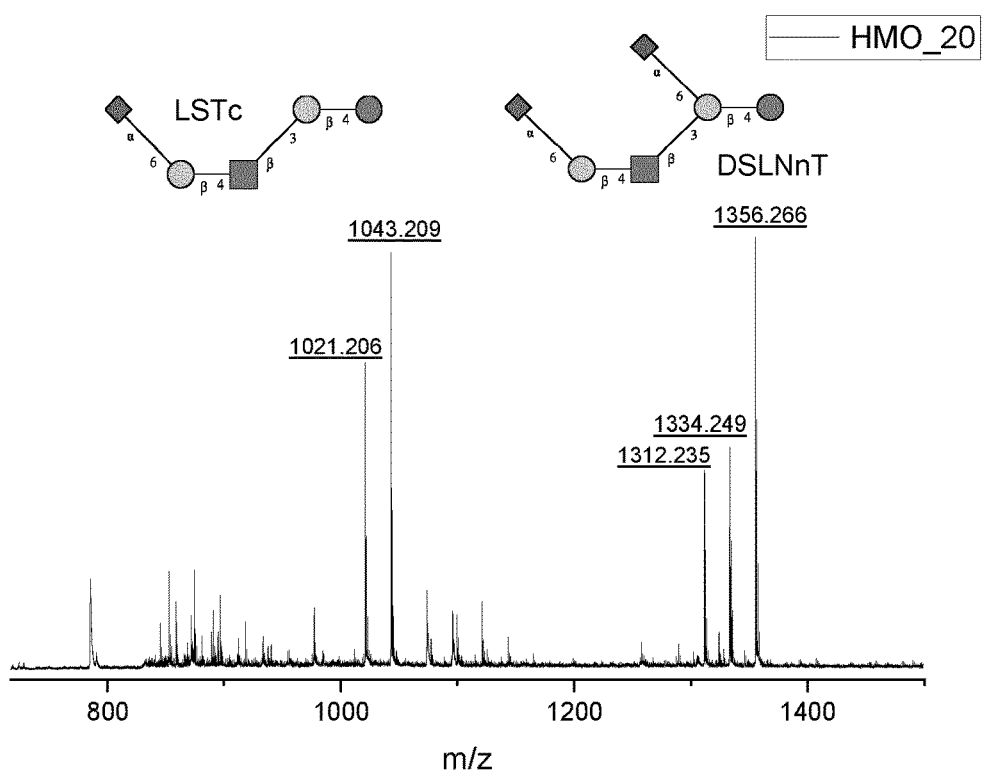
FIG. 27. Mass spectra of Neu5Acylated products LSTc and DSLNnT.

Example 4-1: Production of sialyllacto-N-neotetraose c (LSTc) and disialyllacto-N-neotetraose (DSLNnT CMP-Neu5Ac was produced in one-pot multi-enzyme reaction using the cascade described earlier (for the reaction condition see Table 16). Afterwards, an aliquot (70 μL) of the latter was mixed with a buffered (Tris-HCl) solution (198 μL, pH 8.5) containing LNnT, alkaline phosphatase (30 units) and α-2,6-sialyltransferase (α-2,6-ST). The production of LSTc and DSLNnT was confirmed by MALDI-TOF-MS (see FIG. 27).

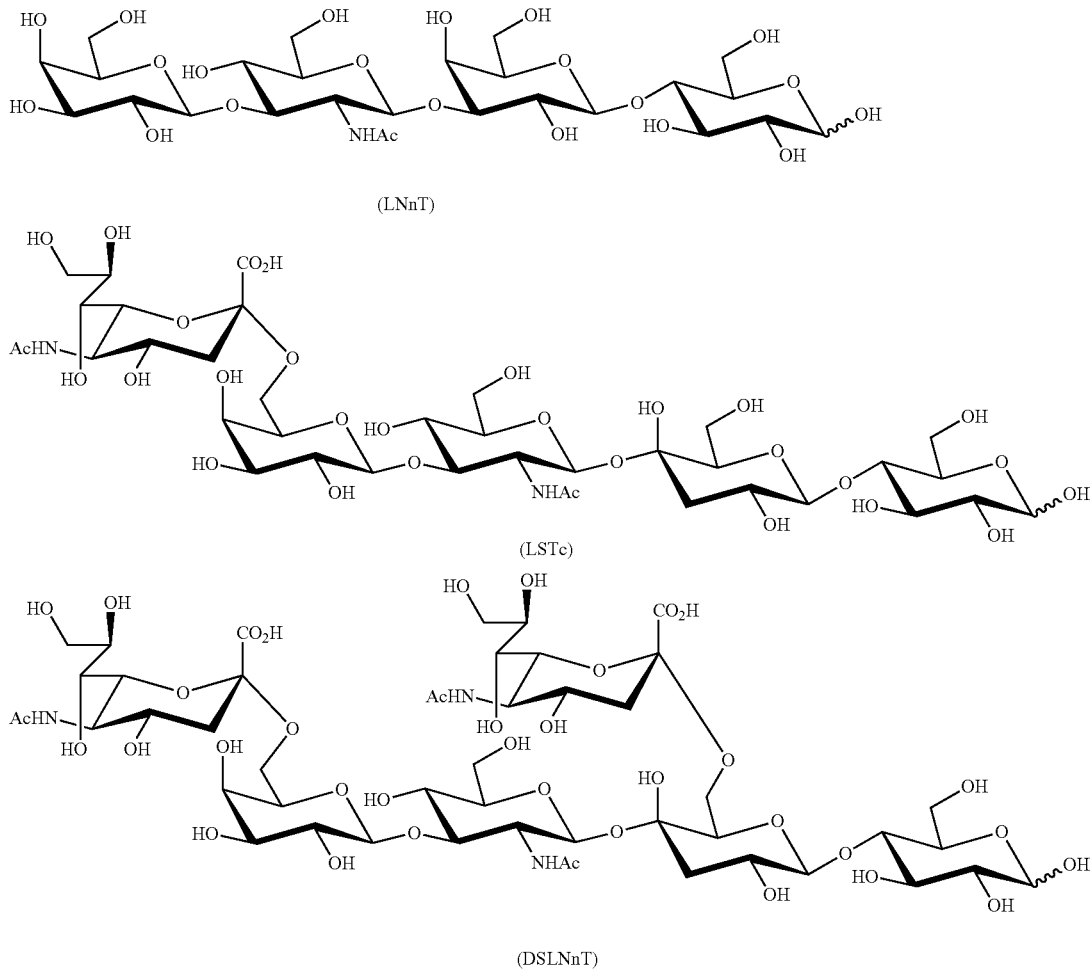

(LNnT)

(LSTc)

(DSLNnT)

TABLE 16

Reaction condition for the production of CMP-Neu5Ac.

| Enzyme | Concentration (μg/mL) | Reactants | Concentration (mM) |
|---|---|---|---|
| UDK | 56 | cytidine | 33 |
| URA6/PPK3 | 71 | GlcNAc | 75 |
| CSS | 1094 | pyruvate | 80 |
| AGE | 33 | ATP | 2.6 |
| NANA | 1002 | PolyP$_{25}$ | 24 |
| PPA | 27 | | |

| Buffer | Concentration (mM) |
|---|---|
| Tris (8.5) | 150 |

| Co-factor | Concentration (mM) |
|---|---|
| MgCl$_2$ | 75 |

| Total volume (μL) |
|---|
| 233.5 |

Example 4-2: Production of 6'-Sialyllactose (6'-SL

For the synthesis of 6'-SL from lactose and CMP-Neu5Ac, 70 μL of previously detailed one-pot reaction mix containing CMP-Neu5Ac (see Table 16) as the product was mixed with lactose (20 mM), MnCl$_2$ (20 mM), Tris-HCl (150 mM-pH 8), and 0.3 μg/μL α-2,6-ST to a final volume of 200 μL. The successful production of 6'-SL is confirmed by the HPAEC chromatogram and MS/MS spectra of the reaction mix at the reaction end point (see FIG. 28).

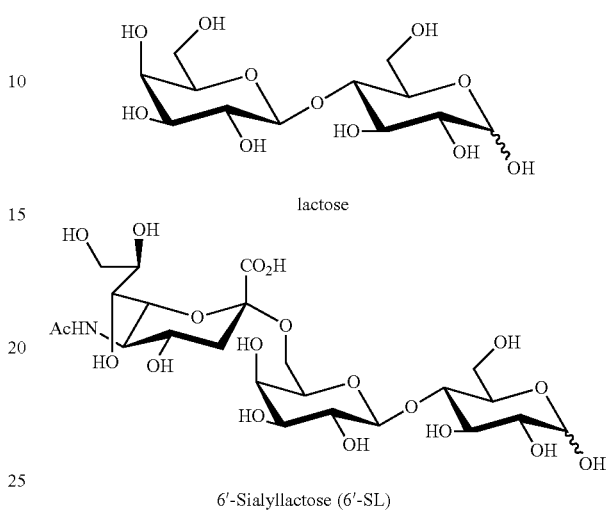

lactose

6'-Sialyllactose (6'-SL)

The invention claimed is:

1. A method for producing cytidine 5'-monophospho-N-acetyl-neuraminic acid (CMP-Neu5Ac, 1)

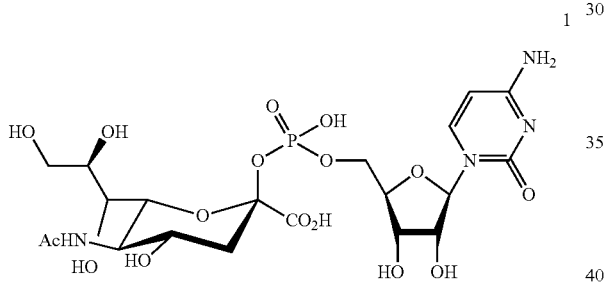

comprising:
A) providing a solution comprising N-acetyl-D-glucosamine, pyruvate, polyphosphate, cytidine, and adenosine 5'-triphosphate (ATP), and
a set of enzymes comprising an N-acylglucosamine 2-epimerase (AGE, EC 5.1.3.8), an N-acetylneuraminate lyase (NAL, EC 4.1.3.3), an N-acylneuraminate cytidylyltransferase (CSS, EC 2.7.7.43), a uridine kinase (UDK, EC 2.7.1.48), a uridine monophosphate kinase (URA6, EC 2.7.4.22) and a polyphosphate kinase 3 (PPK3, EC 2.7.4.1);
B) mixing said solution and said set of enzymes and reacting a resulting solution to produce cytidine 5'-monophospho-N-acetyl-neuraminic acid (CMP-Neu5Ac),
wherein
the uridine kinase (UDK) transfers in situ the cytidine to cytidine monophosphate (CMP).

2. The method according to claim 1, wherein the set of enzymes further comprises an inorganic diphosphatase (PPA, EC 3.6.1.1).

3. The method according to claim 1, wherein the set of enzymes further comprises a one-domain polyphosphate kinase 2 (1D-PPK2, EC 2.7.4.1) and/or a two-domain polyphosphate kinase 2 (2D-PPK2, EC 2.7.4.1).

4. The method according to claim 1, wherein the resulting solution has a pH value in the range of 7.0-9.0.

5. The method according to claim 1,
wherein a concentration of N-acetyl-D-glucosamine is in the range of 1 mM to 5000 mM; and/or a concentration of the pyruvate is in the range of 1 mM to 5000 mM; and/or a concentration of the cytidine is in the range of 0.1 mM to 2000 mM; and/or a concentration of adenosine 5'-triphosphate (ATP) is in the range of 0.001 mM to 100 mM.

6. The method according to claim 1, wherein the ratio of the N-acetyl-D-glucosamine and the cytidine is in the range of 1:1 to 100:1.

7. The method according to claim 1, wherein the resulting solution further comprises $Mg^{2+}$ with a concentration in the range of 0.1 mM to 200 mM.

8. The method according to claim 1, wherein each of the enzymes has the following amino acid sequence:
the N-acylglucosamine 2-epimerase (AGE) comprises at least 80% of an amino acid sequence as set forth in SEQ ID NO: 1;
the N-acetylneuraminate lyase (NAL) comprises at least 80% of an amino acid sequence as set forth in SEQ ID NO: 2;
the N-acylneuraminate cytidylyltransferase (CSS) comprises at least 80% of an amino acid sequence as set forth in SEQ ID NO: 3;
the uridine kinase (UDK) comprises at least 80% of an amino acid sequence as set forth in SEQ ID NO: 4;
the uridine monophosphate kinase (URA6) comprises at least 80% of an amino acid sequence as set forth in SEQ ID NO: 5;
the polyphosphate kinase 3 (PPK3) comprises at least 80% of an amino acid sequence as set forth in SEQ ID NO: 6;
the inorganic diphosphatase (PPA) comprises at least 80% of an amino acid sequence as set forth in SEQ ID NO: 7;
the one-domain polyphosphate kinase 2 (1D-PPK2) comprises at least 80% of an amino acid sequence as set forth in SEQ ID NO: 9.

9. The method according to claim 1, wherein the set of enzymes is directly co-immobilized on a solid support from cell lysate or cell homogenate.

10. The method according to claim 9, wherein the solid support is composed of beads or resins comprising one or more selected from the group consisting of a polymer with epoxide functional groups, a polymer with amino epoxide functional groups, a polymer with ethylenediamine functional groups, a polymer with amino C2 functional groups, a polymer with amino C6 functional groups, and a polymer with anionic/amino C6 spacer functional groups.

11. The method according to claim 1, wherein the ratio of N-acetyl-D-glucosamine (GlcNAc) and pyruvate is in the range of 1:1 to 1:50;

the ratio of N-acetyl-D-glucosamine (GlcNAc) and cytidine is in the range of 1:1 to 100:1;

the ratio of adenosine 5'-triphosphate (ATP) and cytidine is in the range of 1:1 to 1:100; and the ratio of adenosine 5'-triphosphate (ATP) and polyphosphate is in the range of 1:1 to 1:200; and/or the concentration of N-acetyl-D-glucosamine (GlcNAc) is in the range of 20 to 3000 mM;

the concentration of pyruvate is in the range of 20 to 3000 mM;

the concentration of cytidine is in the range of 1 to 500 mM;

the concentration of adenosine 5'-triphosphate (ATP) is in the range of 0.001 to 10 mM; and the concentration of polyphosphate is in the range of 1 to 30 mM.

12. The method according to claim 1, wherein the N-acetyl-D-glucosamine (GlcNAc) is separately or in situ produced from D-glucosamine (GlcN) and acetate in the presence of N-acetyl-glucosamine deacetylase (EC 3.5.1.33).

13. A method for producing a Neu5Acylated biomolecule comprising
i) performing the method according to claim 1 to obtain a CMP-Neu5Ac,
ii) reacting the CMP-Neu5Ac with a biomolecule, wherein the biomolecule is a saccharide, a glycopeptide, a glycoprotein, a glycolipid, a glycan, a peptide, a protein, an antibody, an antibody drug conjugate, a carbohydrate conjugate vaccine, virus, virus like particles, virus vaccine, or a flavonoid by forming an O-glycosidic bond with an hydroxyl group of the biomolecule with removal of CMP group in the presence of a sialyltransferase.

14. The method according to claim 13, wherein the biomolecule contains any of galactoside (Gal), galactosamininde (GalN), N-acetylgalactosaminide (GalNAc), neuraminide (Neu), N-acetyl neuraminide (Neu5Ac), N-glycolylneuraminide, 3-Deoxy-D-glycero-D-galacto-2-nonulosonic Acid (KDN), and N-acetyllacosaminide (Gal-β-1-3-GlcNAc) moiety as terminal end group.

15. A set of enzymes comprising an N-acylglucosamine 2-epimerase (AGE, EC 5.1.3.8), an N-acetylneuraminate lyase (NAL, EC 4.1.3.3), an N-acylneuraminate cytidylyltransferase (CSS, EC 2.7.7.43), a uridine kinase (UDK, EC 2.7.1.48), a uridine monophosphate kinase (URA6, EC 2.7.4.22) and a polyphosphate kinase 3 (PPK3, EC 2.7.4.1), wherein the set of enzymes is co-immobilized on a polymer by covalent bonds.

16. The set of enzymes according to claim 15 further comprising an inorganic diphosphatase (PPA), a one-domain polyphosphate kinase 2 (1D-PPK2, EC 2.7.4.1) and/or a two-domain polyphosphate kinase 2 (2D-PPK2, EC 2.7.4.1).

17. The set of enzymes according to claim 15, further comprising an N-acetyl-glucosamine deacetylase (EC 3.5.1.33).

18. The set of enzymes according to claim 16, further comprising an N-acetyl-glucosamine deacetylase (EC 3.5.1.33).

* * * * *